US012103005B2

(12) United States Patent
Ness et al.

(10) Patent No.: US 12,103,005 B2
(45) Date of Patent: Oct. 1, 2024

(54) METHOD OF EMULSION FORMATION AND MODIFICATION

(71) Applicant: Bio-Rad Laboratories, Inc., Hercules, CA (US)

(72) Inventors: Kevin D. Ness, Pleasanton, CA (US); Christopher F. Kelly, Larkspur, CA (US); Donald A. Masquelier, Tracy, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 16/995,555

(22) Filed: Aug. 17, 2020

(65) Prior Publication Data

US 2021/0031200 A1 Feb. 4, 2021

Related U.S. Application Data

(63) Continuation of application No. 16/397,774, filed on Apr. 29, 2019, now Pat. No. 10,744,506, which is a (Continued)

(51) Int. Cl.
*B01L 3/00* (2006.01)
*B01F 23/41* (2022.01)
(Continued)

(52) U.S. Cl.
CPC ........ *B01L 3/502784* (2013.01); *B01F 23/41* (2022.01); *B01F 33/3011* (2022.01); (Continued)

(58) Field of Classification Search
CPC ......... B01L 3/502784; B01L 3/502715; B01L 3/502723; B01L 3/0275; B01L 7/52; (Continued)

(56) References Cited

U.S. PATENT DOCUMENTS 3,575,220 A 4/1971 Davis et al.
4,051,025 A 9/1977 Ito
(Continued)

FOREIGN PATENT DOCUMENTS

CN 2364458 2/2000
DE 102005037401 2/2007
(Continued)

OTHER PUBLICATIONS

Holtze et al, "Biocompatible surfactants for water-in-fluorocarbon emulsions" Lab Chip, 2008,8, 1632-1639. (Year: 2008).*
(Continued)

*Primary Examiner* — Dennis White
(74) *Attorney, Agent, or Firm* — Kolisch Hartwell, P.C.

(57) ABSTRACT

A system, including method and apparatus, for generating droplets suitable for droplet-based assays. The disclosed systems may include either one-piece or multi-piece droplet generation components configured to form sample-containing droplets by merging aqueous, sample-containing fluid with a background emulsion fluid such as oil, to form an emulsion of sample-containing droplets suspended in the background fluid. In some cases, the disclosed systems may include channels or other suitable mechanisms configured to transport the sample-containing droplets to an outlet region, so that subsequent assay steps may be performed.

8 Claims, 23 Drawing Sheets

Related U.S. Application Data continuation of application No. 16/160,783, filed on Oct. 15, 2018, now Pat. No. 10,272,432, which is a continuation of application No. 15/357,840, filed on Nov. 21, 2016, now Pat. No. 10,099,219, which is a continuation of application No. 13/341,669, filed on Dec. 30, 2011, now Pat. No. 9,500,664, which is a continuation of application No. PCT/US2011/030101, filed on Mar. 25, 2011.

(60) Provisional application No. 61/341,218, filed on Mar. 25, 2010.

(51) Int. Cl.
| | |
|---|---|
| *B01F 33/3011* | (2022.01) |
| *B01L 3/02* | (2006.01) |
| *B01L 7/00* | (2006.01) |
| *C12Q 1/6806* | (2018.01) |
| *G01N 35/00* | (2006.01) |
| *G01N 35/08* | (2006.01) |
| *G01N 35/10* | (2006.01) |

(52) U.S. Cl.
CPC ... *B01L 3/502715* (2013.01); *B01L 3/502723* (2013.01); *C12Q 1/6806* (2013.01); *G01N 35/085* (2013.01); *B01L 3/0275* (2013.01); *B01L 7/52* (2013.01); *B01L 2200/027* (2013.01); *B01L 2200/0689* (2013.01); *B01L 2300/0816* (2013.01); *B01L 2300/0829* (2013.01); *B01L 2300/0867* (2013.01); *B01L 2400/0487* (2013.01); *G01N 2035/00148* (2013.01); *G01N 2035/1034* (2013.01); *G01N 35/1065* (2013.01); *Y10T 29/494* (2015.01)

(58) Field of Classification Search
CPC ....... B01L 2200/027; B01L 2200/0689; B01L 2300/0816; B01L 2300/0829; B01L 2300/0867; B01L 2400/0487; G01N 35/1065; G01N 2035/00148; G01N 2035/1034; G01N 35/085; Y10T 29/494; C12Q 1/6806; B01F 23/41; B01F 33/3011

See application file for complete search history.

(56) References Cited

U.S. PATENT DOCUMENTS

| | | |
|---|---|---|
| 4,201,691 A | 5/1980 | Asher et al. |
| 4,283,262 A | 8/1981 | Cormier et al. |
| 4,348,111 A | 9/1982 | Goulas et al. |
| 4,636,075 A | 1/1987 | Knollenberg |
| 4,948,961 A | 8/1990 | Hillman et al. |
| 5,055,390 A | 10/1991 | Weaver et al. |
| 5,176,203 A | 1/1993 | Larzul |
| 5,225,332 A | 7/1993 | Weaver et al. |
| 5,270,183 A | 12/1993 | Corbett et al. |
| 5,314,809 A | 5/1994 | Erlich et al. |
| 5,344,930 A | 9/1994 | Riess et al. |
| 5,422,277 A | 6/1995 | Connelly et al. |
| 5,538,667 A | 7/1996 | Hill et al. |
| 5,555,191 A | 9/1996 | Hripcsak |
| 5,585,069 A | 12/1996 | Zanzucchi et al. |
| 5,587,128 A | 12/1996 | Wilding et al. |
| 5,602,756 A | 2/1997 | Atwood et al. |
| 5,720,923 A | 2/1998 | Haff et al. |
| 5,736,314 A | 4/1998 | Hayes et al. |
| 5,779,977 A | 7/1998 | Haff et al. |
| 5,827,480 A | 10/1998 | Haff et al. |
| 5,856,174 A | 1/1999 | Lipshutz et al. |
| 5,912,945 A | 6/1999 | Da Silva et al. |
| 5,928,907 A | 7/1999 | Woudenberg et al. |
| 5,945,334 A | 8/1999 | Besemer et al. |
| 5,972,716 A | 10/1999 | Ragusa et al. |
| 5,980,936 A | 11/1999 | Krafft et al. |
| 5,994,056 A | 11/1999 | Higuchi |
| 6,033,880 A | 3/2000 | Haff et al. |
| 6,042,709 A | 3/2000 | Parce et al. |
| 6,057,149 A | 5/2000 | Burns et al. |
| 6,123,798 A | 9/2000 | Gandhi et al. |
| 6,126,899 A | 10/2000 | Woudenberg et al. |
| 6,130,098 A | 10/2000 | Handique et al. |
| 6,143,496 A | 11/2000 | Brown et al. |
| 6,146,103 A | 11/2000 | Lee et al. |
| 6,171,785 B1 | 1/2001 | Higuchi |
| 6,175,669 B1 | 1/2001 | Colston et al. |
| 6,176,609 B1 | 1/2001 | Cleveland et al. |
| 6,176,962 B1 | 1/2001 | Soane et al. |
| 6,177,479 B1 | 1/2001 | Nakajima et al. |
| 6,210,879 B1 | 4/2001 | Meloni et al. |
| 6,258,569 B1 | 7/2001 | Livak et al. |
| 6,281,254 B1 | 8/2001 | Nakajima et al. |
| 6,303,343 B1 | 10/2001 | Kopf-Sill |
| 6,357,907 B1 | 3/2002 | Cleveland et al. |
| 6,384,915 B1 | 5/2002 | Everett et al. |
| 6,391,559 B1 | 5/2002 | Brown et al. |
| 6,440,706 B1 | 8/2002 | Vogelstein et al. |
| 6,466,713 B2 | 10/2002 | Everett et al. |
| 6,488,895 B1 | 12/2002 | Kennedy |
| 6,489,103 B1 | 12/2002 | Griffiths et al. |
| 6,494,104 B2 | 12/2002 | Kawakita et al. |
| 6,509,085 B1 | 1/2003 | Kennedy |
| 6,521,427 B1 | 2/2003 | Evans |
| 6,524,456 B1 | 2/2003 | Ramsey et al. |
| 6,540,895 B1 | 4/2003 | Spence et al. |
| 6,551,841 B1 | 4/2003 | Wilding et al. |
| 6,558,916 B2 | 5/2003 | Veerapandian et al. |
| 6,575,188 B2 | 6/2003 | Parunak |
| 6,602,472 B1 | 8/2003 | Zimmermann et al. |
| 6,620,625 B2 | 9/2003 | Wolk et al. |
| 6,637,463 B1 | 10/2003 | Lei et al. |
| 6,638,749 B1 | 10/2003 | Beckman et al. |
| 6,660,367 B1 | 12/2003 | Yang et al. |
| 6,663,619 B2 | 12/2003 | Odrich et al. |
| 6,664,044 B1 | 12/2003 | Sato |
| 6,670,153 B2 | 12/2003 | Stern |
| 6,753,147 B2 | 6/2004 | Vogelstein et al. |
| 6,767,706 B2 | 7/2004 | Quake et al. |
| 6,773,566 B2 | 8/2004 | Shenderov |
| 6,808,882 B2 | 10/2004 | Griffiths et al. |
| 6,814,934 B1 | 11/2004 | Higuchi |
| 6,833,242 B2 | 12/2004 | Quake et al. |
| 6,900,021 B1 | 5/2005 | Harrison et al. |
| 6,905,885 B2 | 6/2005 | Colston et al. |
| 6,915,679 B2 | 7/2005 | Chien et al. |
| 6,949,176 B2 | 9/2005 | Vacca et al. |
| 6,960,437 B2 | 11/2005 | Enzelberger et al. |
| 6,964,846 B1 | 11/2005 | Shuber |
| 7,010,391 B2 | 3/2006 | Handique et al. |
| 7,041,481 B2 | 5/2006 | Anderson et al. |
| 7,052,244 B2 | 5/2006 | Fouillet et al. |
| 7,060,227 B2 | 6/2006 | Staats |
| 7,081,336 B2 | 7/2006 | Bao et al. |
| 7,091,048 B2 | 8/2006 | Parce et al. |
| 7,094,379 B2 | 8/2006 | Fouillet et al. |
| 7,118,910 B2 | 10/2006 | Unger et al. |
| 7,129,091 B2 | 10/2006 | Ismagilov et al. |
| 7,138,233 B2 | 11/2006 | Griffiths et al. |
| 7,141,537 B2 | 11/2006 | Audenaert et al. |
| 7,192,557 B2 | 3/2007 | Wu et al. |
| 7,198,897 B2 | 4/2007 | Wangh et al. |
| 7,238,268 B2 | 7/2007 | Ramsey et al. |
| 7,244,567 B2 | 7/2007 | Chen et al. |
| 7,252,943 B2 | 8/2007 | Griffiths et al. |
| 7,268,167 B2 | 9/2007 | Higuchi et al. |
| 7,268,179 B2 | 9/2007 | Brown |
| 7,270,786 B2 | 9/2007 | Parunak et al. |
| 7,279,146 B2 | 10/2007 | Nassef et al. |
| 7,294,468 B2 | 11/2007 | Bell et al. |
| 7,294,503 B2 | 11/2007 | Quake et al. |
| 7,306,929 B2 | 12/2007 | Ignatov et al. |

(56) References Cited

U.S. PATENT DOCUMENTS

| | | |
|---|---|---|
| 7,312,085 B2 | 12/2007 | Chou et al. |
| 7,323,305 B2 | 1/2008 | Leamon et al. |
| 7,368,233 B2 | 5/2008 | Shuber et al. |
| 7,375,140 B2 | 5/2008 | Higuchi et al. |
| 7,423,751 B2 | 9/2008 | Hairston et al. |
| 7,429,467 B2 | 9/2008 | Holliger et al. |
| 7,567,596 B2 | 7/2009 | Dantus et al. |
| 7,579,172 B2 | 8/2009 | Cho et al. |
| 7,595,195 B2 | 9/2009 | Lee et al. |
| 7,622,280 B2 | 11/2009 | Holliger et al. |
| 7,629,123 B2 | 12/2009 | Millonig et al. |
| 7,776,927 B2 | 8/2010 | Chu et al. |
| 7,807,920 B2 | 10/2010 | Linke et al. |
| 7,842,457 B2 | 11/2010 | Berka et al. |
| 8,399,198 B2 | 3/2013 | Hiddessen et al. |
| 9,328,376 B2 | 5/2016 | Hiddessen et al. |
| 9,417,190 B2 | 8/2016 | Hindson et al. |
| 9,500,664 B2 | 11/2016 | Ness et al. |
| 2001/0046701 A1 | 11/2001 | Schulte et al. |
| 2002/0003001 A1 | 1/2002 | Weigl et al. |
| 2002/0021866 A1 | 2/2002 | Everett et al. |
| 2002/0022261 A1 | 2/2002 | Anderson et al. |
| 2002/0058332 A1 | 5/2002 | Quake et al. |
| 2002/0060156 A1 | 5/2002 | Mathies et al. |
| 2002/0068357 A1 | 6/2002 | Mathies et al. |
| 2002/0089561 A1 | 7/2002 | Weitzel et al. |
| 2002/0093655 A1 | 7/2002 | Everett et al. |
| 2002/0141903 A1 | 10/2002 | Parunak et al. |
| 2002/0142483 A1 | 10/2002 | Yao et al. |
| 2002/0151040 A1 | 10/2002 | O'Keefe et al. |
| 2002/0164820 A1 | 11/2002 | Brown |
| 2002/0195586 A1 | 12/2002 | Auslander et al. |
| 2003/0001121 A1 | 1/2003 | Hochstein |
| 2003/0003054 A1 | 1/2003 | McDonald et al. |
| 2003/0003441 A1 | 1/2003 | Colston et al. |
| 2003/0006140 A1 | 1/2003 | Vacca et al. |
| 2003/0008308 A1 | 1/2003 | Enzelberger et al. |
| 2003/0027150 A1 | 2/2003 | Katz |
| 2003/0027244 A1 | 2/2003 | Colston et al. |
| 2003/0027352 A1 | 2/2003 | Hooper et al. |
| 2003/0032172 A1 | 2/2003 | Colston, Jr. et al. |
| 2003/0049659 A1 | 3/2003 | Lapidus et al. |
| 2003/0087300 A1 | 5/2003 | Knapp et al. |
| 2003/0170698 A1 | 9/2003 | Gascoyne et al. |
| 2003/0180765 A1 | 9/2003 | Traverso et al. |
| 2003/0204130 A1 | 10/2003 | Colston, Jr. et al. |
| 2004/0007463 A1 | 1/2004 | Ramsey et al. |
| 2004/0037739 A1 | 2/2004 | McNeely et al. |
| 2004/0038385 A1 | 2/2004 | Langlois et al. |
| 2004/0067493 A1 | 4/2004 | Matsuzaki et al. |
| 2004/0068019 A1 | 4/2004 | Higuchi et al. |
| 2004/0074849 A1 | 4/2004 | Brown et al. |
| 2004/0090168 A1 | 5/2004 | Kumar et al. |
| 2004/0109793 A1 | 6/2004 | McNeely et al. |
| 2004/0171055 A1 | 9/2004 | Brown |
| 2004/0180346 A1 | 9/2004 | Anderson et al. |
| 2004/0208792 A1 | 10/2004 | Linton et al. |
| 2004/0228770 A1 | 11/2004 | Gandhi et al. |
| 2005/0036920 A1 | 2/2005 | Gilbert |
| 2005/0042639 A1 | 2/2005 | Knapp et al. |
| 2005/0064460 A1 | 3/2005 | Holliger et al. |
| 2005/0079510 A1 | 4/2005 | Berka et al. |
| 2005/0112541 A1 | 5/2005 | Durack et al. |
| 2005/0172476 A1 | 8/2005 | Stone et al. |
| 2005/0202429 A1 | 9/2005 | Trau et al. |
| 2005/0202489 A1* | 9/2005 | Cho .................. B01F 25/433 435/6.12 |
| 2005/0221279 A1 | 10/2005 | Carter et al. |
| 2005/0221373 A1 | 10/2005 | Enzelberger et al. |
| 2005/0227264 A1* | 10/2005 | Nobile ............... B01F 25/314 435/6.16 |
| 2005/0239192 A1 | 10/2005 | Nasarabadi et al. |
| 2005/0266582 A1 | 12/2005 | Modlin et al. |
| 2005/0277125 A1 | 12/2005 | Benn et al. |
| 2005/0282206 A1 | 12/2005 | Michael Corbett et al. |
| 2006/0014187 A1 | 1/2006 | Li et al. |
| 2006/0024831 A1 | 2/2006 | Kao et al. |
| 2006/0057599 A1 | 3/2006 | Dzenitis et al. |
| 2006/0077755 A1 | 4/2006 | Higuchi et al. |
| 2006/0079583 A1 | 4/2006 | Higuchi et al. |
| 2006/0079584 A1 | 4/2006 | Higuchi et al. |
| 2006/0079585 A1 | 4/2006 | Higuchi et al. |
| 2006/0094108 A1 | 5/2006 | Yoder et al. |
| 2006/0106208 A1 | 5/2006 | Nochumson et al. |
| 2006/0188463 A1 | 8/2006 | Kim et al. |
| 2006/0234298 A1 | 10/2006 | Chiu et al. |
| 2006/0257992 A1* | 11/2006 | McDevitt .............. B01L 9/527 435/287.2 |
| 2007/0003442 A1 | 1/2007 | Link et al. |
| 2007/0010974 A1 | 1/2007 | Nicoli et al. |
| 2007/0039866 A1 | 2/2007 | Schroeder et al. |
| 2007/0048756 A1 | 3/2007 | Mei et al. |
| 2007/0054119 A1 | 3/2007 | Garstecki et al. |
| 2007/0109542 A1 | 5/2007 | Tracy et al. |
| 2007/0166200 A1 | 7/2007 | Zhou et al. |
| 2007/0195127 A1 | 8/2007 | Ahn et al. |
| 2007/0196397 A1 | 8/2007 | Torii et al. |
| 2007/0202525 A1 | 8/2007 | Quake et al. |
| 2007/0231393 A1 | 10/2007 | Ritter et al. |
| 2007/0242111 A1 | 10/2007 | Pamula et al. |
| 2007/0248956 A1 | 10/2007 | Buxbaum et al. |
| 2007/0253868 A1 | 11/2007 | Beebe et al. |
| 2007/0258083 A1 | 11/2007 | Heppell et al. |
| 2007/0275415 A1 | 11/2007 | Srinivasan et al. |
| 2008/0003142 A1 | 1/2008 | Link et al. |
| 2008/0014589 A1 | 1/2008 | Link et al. |
| 2008/0038810 A1 | 2/2008 | Pollack et al. |
| 2008/0056948 A1 | 3/2008 | Dale et al. |
| 2008/0070862 A1 | 3/2008 | Laster et al. |
| 2008/0090244 A1 | 4/2008 | Knapp et al. |
| 2008/0138815 A1 | 6/2008 | Brown et al. |
| 2008/0145923 A1 | 6/2008 | Hahn et al. |
| 2008/0153091 A1 | 6/2008 | Brown et al. |
| 2008/0160525 A1 | 7/2008 | Brown et al. |
| 2008/0161420 A1 | 7/2008 | Shuber |
| 2008/0166720 A1 | 7/2008 | Hsieh et al. |
| 2008/0166793 A1 | 7/2008 | Beer et al. |
| 2008/0169184 A1 | 7/2008 | Brown et al. |
| 2008/0169195 A1 | 7/2008 | Jones et al. |
| 2008/0171324 A1 | 7/2008 | Brown et al. |
| 2008/0171325 A1 | 7/2008 | Brown et al. |
| 2008/0171326 A1 | 7/2008 | Brown et al. |
| 2008/0171327 A1 | 7/2008 | Brown et al. |
| 2008/0171380 A1 | 7/2008 | Brown et al. |
| 2008/0171382 A1 | 7/2008 | Brown et al. |
| 2008/0213766 A1 | 9/2008 | Brown et al. |
| 2008/0214407 A1 | 9/2008 | Remacle et al. |
| 2008/0223721 A1 | 9/2008 | Cohen et al. |
| 2008/0241841 A1 | 10/2008 | Murakawa et al. |
| 2008/0241962 A1* | 10/2008 | Wang ............... G01N 33/54386 436/514 |
| 2008/0257438 A1 | 10/2008 | Wang et al. |
| 2008/0262384 A1 | 10/2008 | Wiederkehr et al. |
| 2008/0268436 A1 | 10/2008 | Duan et al. |
| 2008/0274455 A1 | 11/2008 | Puskas et al. |
| 2008/0280331 A1 | 11/2008 | Davies et al. |
| 2008/0280865 A1 | 11/2008 | Tobita |
| 2008/0280955 A1 | 11/2008 | McCamish |
| 2008/0314761 A1 | 12/2008 | Herminghaus et al. |
| 2009/0012187 A1 | 1/2009 | Chu et al. |
| 2009/0026082 A1 | 1/2009 | Rothberg et al. |
| 2009/0029867 A1 | 1/2009 | Reed et al. |
| 2009/0035770 A1 | 2/2009 | Mathies et al. |
| 2009/0035838 A1 | 2/2009 | Quake et al. |
| 2009/0047713 A1 | 2/2009 | Handique |
| 2009/0061428 A1 | 3/2009 | McBride et al. |
| 2009/0068170 A1 | 3/2009 | Weitz et al. |
| 2009/0069194 A1 | 3/2009 | Ramakrishnan |
| 2009/0098044 A1 | 4/2009 | Kong et al. |
| 2009/0114043 A1 | 5/2009 | Cox |
| 2009/0131543 A1 | 5/2009 | Weitz et al. |
| 2009/0162929 A1 | 6/2009 | Ikeda |
| 2009/0176271 A1 | 7/2009 | Durack et al. |
| 2009/0203063 A1 | 8/2009 | Wheeler et al. |

(56) References Cited

U.S. PATENT DOCUMENTS

| | | |
|---|---|---|
| 2009/0217742 A1 | 9/2009 | Chiu et al. |
| 2009/0220434 A1 | 9/2009 | Sharma |
| 2009/0235990 A1 | 9/2009 | Beer |
| 2009/0239308 A1 | 9/2009 | Dube et al. |
| 2009/0269248 A1 | 10/2009 | Falb et al. |
| 2009/0291435 A1 | 11/2009 | Unger et al. |
| 2009/0311713 A1 | 12/2009 | Pollack et al. |
| 2009/0325184 A1 | 12/2009 | Woudenberg et al. |
| 2009/0325234 A1 | 12/2009 | Gregg et al. |
| 2009/0325236 A1 | 12/2009 | Griffiths et al. |
| 2010/0009360 A1 | 1/2010 | Rosell Costa et al. |
| 2010/0015606 A1 | 1/2010 | Davies et al. |
| 2010/0018584 A1 | 1/2010 | Bransky |
| 2010/0020565 A1 | 1/2010 | Seward |
| 2010/0022414 A1 | 1/2010 | Link et al. |
| 2010/0022680 A1 | 1/2010 | Karnik et al. |
| 2010/0041046 A1 | 2/2010 | Chiu et al. |
| 2010/0047808 A1 | 2/2010 | Reed et al. |
| 2010/0069250 A1 | 3/2010 | White, III et al. |
| 2010/0069263 A1 | 3/2010 | Shendure et al. |
| 2010/0092973 A1 | 4/2010 | Davies et al. |
| 2010/0137163 A1 | 6/2010 | Link et al. |
| 2010/0173394 A1 | 7/2010 | Colston, Jr. et al. |
| 2010/0184928 A1 | 7/2010 | Kumacheva |
| 2010/0217736 A1 | 8/2010 | Sarel |
| 2010/0248385 A1 | 9/2010 | Tan et al. |
| 2010/0261229 A1 | 10/2010 | Lau et al. |
| 2010/0304446 A1 | 12/2010 | Davies et al. |
| 2010/0304978 A1 | 12/2010 | Deng et al. |
| 2011/0000560 A1 | 1/2011 | Miller et al. |
| 2011/0027394 A1 | 2/2011 | McClements et al. |
| 2011/0053798 A1 | 3/2011 | Hindson et al. |
| 2011/0070589 A1 | 3/2011 | Belgrader et al. |
| 2011/0086780 A1 | 4/2011 | Colston, Jr. et al. |
| 2011/0092373 A1 | 4/2011 | Colston, Jr. et al. |
| 2011/0092376 A1 | 4/2011 | Colston, Jr. et al. |
| 2011/0092392 A1 | 4/2011 | Colston, Jr. et al. |
| 2011/0118151 A1 | 5/2011 | Eshoo et al. |
| 2011/0160078 A1 | 6/2011 | Fodor et al. |
| 2011/0177563 A1 | 7/2011 | Hahn et al. |
| 2011/0183330 A1 | 7/2011 | Lo et al. |
| 2011/0212516 A1 | 9/2011 | Ness et al. |
| 2011/0217712 A1 | 9/2011 | Hiddessen et al. |
| 2011/0217736 A1 | 9/2011 | Hindson |
| 2011/0218123 A1 | 9/2011 | Weitz et al. |
| 2011/0244455 A1 | 10/2011 | Larson et al. |
| 2011/0250597 A1 | 10/2011 | Larson et al. |
| 2011/0311978 A1 | 12/2011 | Makarewicz, Jr. et al. |
| 2012/0003755 A1 | 1/2012 | Chapin et al. |
| 2012/0021423 A1 | 1/2012 | Colston, Jr. et al. |
| 2012/0028311 A1 | 2/2012 | Colston, Jr. et al. |
| 2012/0122714 A1 | 5/2012 | Samuels et al. |
| 2012/0152369 A1 | 6/2012 | Hiddessen et al. |
| 2012/0171683 A1 | 7/2012 | Ness et al. |
| 2012/0190033 A1 | 7/2012 | Ness et al. |
| 2012/0194805 A1 | 8/2012 | Ness et al. |
| 2012/0208241 A1 | 8/2012 | Link |
| 2012/0219947 A1 | 8/2012 | Yurkovetsky et al. |
| 2012/0220494 A1 | 8/2012 | Samuels et al. |
| 2012/0264646 A1 | 10/2012 | Link et al. |
| 2012/0302448 A1 | 11/2012 | Hutchison et al. |
| 2012/0309002 A1 | 12/2012 | Link |
| 2012/0329664 A1 | 12/2012 | Saxonov et al. |
| 2013/0017551 A1 | 1/2013 | Dube |
| 2013/0040841 A1 | 2/2013 | Saxonov et al. |
| 2013/0045875 A1 | 2/2013 | Saxonov et al. |
| 2013/0059754 A1 | 3/2013 | Tzonev |
| 2013/0064776 A1 | 3/2013 | El Harrak et al. |
| 2013/0084572 A1 | 4/2013 | Hindson et al. |
| 2013/0099018 A1 | 4/2013 | Miller et al. |
| 2013/0109575 A1 | 5/2013 | Kleinschmidt et al. |
| 2017/0065979 A1 | 3/2017 | Ness et al. |
| 2017/0144116 A1 | 5/2017 | Ness et al. |
| 2017/0144160 A1 | 5/2017 | Ness et al. |
| 2017/0144161 A1 | 5/2017 | Hindson et al. |

FOREIGN PATENT DOCUMENTS

| | | |
|---|---|---|
| EP | 1522582 A2 | 4/2005 |
| EP | 1677094 | 7/2006 |
| EP | 1522582 B1 | 4/2007 |
| GB | 1503163 | 3/1978 |
| GB | 2097692 | 11/1982 |
| JP | 0295433 | 4/1990 |
| JP | 08035971 | 2/1996 |
| JP | 2002505439 | 2/2002 |
| JP | 2006180810 | 7/2006 |
| JP | 2007175002 | 7/2007 |
| JP | 2009536313 | 10/2009 |
| JP | 2009538123 | 11/2009 |
| JP | 2010506136 | 2/2010 |
| WO | 82/02562 | 8/1982 |
| WO | 84/02000 | 5/1984 |
| WO | 92/01812 | 2/1992 |
| WO | 94/05414 | 3/1994 |
| WO | 96/12194 | 4/1996 |
| WO | 98/00231 | 1/1998 |
| WO | 98/16313 | 4/1998 |
| WO | 98/44151 | 10/1998 |
| WO | 98/44152 | 10/1998 |
| WO | 98/47003 | 10/1998 |
| WO | 9944740 | 9/1999 |
| WO | 0078455 | 12/2000 |
| WO | 01/07159 | 2/2001 |
| WO | 01/12327 | 2/2001 |
| WO | 02/23163 | 3/2002 |
| WO | 02/060584 | 8/2002 |
| WO | 02063288 | 8/2002 |
| WO | 02/068104 | 9/2002 |
| WO | 02/081490 | 10/2002 |
| WO | 02/081729 | 10/2002 |
| WO | 03/016558 | 2/2003 |
| WO | 03/042410 | 5/2003 |
| WO | 03052428 | 6/2003 |
| WO | 03/072258 | 9/2003 |
| WO | 2004/040001 | 5/2004 |
| WO | 2005/007812 | 1/2005 |
| WO | 2005/010145 | 2/2005 |
| WO | 2005/021151 | 3/2005 |
| WO | 2005/023091 | 3/2005 |
| WO | 2005/055807 | 6/2005 |
| WO | 2005/073410 | 8/2005 |
| WO | 2005/075683 | 8/2005 |
| WO | 2006/023719 | 3/2006 |
| WO | 2006/027757 | 3/2006 |
| WO | 2006/038035 | 4/2006 |
| WO | 2006/086777 | 8/2006 |
| WO | 2006/095981 | 9/2006 |
| WO | 2006128098 | 11/2006 |
| WO | 2007081385 | 7/2007 |
| WO | 2007/091228 | 8/2007 |
| WO | 2007/091230 | 8/2007 |
| WO | 2007/092473 | 8/2007 |
| WO | 2007121489 | 10/2007 |
| WO | 2007/133710 | 11/2007 |
| WO | 2008/021123 | 2/2008 |
| WO | 2008/024114 | 2/2008 |
| WO | 2008/063227 | 5/2008 |
| WO | 2008/070074 | 6/2008 |
| WO | 2008/070862 | 6/2008 |
| WO | 2008/109176 | 9/2008 |
| WO | 2008/109878 | 9/2008 |
| WO | 2008/112177 | 9/2008 |
| WO | 2008/148200 | 12/2008 |
| WO | 2009/002920 | 12/2008 |
| WO | 2009/015863 | 2/2009 |
| WO | 2009/049889 | 4/2009 |
| WO | 2009/085246 | 7/2009 |
| WO | 2009152520 | 12/2009 |
| WO | 2010/001419 | 1/2010 |
| WO | 2010/018465 | 2/2010 |
| WO | 2010036352 | 4/2010 |

(56) References Cited

FOREIGN PATENT DOCUMENTS

| | | |
|---|---|---|
| WO | 2011/034621 | 3/2011 |
| WO | 2011/079176 | 6/2011 |

OTHER PUBLICATIONS

3M Specialty Materials, "3M Fluorinert Electronic Liquid FC-3283," product information guide, issued Aug. 2001.

Abate, Adam R. et al., "Functionalized glass coating for PDMS microfluidic devices," Lab on a Chip Technology: Fabrication and Microfluidics, 11 pgs., (2009).

Abdelgawad, Mohamed et al., "All-terrain droplet actuation," Lab on a Chip, vol. 8, pp. 672-677, Apr. 2, 2008.

Alexandridis, Paschalis, Structural Polymorphism of Poly(ethylene oxide)-Poly(propylene oxide) Block Copolymers in Nonaqueous Polar Solvents, Macromolecules, vol. 31, No. 20, pp. 6935-6942, Sep. 12, 1998.

Anna, Shelley L. et al., "Formation of dispersions using "flow focusing" in microchannels," Applied Physics Letters, vol. 82, No. 3, Jan. 20, 2003.

Avilion, Ariel A. et al., "Human Telomerase RNA and Telomerase Activity in Immortal Cell Lines and Tumor Tissues," Cancer Research 56, pp. 645-650, Feb. 1, 1996.

The International Bureau of WIPO, "International Preliminary Report on Patentability" in connection with related International App. No. PCT/US2011/030101, dated Sep. 25, 2012, 7 pgs.

Becker, Holger et al., "Polymer microfabrication technologies for microfluidic systems", Analytical and Bioanalytical Chemistry, vol. 390, Nov. 8, 2007, pp. 89-111.

Beer, N. Reginald et al., "On-Chip Single-Copy Real-Time Reverse-Transcription PCR in Isolated Picoliter Droplets," Analytical Chemistry, vol. 80, No. 6, pp. 1854-1858, Mar. 15, 2008.

Beer, N. Reginald et al., "On-Chip, Real-Time, Single-Coy Polymerase Chain Reaction in Picoliter Droplets," Analytical Chemistry, vol. 79, No. 22, pp. 8471-8475, Nov. 15, 2007.

Beer, Neil Reginald et al., "Monodisperse droplet generation and rapid trapping for single molecule detection and reaction kinetics measurement," Lab on a Chip, vol. 9, pp. 841-844, Dec. 5, 2008.

Bernoulli Pressure Lowering, http:\hyperphysics, pp. 1-4, included as an exhibit in IPR2018-00300, IPR2018-00301 and IPR2018-00302 Petitions filed Dec. 14, 2017 and IPR2018-00432, IPR2018-00433 and IPR2018-00434 Petitions filed Jan. 9, 2018, 4 pgs.

Bhat, Somanath et al., "Effect of sustained elevated temperature prior to amplification on template copy number estimation using digital polymerase chain reaction," Analyst, vol. 136, pp. 724-732, (2011).

Blow, Nathan, "PCR's next frontier," Nature Methods, vol. 4, No. 10, pp. 869-875, Oct. 2007.

Bransky, Avishay et al., "A microfluidic droplet generator based on a piezoelectric actuator," Lab on a Chip, vol. 9, pp. 516-520, Nov. 20, 2008.

Brody, James P. et al., "Biotechnology at Low Reynolds Numbers", Biophysical Journal. vol. 71, Dec. 1996, pp. 3430-3441.

Carroll, Nick J. et al., "Droplet-Based Microfluidics for Emulsion and Solvent Evaporation Synthesis of Monodisperse Mesoporous Silica Microspheres," Langmuir, vol. 24, No. 3, pp. 658-661, Jan. 3, 2008.

Cawthon, Richard M., "Telomere length measurement by a novel monochrome multiplex quantitative PCR method," Nucleic Acids Research, vol. 37, No. 3, pp. 1-7, (2009).

Cawthon, Richard M., "Telomere measurement by quantitative PCR," Nucleic Acids Research, vol. 30, No. 10, pp. 1-6, (2002).

Chabert, Max et al., "Droplet fusion by alternating current (AC) field electrocoalescence in microchannels," Electrophoresis, vol. 26, pp. 3706-3715, (2005).

Charles N. Baroud et al., "Thermocapillary valve for droplet production and sorting," Physical Review E 75, 046302, pp. 046302-1-046302-5, Apr. 5, 2007.

Chen, Chia-Hung et al., "Janus Particles Templated from Double Emulsion Droplets Generated Using Microfluidics," Langmuir, vol. 29, No. 8, pp. 4320-4323, Mar. 18, 2009.

Chen, Delai L. et al., "Using Three-Phase Flow of Immiscible Liquids to Prevent Coalescence of Droplets in Microfluidic Channels: Criteria to Identify the Third Liquid and Validation with Protein Crystallization," Langmuir, vol. 23, No. 4, pp. 2255-2260, (2007).

Chien, Ring-Ling et al., "Multiport flow-control system for lab-on-a-chip microfluidic devices", Fresenius Journal of Analytical Chemistry, vol. 371, Jul. 27, 2001, pp. 106-111.

Chittofrati, A. et al., "Perfluoropolyether microemulsions," Progress in Colloid & Polymer Science 79, pp. 218-225, (1989).

Chloroform (Phenomenex), Solvent Miscibility Table, Internet Archive WayBackMachine, 3 pgs., Feb. 1, 2008.

Clausell-Tormos, Jenifer et al., "Droplet-Based Microfluidic Platforms for the Encapsulation and Screening of Mammalian Cells and Multicellular Organisms," Chemistry & Biology, vol. 15, pp. 427-437, May 2008.

Complainant Ground Rule 4 Notice of Patent Priority Dates, Dates of Conception, and Dates of Reduction to Practice, in the matter of Certain Microfluidic Devices, United States International Trade Commission Investigation No. 337-TA-1068, filed Nov. 17, 2017, included as Exhibit in IPR2018-00300 Petition filed Dec. 14, 2017, 4 pgs.

Complainant Ground Rule 4 Notice of Patent Priority Dates, Dates of Conception, and Dates of Reduction to Practice, in the matter of Certain Microfluidic Devices, United States International Trade Commission Investigation No. 337-TA-1068, filed Nov. 17, 2017, included as Exhibit in IPR2018-00301 Petition filed Dec. 14, 2017, 4 pgs.

Complainant Ground Rule 4 Notice of Patent Priority Dates, Dates of Conception, and Dates of Reduction to Practice, in the matter of Certain Microfluidic Devices, United States International Trade Commission Investigation No. 337-TA-1068, filed Nov. 17, 2017, included as Exhibit in IPR2018-00302 Petition filed Dec. 14, 2017, 4 pgs.

Complainant Ground Rule 4 Notice of Patent Priority Dates, Dates of Conception, and Dates of Reduction to Practice, in the matter of Certain Microfluidic Devices, United States International Trade Commission Investigation No. 337-TA-1068, filed Nov. 17, 2017, included as Exhibit in IPR2018-00432 Petition filed Jan. 9, 2018, 4 pgs.

Complainant Ground Rule 4 Notice of Patent Priority Dates, Dates of Conception, and Dates of Reduction to Practice, in the matter of Certain Microfluidic Devices, United States International Trade Commission Investigation No. 337-TA-1068, filed Nov. 17, 2017, included as Exhibit in IPR2018-00433 Petition filed Jan. 9, 2018, 4 pgs.

Complainant Ground Rule 4 Notice of Patent Priority Dates, Dates of Conception, and Dates of Reduction to Practice, in the matter of Certain Microfluidic Devices, United States International Trade Commission Investigation No. 337-TA-1068, filed Nov. 17, 2017, included as Exhibit in IPR2018-00434 Petition filed Jan. 9, 2018, 4 pgs.

Complainant Ground Rule 4 Notice of Patent Priority Dates, Dates of Conception, and Dates of Reduction to Practice, in the matter of Certain Microfluidic Devices, United States International Trade Commission Investigation No. 337-TA-1068, filed Nov. 17, 2017, included as Exhibit in IPR2018-00489 Petition filed Jan. 15, 2018, 4 pgs.

Complainant Ground Rule 4 Notice of Patent Priority Dates, Dates of Conception, and Dates of Reduction to Practice, in the matter of Certain Microfluidic Devices, United States International Trade Commission Investigation No. 337-TA-1068, filed Nov. 17, 2017, included as Exhibit in IPR2018-00490 Petition filed Jan. 15, 2018, 4 pgs.

Da Rocha, Sandro R. P. et al., "Effect of Surfactants on the Interfacial Tension and Emulsion Formation between Water and Carbon Dioxide," Langmuir, vol. 15, No. 2, pp. 419-428, (1999), published on web Dec. 29, 1998.

(56) References Cited

OTHER PUBLICATIONS

Dasgupta, Purnendu K. et al., "Light emitting diode-based detectors Absorbance, fluorescence and spectroelectrochemical measurements in a planar flow-through cell," Analytica Chimica Acta 500, pp. 337-364, (2003).
De Mello, Andrew J. et al., "Chip technology for micro-separation", BioMethods, vol. 10, (1999), pp. 129-177.
Diehl, Frank et al., "Digital quantification of mutant DNA in cancer patients," Current Opinion in Oncology, vol. 19, pp. 36-42, (2007).
Diekema, Daniel J. et al., "Look before You Leap: Active Surveillance for Multidrug-Resistant Organisms," Healthcare Epidemiology • CID 2007:44, pp. 1101-1107 (Apr. 15), electronically published Mar. 2, 2007.
Ding, Chunming et al., "Direct molecular haplotyping of long-range genomic DNA with MI-PCR," PNAS, vol. 100, No. 13, pp. 7449-7453, Jun. 24, 2003.
Dorfman, Kevin D. et al., "Contamination-Free Continuous Flow Microfluidic Polymerase Chain Reaction for Quantitative and Clinical Applications," Analytical Chemistry vol. 77, No. 11, pp. 3700-3704, Jun. 1, 2005.
Dressman, Devin et al., "Transforming single DNA molecules into fluorescent magnetic particles for detection and enumeration of genetic variations," PNAS, vol. 100, No. 15, Jul. 22, 2003.
Dube, Simant et al., "Mathematical Analysis of Copy Number Variation in a DNA Sample Using Digital PCR on a Nanofluidic Device," PLoS ONE, vol. 3, Issue 8, pp. 1-9, Aug. 6, 2008.
Duffy, David C. et al., Rapid Prototyping of Microfluidic Systems in Poly(dimethylsiloxane), Analytical Chemistry, vol. 70, No. 23, Dec. 1, 1998, pp. 4974-4984.
Edgar, J. Scott et al., "Capillary Electrophoresis Separation in the Presence of an Immiscible Boundary for Droplet Analysis", Analytical Chemistry, vol. 78, No. 19, Oct. 1, 2006, pp. 6948-6954.
Emerson, David et al., "Microfluidic Modelling Activities at C3M," Centre for Microfluidics & Microsystems Modelling, Daresbury Laboratory, pp. 1-26, May 15, 2006.
Eschenback Optik GMBH, Optics for Concentrated Photovoltaics (CPV), 1 pg., date unknown.
Falb, Peter W. et al., U.S. Appl. No. 61/047,377, filed Apr. 23, 2008, included as an exhibit in IPR2018-00300, IPR2018-00301 and IPR2018-00302 Petitions filed Dec. 14, 2017 and IPR2018-00432, IPR2018-00433 and IPR2018-00434 Petitions filed Jan. 9, 2018, 75 pgs.
Fan, Jian-Bing et al., "Highly parallel genomic assays," Nature Reviews/Genetics, vol. 7, pp. 632-644, Aug. 2006.
Fidalgo, Luis M. et al., "Coupling Microdroplet Microreactors with Mass Spectrometry: Reading the Contents of Single Droplets Online," Angewandte Chemie, vol. 48, pp. 3665-3668, Apr. 7, 2009.
Fielden, Peter et al., "Micro-Droplet Technology for High Throughout Systems and Methods," 1 pg., Mar. 8, 2006.
Galambos, Paul et al., "Precision Alignment Packaging for Microsystems with Multiple Fluid Connections", Proceedings of 2001 ASME: International Mechanical Engineering Conference and Exposition, Nov. 11-16, 2001 New York, NY, 8 pgs.
Garstecki, Piotr et al., "Formation of droplets and bubbles in a microfluidic T-junction—scaling and mechanism of break-up," Lab on a Chip, vol. 6, pp. 437-446, (2006).
Garstecki, Piotr et al., "Mechanism for Flow-Rate Controlled Breakup in Confined Geometries: A Route to Monodisperse Emulsions," Physical Review Letters, 164501, pp. 164501-1-164501-4, Apr. 29, 2005.
Garti, N. et al., "Water Solubilization in Nonionic Microemulsions Stabilized by Grafted Siliconic Emulsifiers," Journal of Colloid and Interface Science vol. 233, pp. 286-294, (2001).
Gasperlin, M. et al., "The structure elucidation of semisolid w/o emulsion systems containing silicone surfactant," International Journal of Pharmaceutics 107, pp. 51-56, (1994).
Ge, Qinyu et al., "Emulsion PCR-based method to detect Y chromosome microdeletions," Analytical Biochemistry, vol. 367, pp. 173-178, May 10, 2007.
Ghenciu, E. G. et al., "Affinity Extraction into Carbon Dioxide. 1. Extraction of Avidin Using a Biotin-Functional Fluoroether Surfactant," Ind. Eng. Chem. Res. vol. 36, No. 12, pp. 5366-5370, Dec. 1, 1997.
The International Bureau of WIPO, "International Preliminary Report on Patentability" in connection with related International Application No. PCT/US2009/005317, dated Mar. 29, 2011, 8 pgs.
Glotsos, Dimitris et al., "Robust Estimation of Bioaffinity Assay Fluorescence Signals," IEEE Transactions on Information Technology in Biomedicine, vol. 10, No. 4, pp. 733-739, Oct. 2006.
Goldschmidt GMBH, "Abil® EM 90 Emulsifier for the formulation of cosmetic W/O creams and lotions," degussa. creating essentials brochure, pp. 1-7, May 2003.
Griffiths, Andrew D. et al., "Miniaturising the laboratory in emulsion droplets," Trends in Biotechnology, vol. 24, No. 9, pp. 395-402, Jul. 14, 2006.
Gullberg, Mats et al., "Cytokine detection by antibody-based proximity ligation," PNAS, vol. 101, No. 22, pp. 8420-8424, Jun. 1, 2004.
Guo, Zhen et al., "Enhanced discrimination of single nucleotide polymorphisms by artificial mismatch hybridization," Nature Biotechnology vol. 15, pp. 331-335, Apr. 1997.
Gustafsdottir, Sigrun et al., "In vitro analysis of DNA-protein interactions by proximity ligation," PNAS, vol. 104, No. 9, pp. 3067-3072, Feb. 27, 2007.
Higuchi, Russell et al., "Kinetic PCR Analysis: Real-time Monitoring of DNA Amplification Reactions," Bio/Technology vol. II, pp. 1026-1030, Sep. 11, 1993.
Hill, Randla M., "Silicone surfactants—new developments," Current Opinion in Colloid & Interface Science 7, pp. 255-261, (2002).
Hobbs, Helen R. et al., "Homogeneous Biocatalysis in both Fluorous Biphasic and Supercritical Carbon Dioxide Systems," Angewandte Chemie, vol. 119, pp. 8006-8009, Sep. 6, 2007.
Holtze, C. et al., "Biocompatible surfactants for water-in-fluorocarbon emulsions," Lab on a Chip, vol. 8, pp. 1632-1639, Sep. 2, 2008.
Hori, Machiko et al., "Uniform amplification of multiple DNAs by emulsion PCR," Biochemical and Biophysical Research Communications, vol. 352, pp. 323-328, (2007).
Huang, Jiaqi et al., "Rapid Screening of Complex DNA Samples by Single-Molecule Amplification and Sequencing," PLoS ONE, vol. 6, Issue 5, pp. 1-4, May 2011.
Hung, Lung-Hsin et al., "Rapid microfabrication of solvent-resistant biocompatible microfluidic devices," Lab on a Chip, vol. 8, pp. 983-987, Apr. 8, 2008.
IPR2018-00300 Petition for Inter Partes Review filed by 10X Genomics, Inc. on Dec. 14, 2017 before the Patent Trial and Appeal Board, including Declaration of Dr. Khushroo Gandhi (Exhibit 1003); Curriculum Vitae of Dr. Khushroo Gandhi (Exhibit 1045) and Declaration of Ruth G. Davila (Exhibit 1049), 235 pgs.
IPR2018-00301 Petition for Inter Partes Review filed by 10X Genomics, Inc. on Dec. 14, 2017 before the Patent Trial and Appeal Board, including Declaration of Dr. Khushroo Gandhi (Exhibit 1003); Curriculum Vitae of Dr. Khushroo Gandhi (Exhibit 1039) and Declaration of Ruth G. Davila (Exhibit 1044), 246 pgs.
IPR2018-00302 Petition for Inter Partes Review filed by 10X Genomics, Inc. on Dec. 14, 2017 before the Patent Trial and Appeal Board, including Declaration of Dr. Khushroo Gandhi (Exhibit 1003); Curriculum Vitae of Dr. Khushroo Gandhi (Exhibit 1039) and Declaration of Ruth G. Davila (Exhibit 1044), 223 pgs.
IPR2018-00432 Petition for Inter Partes Review filed by 10X Genomics, Inc. on Jan. 9, 2018 before the Patent Trial and Appeal Board, including Declaration of Dr. Khushroo Gandhi (Exhibit 1003); Curriculum Vitae of Dr. Khushroo Gandhi (Exhibit 1039) and Declaration of Ruth G. Davila (Exhibit 1049), 241 pgs.
IPR2018-00433 Petition for Inter Partes Review filed by 10X Genomics, Inc. on Jan. 9, 2018 before the Patent Trial and Appeal Board, including Declaration of Dr. Khushroo Gandhi (Exhibit 1003); Curriculum Vitae of Dr. Khushroo Gandhi (Exhibit 1039) and Declaration of Ruth G. Davila (Exhibit 1044), 246 pgs.
IPR2018-00434 Petition for Inter Partes Review filed by 10X Genomics, Inc. on Jan. 9, 2018 before the Patent Trial and Appeal Board, including Declaration of Dr. Khushroo Gandhi (Exhibit

(56) References Cited

OTHER PUBLICATIONS

1003); Curriculum Vitae of Dr. Khushroo Gandhi (Exhibit 1039) and Declaration of Ruth G. Davila (Exhibit 1044), 225 pgs.
IPR2018-00489 Petition for Inter Partes Review filed by 10X Genomics, Inc. on Jan. 15, 2018 before the Patent Trial and Appeal Board, including Declaration of Dr. Khushroo Gandhi (Exhibit 1003); Curriculum Vitae of Dr. Khushroo Gandhi (Exhibit 1045) and Declaration of Ruth G. Davila (Exhibit 1049), 240 pgs.
IPR2018-00490 Petition for Inter Partes Review filed by 10X Genomics, Inc. on Jan. 15, 2018 before the Patent Trial and Appeal Board, including Declaration of Dr. Khushroo Gandhi (Exhibit 1003); Curriculum Vitae of Dr. Khushroo Gandhi (Exhibit 1039) and Declaration of Ruth G. Davila (Exhibit 1044), 243 pgs.
Jarvius, Jonas et al., "Digital quantification using amplified single-molecule detection," Nature Methods, vol. 3, No. 9, pp. 15 pgs, Sep. 2006.
Jin, Dayong et al., "Practical Time-Gated Luminescence Flow Cytometry. II: Experimental Evaluation Using UV LED Excitation," Cytometry Part A • 71A, pp. 797-808, Aug. 24, 2007.
Kalinina, Olga et al., "Nanoliter scale PCR with TaqMan Detection," Nucleic Acids Research, vol. 25, No. 10 pp. 1999-2004, (1997).
Katsura, Shinji et al., "Indirect micromanipulation of single molecules in water-in-oil emulsion," Electrophoresis, vol. 22, pp. 289-293, (2001).
Kawai, A. et al., "Mass-Production System of Nearly Monodisperse Diameter Gel Particles Using Droplets Formation in a Microchannel", Micro Total Analysis Systems, vol. 1, 2002, pp. 368-370.
Kekevi, Burcu et al., Synthesis and Characterization of Silicone-Based Surfactants as Anti-Foaming Agents, J. Surfact Deterg (2012), vol. 15, pp. 73-81, published online Jul. 7, 2011.
Kojima, Takaaki et al., "PCR amplification from single DNA molecules on magnetic beads in emulsion: application for high-throughput screening of transcription factor targets," Nucleic Acids Research, vol. 33, No. 17, pp. 1-9, (2005).
Kumacheva, Eugenia, U.S. Appl. No. 60/924,921, filed Jun. 5, 2007, included as an exhibit in IPR2018-00300, IPR2018-00301 and IPR2018-00302 Petitions filed Dec. 14, 2017 and IPR2018-00432, IPR2018-00433 and IPR2018-00434 Petitions filed Jan. 9, 2018, 46 pgs.
Kumaresan, Palani et al., "High-Throughput Single Copy DNA Amplification and Cell Analysis in Engineered Nanoliter Droplets," Analytical Chemistry, 17 pgs., Apr. 15, 2008.
Kunieda, Hironobu et al., "Effect of Hydrophilic- and Hydrophobic-Chain Lengths on the Phase Behavior of A-B-type Silicone Surfactants in Water," J. Phys. Chem. B, vol. 105, No. 23, pp. 5419-5426, (2001).
Labsmith, "CapTite™ Microfluidic Interconnects" webpage, downloaded Jul. 11, 2012.
Labsmith, "Microfluid Components" webpage, downloaded Jul. 11, 2012.
Landegren, Ulf et al., "Padlock and proximity probes for in situ and array-based analyses: tools for the post-genomic era," Comp. Funct. Genom, vol. 4, pp. 525-530, (2003).
Leamon, John H. et al., "Overview: methods and applications for droplet compartmentalization of biology," Nature Methods, vol. 3, No. 7, pp. 541-543, Jul. 2006.
European Patent Office, "Annex to Summons to Attend Oral Proceedings", in connection with related European Patent Application No. 11760359.7, dated Mar. 28, 2018, 4 pgs.
Li, Paul C. H. et al., "Microfluidic Lab-on-a-Chip", (Book Chapter) Ewing's Analytical Instrumentation Handbook Third Edition, (2005), pp. 581-679.
Lin, Yen-Heng et al., "Droplet Formation Utilizing Controllable Moving-Wall Structures for Double-Emulsion Applications," Journal of Microelectromechanical Systems, vol. 17, No. 3, pp. 573-581, Jun. 2008.
Link, Darren R. et al., "Electric Control of Droplets in Microfluidic Devices," Angewandte Chemie Int. Ed., vol. 45, pp. 2556-2560, (2006).
Liu, Kan et al., "Droplet-based synthetic method using microflow focusing and droplet fusion," Microfluid Nanfluid, vol. 3, pp. 239-243, (2007), published online Sep. 22, 2006.
Lo, Y. M. Dennis et al., "Digital PCR for the molecular detection of fetal chromosomal aneuploidy," PNAS, vol. 104, No. 32, pp. 13116-13121, Aug. 7, 2007.
Luk, Vivienne N. et al., "Pluronic Additives: A Solution to Sticky Problems in Digital Microfluidics," Langmuir, vol. 24, No. 12, pp. 6382-6289, May 16, 2008.
Macris Kiss, Margaret et al., "High-Throughput Quantitative Polymerase Chain Reaction in Picoliter Droplets," Analytical Chemistry, 8 pgs., downloaded Nov. 17, 2008.
Mair, Dieudonne A. et al., "Injection molded microfluidic chips featuring integrated interconnects", Lab on a Chip, 2006, vol. 6, pp. 1346-1354.
Margulies, Marcel et al., "Genome sequencing in microfabricated high-density picolitre reactors," Nature, vol. 437, 51 pgs., Sep. 15, 2005.
Markey, Amelia L. et al., "High-throughput droplet PCR," Methods, vol. 50, pp. 277-281, Feb. 2, 2010.
Mazutis, Linas et al., "A fast and efficient microfluidic system for highly selective one-to-one droplet fusion," Lab on a Chip, vol. 9, pp. 2665-2672, Jun. 12, 2009.
Mazutis, Linas et al., "Droplet-Based Microfluidic Systems for High-Throughput Single DNA Molecule Isothermal Amplification and Analysis," Analytical Chemistry, vol. 81, No. 12, pp. 4813-4821, Jun. 15, 2009.
McCaughan, Frank et al., "Single-molecule genomics," Journal of Pathology, vol. 220, pp. 297-306, Nov. 19, 2009.
Mehta, Somil C. et a., "Mechanism of Stabilization of Silicone Oil—Water Emulsions Using Hybrid Siloxane Polymers," Langmuir, vol. 24, No. 9, pp. 4558-4563, Mar. 26, 2008.
Merriam-Webster Dictionary definition of "Gasket", included as an exhibit in IPR2018-00300 Petition filed Dec. 14, 2017, 1 page.
Mohr, S. et al., "Numerical and experimental study of a droplet-based PCR chip," Microfluid Nanofluid, vol. 3, pp. 611-621, (2007).
Musyanovych, Anna et al., "Miniemulsion Droplets as Single Molecule Nanoreactors for Polymerase Chain Reaction," Biomacromolecules, vol. 6, No. 4, pp. 1824-1828, (2005).
Nagai, Hidenori et al., "Development of A Microchamber Array for Picoliter PCR," Analytical Chemistry, vol. 73, No. 5, pp. 1043-1047, Mar. 1, 2001.
Nam, Yoon Sung et al., "Nanosized Emulsions Stabilized by Semi-solid Polymer Interphase," Langmuir, ACS Publications, Jul. 23, 2010.
Newman, D. A. et al., "Phase Behavior of Fluoroether-Functional Amphiphiles in Supercritical Carbon Dioxide," The Journal of Supercritical Fluids, vol. 6, No. 4, pp. 205-210, (1993).
Nie, Shuming et al., "Optical Detection of Single Molecules," Annu. Rev. Biophys. BiomoL Struct. vol. 26, pp. 567-596, (1997).
Nisisako, Takasi et al., "Microfluidic large-scale integration on a chip for mass production of monodisperse droplets and particles", Lab on a Chip, vol. 8, (2008), pp. 287-293.
O'Lenick, Jr., Anthony J., "Silicone Emulsions and Surfactants—A Review," Silicone Spectator, Silitech LLC, May 2009 (original published May 2000).
O'Lenick, Jr., Anthony J., "Silicone Emulsions and Surfactants," Journal of Surfactants and Detergents, vol. 3, No. 3, Jul. 2000.
Pamme, Nicole, "continuous flow separations in microfluidic devices," Lab on a Chip, vol. 7, pp. 1644-1659, Nov. 2, 2007.
Piatyszek, Mieczyslaw A. et al., "Detection of telomerase activity in human cells and tumors by a telomeric repeat amplification protocol (TRAP)," Methods in Cell Science 17, pp. 1-15, (1995).
Pinheiro, Leonardo B. et al., "Evaluation of a Droplet Digital Polymerase Chain Reaction Format for DNA Copy Number Quantification," Analytical Chemistry, vol. 84, pp. 1003-1011, Nov. 28, 2011.
Pohl, Gudrun et al., "Principle and applications of digital PCR" review, www.future-drugs.com, Expert Rev. Mol. Diagn. 4(1), pp. 41-47, (2004).
Polydimethylsiloxane, 5 pgs., published in FNP 52 (1992).
Price, Christopher B., "Regular Review Point of Care Testing," BMJ, vol. 322, May 26, 2001.

(56) References Cited

OTHER PUBLICATIONS

Qin, Jian et al., "Studying copy number variations using a nanofluidic platform," Nucleic Acids Research, vol. 36, No. 18, pp. 1-8, Aug. 18, 2008.
Roach, L. Spencer et al., "Controlling Nonspecific Protein Absorption in a Plug-Based Microfluidic System by Controlling Interfacial Chemistry Using Fluorous-Phase Surfactants," Analytical Chemistry vol. 77, No. 3, pp. 785-796, Feb. 1, 2005.
Rutledge, R. G. et al., "Mathematics of quantitative kinetic PCR and the application of standard curves," Nucleic Acids Research, vol. 31, No. 16, pp. 1-6, (2003).
Rutledge, R. G., "Sigmoidal curve-fitting redefines quantitative real-time PCR with the prospective of developing automated high-throughput applications," Nucleic Acids Research. vol. 32, No. 22, pp. 1-8, (2004).
Scherer, A., California Institute of Technology, "Polymerase Chain Reactors" PowerPoint presentation, 24 pgs., date unknown.
Schneegaß, Ivonne et al., "Miniaturized flow-through PCR with different template types in a silicon chip thermocycler," Lab on a Chip, vol. 1, pp. 42-49, (2001).
Schroeder, Groff M. et al., "Introduction to Flow Cytometry" version 5.1, 182 pgs. (2004).
Schütze, Tatjana et al., "A streamlined protocol for emulsion polymerase chain reaction and subsequent purification," Analytical Biochemistry, vol. 410, pp. 155-157, Nov. 25, 2010.
Sela, Y. et al., "Newly designed polysiloxane-graft-poly (oxyethylene) copolymeric surfactants: preparation, surface activity and emulsification properties," Colloid & Polymer Science 272, pp. 684-691, (1994).
Shah, Rhutesh K. et al., "Polymers fit for function Making emulsions drop by drop," Materials Today, vol. 11, No. 4, pp. 18-27, Apr. 2008.
Shendure, Jay et al., "Next-generation DNA sequencing," Nature Biotechnology, vol. 26, No. 10, pp. 1135-1145, Oct. 2008.
Shuber, Anthony P. et al., "A Simplified Procedure for Developing Multiplex PCRs," Genome Research, published by Cold Spring Harbor Laboratory Press, pp. 488-493, (1995).
Sigma-Aldrich, "Synthesis of Mesoporous Materials," Material Matters, 3.1, 17, (2008).
Singley, Edith J. et al., "Phase behavior and emulsion formation of novel fluoroether amphiphiles in carbon dioxide," Fluid Phase Equilibria 128, pp. 199-219, (1997).
Smid-Korbar, J. et al., "Efficiency and usability of silicone surfactants in emulsions," International Journal of Cosmetic Science 12, pp. 135-139, (1990), presented at the 15$^{th}$ IFSCC International Congress, Sep. 26-29, 1988, London.
Snow, Steven A., "Synthesis and Characterization of Zwitterionic Silicone Sulfobetaine Surfactants," Langmuir, vol. 6, No. 2, American Chemical Society, pp. 385-391, (1990).
Solimini, Nicole L. et al., "Recurrent Hemizygous Deletions in Cancers May Optimize Proliferative Potential," Science, vol. 337, pp. 104-109, Jul. 6, 2012.
Canadian Intellectual Property Office, "Office Action" in connection with related Canadian Patent App. No. 2,767,182, dated Sep. 13, 2017, 4 pgs.
Swillens, Stéphane et al., "Instant evaluation of the absolute initial number of cDNA copies from a single real-time PCR curve," Nucleic Acids Research, vol. 32, No. 6, pp. 1-6, (2004).
Tanner, Nathan A. et al., "Simultaneous multiple target detection in real-time loop-mediated isothermal amplification," BioTechniques, vol. 53, pp. 8-19, Aug. 2012.
Teh, Shia-Yen et al., "Droplet microfluidics," Lab on a Chip, vol. 8, pp. 198-220, Jan. 11, 2008.
Thinxxs Microtechnology AG, "Emerald Biosystems: Protein Crystallization," 1 pg., downloaded Mar. 8, 2011.
Thurecht, Kristofer J. et al., "Investigation of spontaneous microemulsion formation in supercritical carbon dioxide using high-pressure NMR," Journal of Supercritical Fluids, vol. 38, pp. 111-118, (2006).
Thurecht, Kristofer J. et al., "Kinetics of Enzymatic Ring-Opening Polymerization of e-Caprolactone in Supercritical Carbon Dioxide," Macromolecules, vol. 39, pp. 7967-7972, (2006).
United States Patent and Trademark Office, Patent Trial and Appeal Board, "Decision Denying Institution of Inter Partes Review" related to IPR Case No. IPR2018-00300, dated Jun. 15, 2018, 19 pgs.
United States Patent and Trademark Office, Patent Trial and Appeal Board, "Decision Denying Institution of Inter Partes Review" related to IPR Case No. IPR2018-00301, dated Jun. 15, 2018, 21 pgs.
United States Patent and Trademark Office, Patent Trial and Appeal Board, "Decision Denying Institution of Inter Partes Review" related to IPR Case No. IPR2018-00302, dated Jun. 15, 2018, 23 pgs.
United States Patent and Trademark Office, Patent Trial and Appeal Board, "Decision Denying Institution of Inter Partes Review" related to IPR Case No. IPR2018-00489, dated Jun. 28, 2018, 23 pgs.
United States Patent and Trademark Office, Patent Trial and Appeal Board, "Decision Denying Institution of Inter Partes Review" related to IPR Case No. IPR2018-00490, dated Jun. 28, 2018, 25 pgs.
United States Patent and Trademark Office, Patent Trial and Appeal Board, "Decision Denying Institution of Inter Partes Review" related to IPR Case No. IPR2018-00432, dated Jun. 29, 2018, 20 pgs.
United States Patent and Trademark Office, Patent Trial and Appeal Board, "Decision Denying Institution of Inter Partes Review" related to IPR Case No. IPR2018-00433, dated Jun. 29, 2018, 23 pgs.
United States Patent and Trademark Office, Patent Trial and Appeal Board, "Decision Denying Institution of Inter Partes Review" related to IPR Case No. IPR2018-00434, dated Jun. 29, 2018, 22 pgs.
Vogelstein, Bert et al., "Digital PCR," Proc. Natl. Acad. Sci. USA, vol. 96, pp. 9236-9241, Aug. 1999.
Vulto, Paul et al., "Phaseguides: a paradigm shift in microfluidic priming and emptying," Lab on a Chip, vol. 11, No. 9, pp. 1561-1700, May 7, 2011.
Wang, Anfeng et al., "Direct Force Measurement of Silicone- and Hydrocarbon-Based ABA Triblock Surfactants in Alcoholic Media by Atomic Force Mircroscopy," Journal of Colloid and Interface Science 256, pp. 331-340 (2002).
Weaver, Suzanne et al., "Taking qPCR to a higher level: Analysis of CNV reveals the power of high throughput qPCR to enhance quantitative resolution," Methods, vol. 50, pp. 271-276, Jan. 15, 2010.
Weitz, David A., "Novel Surfactants for Stabilizing Emulsions of Water or Hydrocarbon Oil-Based Droplets in a Fluorocarbon Oil Continuous Phase," Harvard Office of Technology Development: Available Technologies, pp. 1-3, downloaded Nov. 28, 2008.
Wetmur, James G. et al., "Molecular haplotyping by linking emulsion PCR: analysis of paraoxonase 1 haplotypes and phenotypes," Nucleic Acids Research, vol. 33, No. 8, pp. 2615-2619, (2005).
Wetmur, James G., et al., "Linking Emulsion PCR Haplotype Analysis," PCR Protocols, Methods in Molecular Biology, vol. 687, pp. 165-175, (2011).
Whitesides, George M. et al., "Flexible Methods for Microfluidics", Physics Today, Jun. 2001, pp. 42-48.
Williams, Richard et al., "Amplification of complex gene libraries by emulsion PCR," Nature Methods, vol. 3, No. 7, pp. 545-550, Jul. 2006.
www.smithbearing.com, Fractional, Letter & Number Drill Sizes, included as an exhibit in IPR2018-00301 Petition filed Dec. 14, 2017 and IPR2018-00433 Petition filed Jan. 9, 2018, 1 page.
Yazdi, A. V. et al., "Highly Carbon Dioxide Soluble Surfactants, Dispersants and Chelating Agents," Fluid Phase Equilibria, vol. 117, pp. 297-303, (1996).
International Searching Authority, International Search Report, PCT Application Serial No. PCT/US2009/05317; mailing date: Nov. 20, 2009.

(56) References Cited

OTHER PUBLICATIONS

International Searching Authority, Written Opinion of the International Searching Authority, PCT Application Serial No. PCT/US2009/05317; mailing date: Nov. 20, 2009.

International Searching Authority, Commissioner of Patents, "International Search Report" in connection with related International App. No. PCT/US2011/030101, dated Jun. 1, 2011, 2 pgs.

International Searching Authority, Commissioner of Patents, "International Search Report" in connection with related International App. No. PCT/US2011/030101, dated Jun. 1, 2011, 9 pgs.

Zhang, Chunsun et al., "Miniaturized PCR chips for nucleic acid amplification and analysis: latest advances and future trends," Nucleic Acids Research, vol. 35, No. 13, pp. 4223-4237, Jun. 18, 2007.

Zhang, Tianhao et al., "Behavioral Modeling and Performance Evaluation of Microelectrofluidics-Based PCR Systems Using SystemC," IEEE Transactions on Computer-Aided Design of Integrated Circuits and Systems, vol. 23, No. 6, pp. 843-858, Jun. 2004.

Zhao, Yuejun et al., "Microparticle Concentration and Separation by Traveling-Wave Dielectrophoresis (twDEP) for Digital Microfluidics," Journal of Microelectromechanical Systems, vol. 16, No. 6, pp. 1472-1481, Dec. 2007.

Zhelev, Toshko et al., "Heat Integration in Micro-Fluidic Devices," 16th European Symposium on Computer Aided Process Engineering and 9th International Symposium on Process Systems Engineering, pp. 1863-1868 published by Elsevier B.V. (2006).

Zhong, Qun et al., "Multiplex digital PCR: breaking the one target per color barrier of quantitative PCR," Lab on a Chip, vol. 11, pp. 2167-2174, (2011).

Zimmermann, Bernhard G. et al., "Digital PCR: a powerful new tool for noninvasive prenatal diagnosis?," Prenatal Diagnosis, vol. 28 pp. 1087-1093, Nov. 10, 2008.

\* cited by examiner

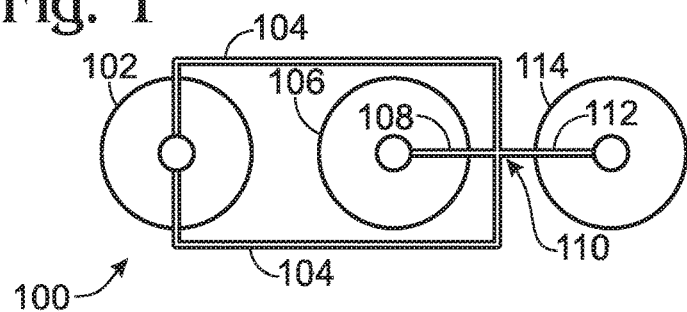
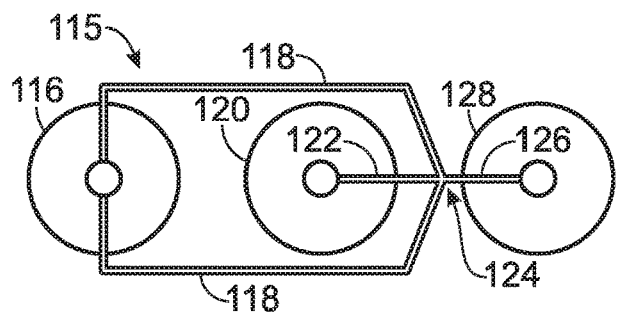
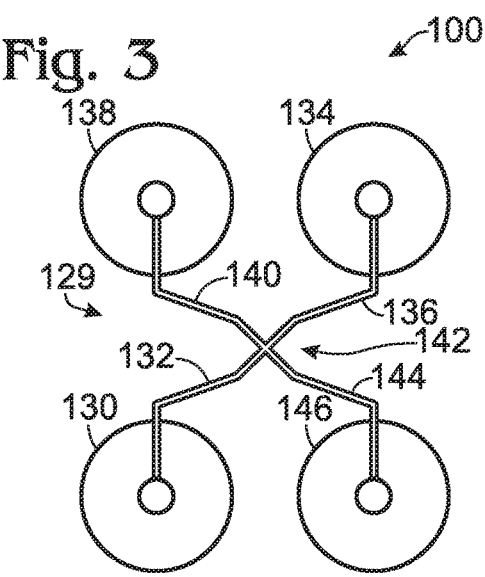
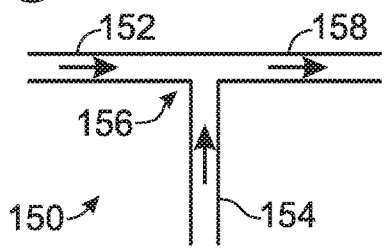
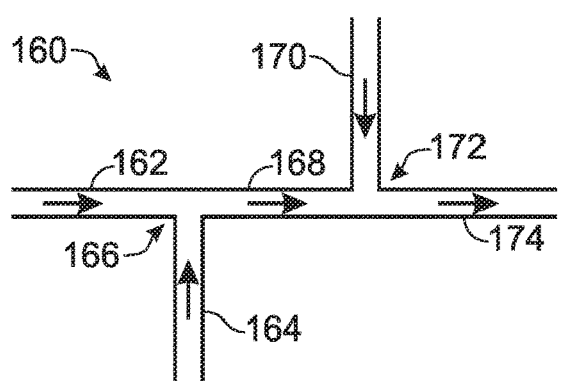
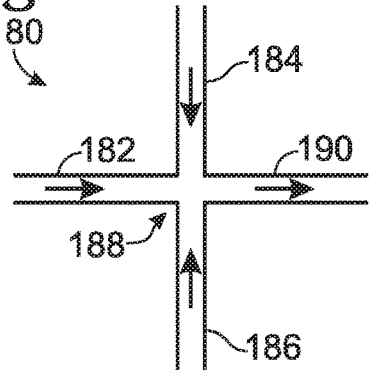

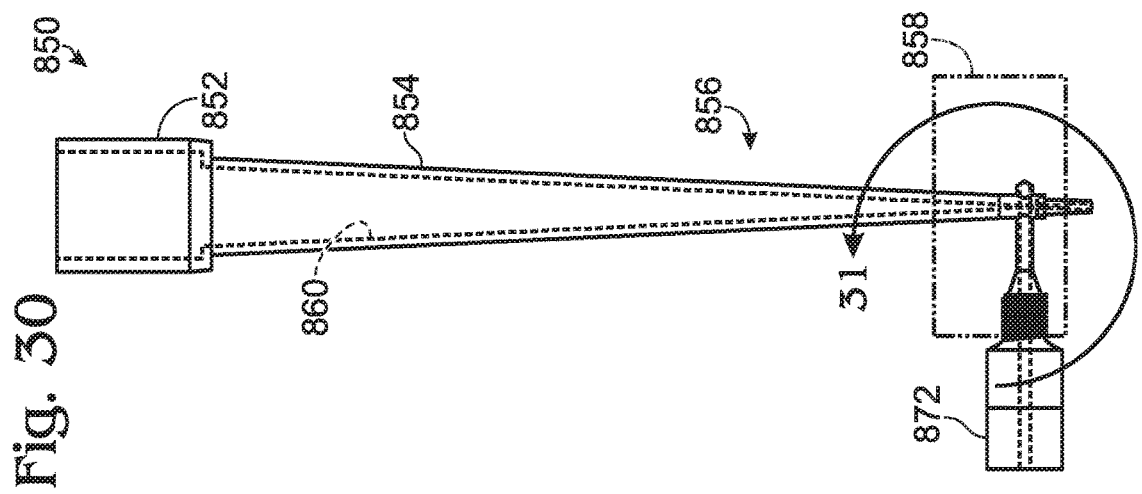
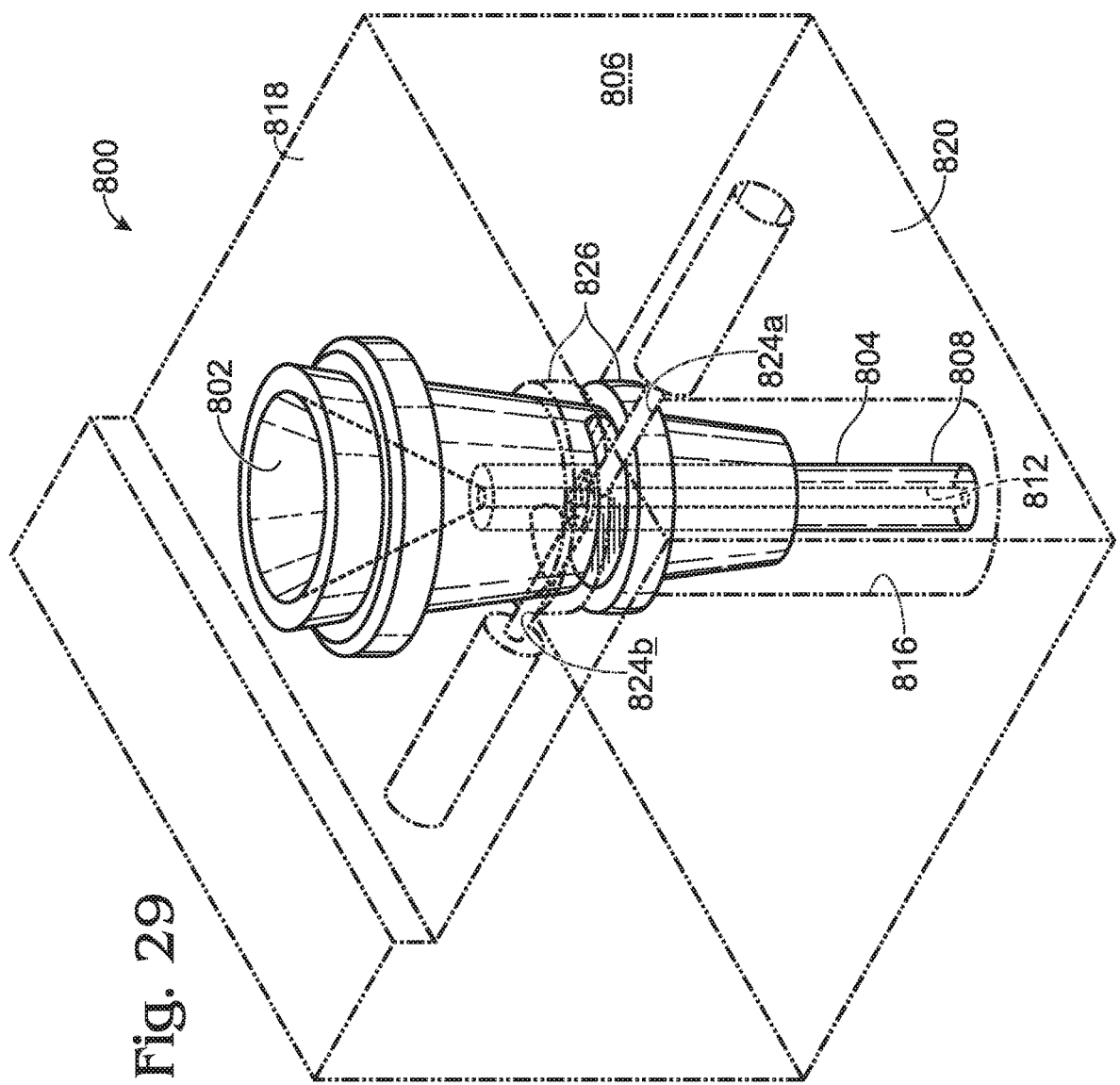

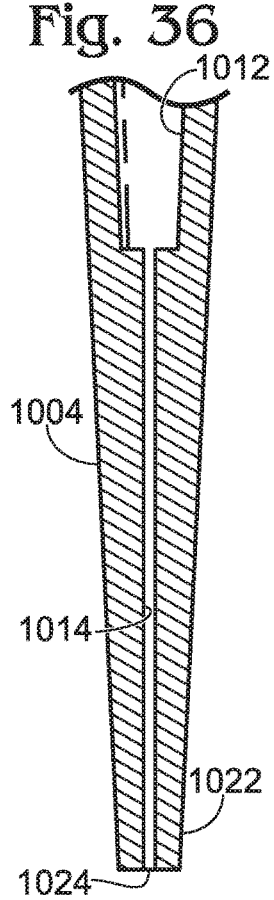
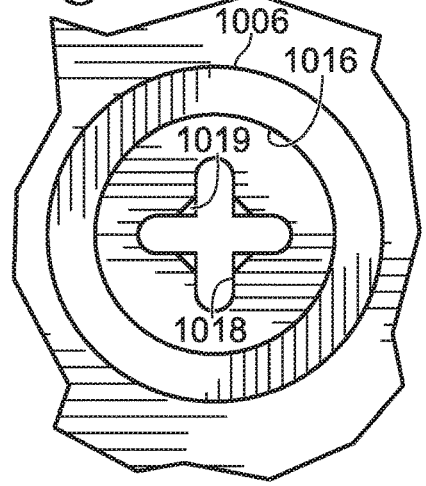
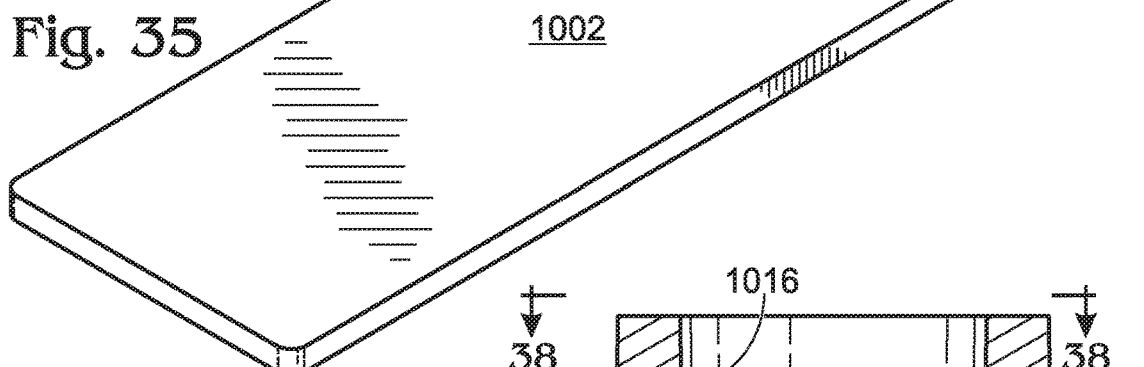
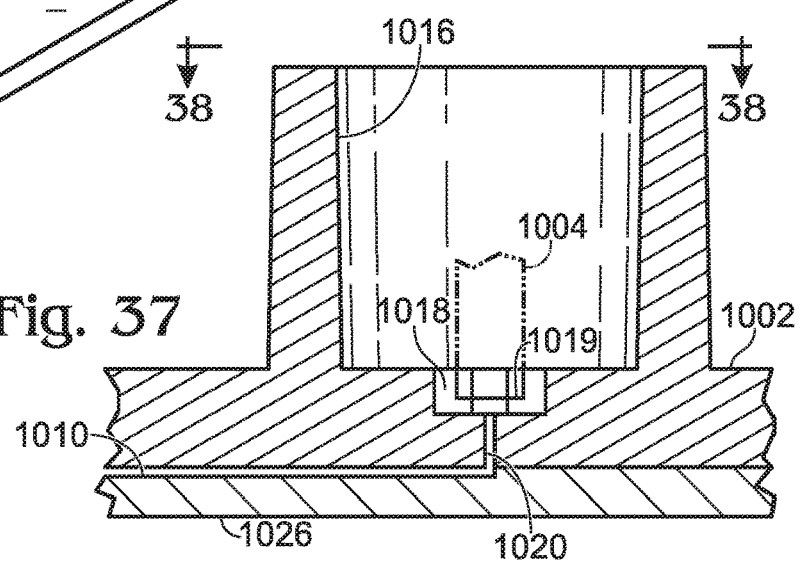

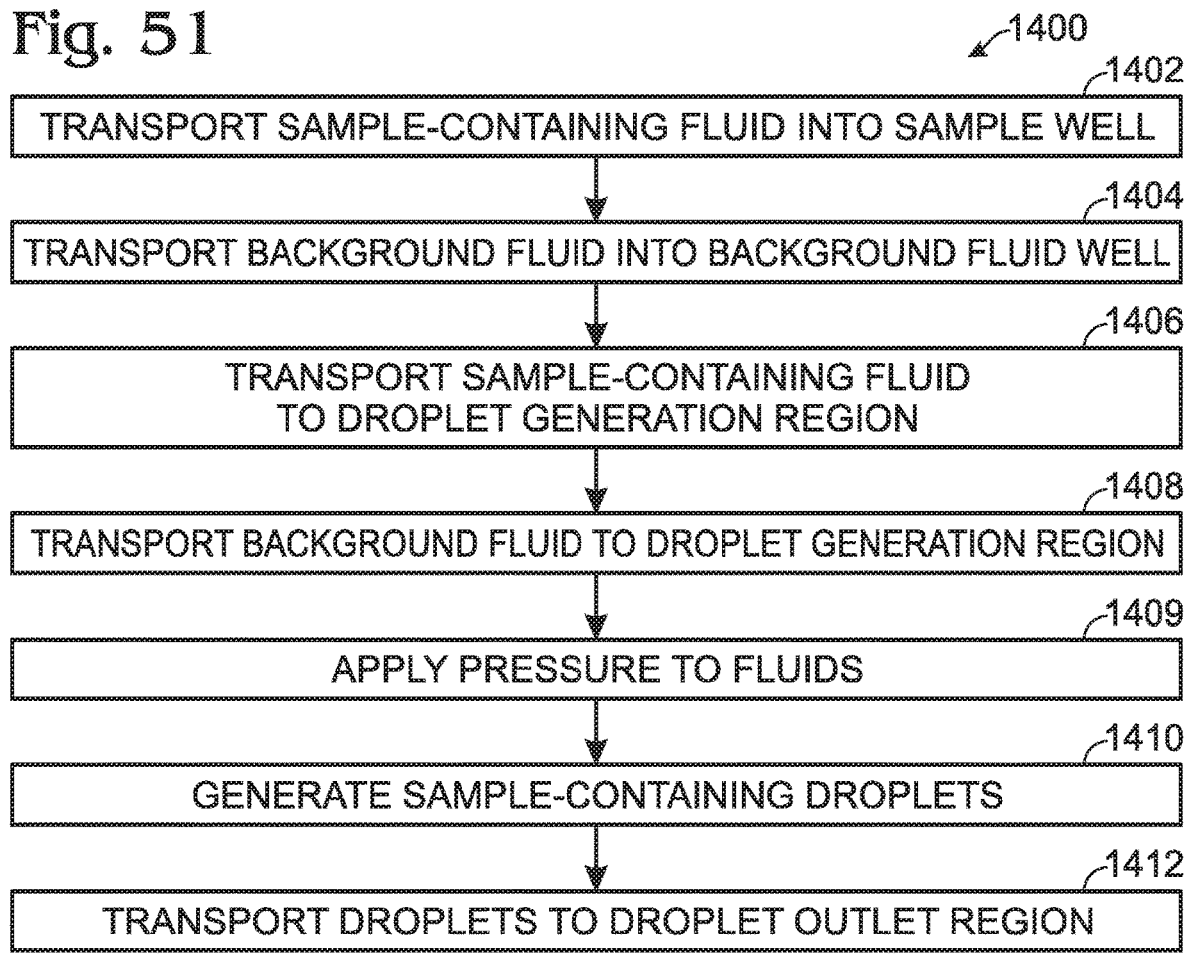

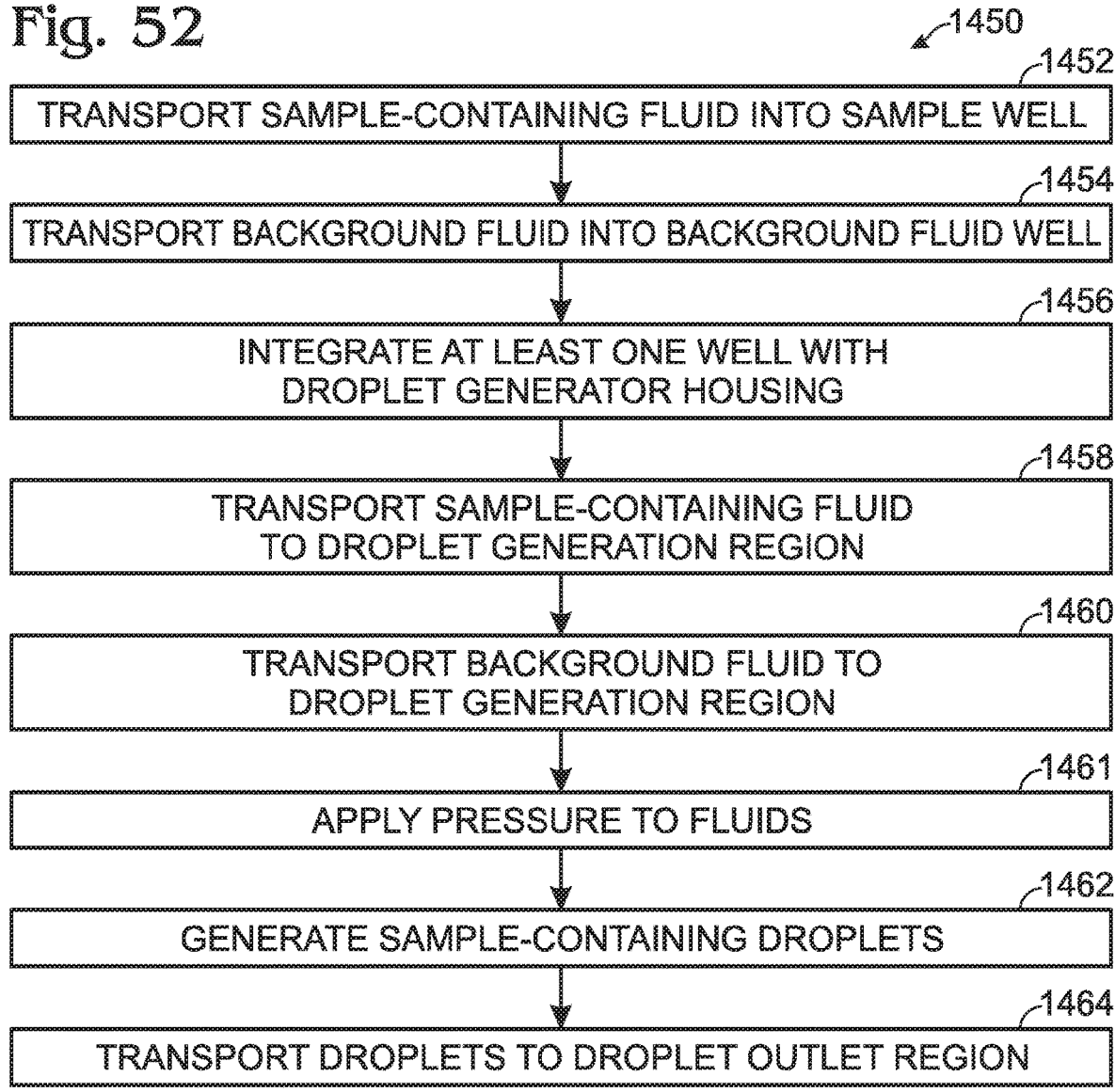

METHOD OF EMULSION FORMATION AND MODIFICATION

CROSS-REFERENCES TO PRIORITY APPLICATIONS

This application is a continuation of U.S. patent application Ser. No. 16/397,774, filed Apr. 29, 2019, now U.S. Pat. No. 10,744,506, which, in turn, is a continuation of U.S. patent application Ser. No. 16/160,783, filed Oct. 15, 2018, now U.S. Pat. No. 10,272,432, which, in turn, is a continuation of U.S. patent application Ser. No. 15/357,840, filed Nov. 21, 2016, now U.S. Pat. No. 10,099,219, which, in turn, is a continuation of U.S. patent application Ser. No. 13/341,669, filed Dec. 30, 2011, now U.S. Pat. No. 9,500,664, which, in turn, is a continuation of PCT Patent Application Serial No. PCT/US2011/030101, filed Mar. 25, 2011, which, in turn, is based upon and claims the benefit under 35 U.S.C. § 119(e) of U.S. Provisional Patent Application Ser. No. 61/341,218, filed Mar. 25, 2010. Each of these priority applications is incorporated herein by reference in its entirety for all purposes.

CROSS-REFERENCES TO OTHER MATERIALS

This application incorporates by reference in their entireties for all purposes the following materials: U.S. Pat. No. 7,041,481, issued May 9, 2006; U.S. Patent Application Publication No. 2010/0173394 A1, published Jul. 8, 2010; and Joseph R. Lakowicz, PRINCIPLES OF FLUORESCENCE SPECTROSCOPY (2nd Ed. 1999).

INTRODUCTION

Many biomedical applications rely on high-throughput assays of samples combined with reagents. For example, in research and clinical applications, high-throughput genetic tests using target-specific reagents can provide high-quality information about samples for drug discovery, biomarker discovery, and clinical diagnostics, among others. As another example, infectious disease detection often requires screening a sample for multiple genetic targets to generate high-confidence results.

The trend is toward reduced volumes and detection of more targets. However, creating and mixing smaller volumes can require more complex instrumentation, which increases cost. Accordingly, improved technology is needed to permit testing greater numbers of samples and combinations of samples and reagents, at a higher speed, a lower cost, and/or with reduced instrument complexity.

Emulsions hold substantial promise for revolutionizing high-throughput assays. Emulsification techniques can create billions of aqueous droplets that function as independent reaction chambers for biochemical reactions. For example, an aqueous sample (e.g., 200 microliters) can be partitioned into droplets (e.g., four million droplets of 50 picoliters each) to allow individual sub-components (e.g., cells, nucleic acids, proteins) to be manipulated, processed, and studied discretely in a massively high-throughput manner.

Splitting a sample into droplets offers numerous advantages. Small reaction volumes (picoliters to nanoliters) can be utilized, allowing earlier detection by increasing reaction rates and forming more concentrated products. Also, a much greater number of independent measurements (thousands to millions) can be made on the sample, when compared to conventional bulk volume reactions performed on a micoliter scale. Thus, the sample can be analyzed more accurately (i.e., more repetitions of the same test) and in greater depth (i.e., a greater number of different tests). In addition, small reaction volumes use less reagent, thereby lowering the cost per test of consumables. Furthermore, microfluidic technology can provide control over processes used for the generation, mixing, incubation, splitting, sorting, and detection of droplets, to attain repeatable droplet-based measurements.

Aqueous droplets can be suspended in oil to create a water-in-oil emulsion (W/O). The emulsion can be stabilized with a surfactant to reduce or prevent coalescence of droplets during heating, cooling, and transport, thereby enabling thermal cycling to be performed. Accordingly, emulsions have been used to perform single-copy amplification of nucleic acid target molecules in droplets using the polymerase chain reaction (PCR).

Compartmentalization of single molecules of a nucleic acid target in droplets of an emulsion alleviates problems encountered in amplification of larger sample volumes. In particular, droplets can promote more efficient and uniform amplification of targets from samples containing complex heterogeneous nucleic acid populations, because sample complexity in each droplet is reduced. The impact of factors that lead to biasing in bulk amplification, such as amplification efficiency, G+C content, and amplicon annealing, can be minimized by droplet compartmentalization. Unbiased amplification can be critical in detection of rare species, such as pathogens or cancer cells, the presence of which could be masked by a high concentration of background species in complex clinical samples.

Despite their allure, emulsion-based assays present technical challenges for high-throughput testing, which can require creation of tens, hundreds, thousands, or even millions of individual samples and sample/reagent combinations. Thus, there is a need for improved techniques for the generation, mixing, incubation, splitting, sorting, and detection of droplets.

SUMMARY

The present disclosure provides systems, including methods and apparatus, for generating droplets suitable for droplet-based assays. The disclosed systems may include either one-piece or multi-piece droplet generation components configured to form sample-containing droplets by merging aqueous, sample-containing fluid with a background emulsion fluid such as oil, to form an emulsion of sample-containing droplets suspended in the background fluid. In some cases, the disclosed systems may include channels or other suitable mechanisms configured to transport the sample-containing droplets to an outlet region, so that subsequent assay steps may be performed.

BRIEF DESCRIPTION OF THE DRAWINGS

FIG. 1 is a top view of an exemplary droplet generator, in accordance with aspects of the present disclosure.

FIG. 2 is a top view of another exemplary droplet generator, in accordance with aspects of the present disclosure.

FIG. 3 is a top view of another exemplary droplet generator, in accordance with aspects of the present disclosure.

FIG. 4 is a schematic top view of an exemplary droplet generation region, in accordance with aspects of the present disclosure.

FIG. 5 is a schematic top view of another exemplary droplet generation region, in accordance with aspects of the present disclosure.

FIG. 6 is a schematic top view of another exemplary droplet generation region, in accordance with aspects of the present disclosure.

FIG. 29 is a partially transparent isometric view of the portion of the droplet generation system shown in FIG. 28 assembled with a droplet generation housing.

FIG. 30 is an elevational view of still another droplet generation system, in accordance with aspects of the present teachings.

FIG. 35 is an exploded isometric view of still another droplet generation system, in accordance with aspects of the present teachings.

FIG. 36 is a magnified sectional view of a portion of the droplet generation system of FIG. 35.

FIG. 37 is a magnified sectional view of another portion of the droplet generation system of FIG. 35.

FIG. 38 is a magnified top view of another portion of the droplet generation system of FIG. 35.

FIG. 51 is a flow chart depicting a method of generating sample-containing droplets, in accordance with aspects of the present teachings.

FIG. 52 is a flow chart depicting another method of generating sample-containing droplets, in accordance with aspects of the present teachings.

DETAILED DESCRIPTION

Figure 7:
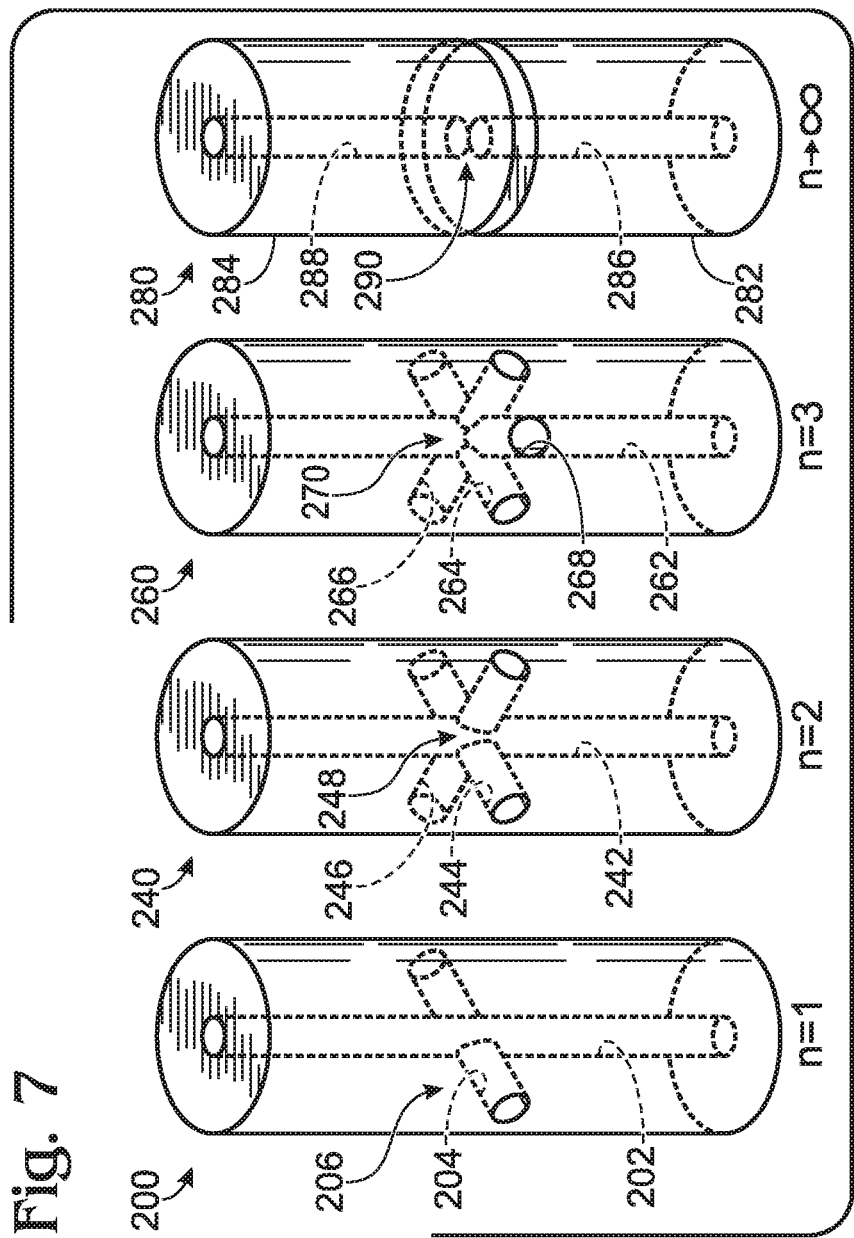
FIG. 7 is an isometric view of four different droplet generators, illustrating the relationship between various cross-type droplet generators, in accordance with aspects of the present disclosure.

The present disclosure provides systems, including apparatus and methods, for generating droplets suitable for droplet-based assays. Droplet generation systems according to the present teachings may be part of an overall assay system configured to test for the presence of one or more target molecules in a sample. These overall systems may include methods and apparatus for (A) preparing a sample, such as a clinical or environmental sample, for analysis, (B) separating components of the samples by partitioning them into droplets or other partitions, each containing only about one component (such as a single copy of a nucleic acid target or other analyte of interest), (C) amplifying or otherwise reacting the components within the droplets, (D) detecting the amplified or reacted components, or characteristics thereof, and/or (E) analyzing the resulting data. In this way, complex samples may be converted into a plurality of simpler, more easily analyzed samples, with concomitant reductions in background and assay times.

Droplet generation systems according to the present teachings may involve, among others, the following four modes of droplet generation: (A) planar mode droplet generation, (B) continuous mode droplet generation, (C) two-part mode droplet generation, and (D) single hole mode droplet generation. Droplet generation systems according to each mode share the characteristic that portions of the system exposed to a sample are configured to be disposable, whereas other portions of the system may be reusable for multiple different samples. Features of the various modes, as well as exemplary embodiments corresponding to each mode, will be described in detail below, in the following sections: (I) definitions, (II) general principles of droplet generation, (III) planar mode examples, (IV) continuous mode examples, (V) two-part mode examples, (VI) single hole mode examples, (VII) methods of operation, and (VIII) exemplary numbered paragraphs.

I. Definitions

Technical terms used in this disclosure have the meanings that are commonly recognized by those skilled in the art. However, the following terms may have additional meanings, as described below.

Emulsion—a composition comprising liquid droplets disposed in an immiscible carrier fluid, which also is liquid. The carrier fluid, also termed a background fluid, forms a continuous phase, which may be termed a carrier phase, a carrier, and/or a background phase. The droplets (e.g., aqueous droplets) are formed by at least one droplet fluid, also termed a foreground fluid, which is a liquid and which forms a droplet phase (which may be termed a dispersed phase or discontinuous phase). The droplet phase is immiscible with the continuous phase, which means that the droplet phase (i.e., the droplets) and the continuous phase (i.e., the carrier fluid) do not mix to attain homogeneity. The droplets are isolated from one another by the continuous phase and encapsulated (i.e., enclosed/surrounded) by the continuous phase.

The droplets of an emulsion may have any uniform or non-uniform distribution in the continuous phase. If non-uniform, the concentration of the droplets may vary to provide one or more regions of higher droplet density and one or more regions of lower droplet density in the continuous phase. For example, droplets may sink or float in the continuous phase, may be clustered in one or more packets along a channel, may be focused toward the center or perimeter of a flow stream, or the like. When droplets are said to be "suspended in the background fluid," this is intended to cover all of these possibilities.

Any of the emulsions disclosed herein may be monodisperse, that is, composed of droplets of at least generally uniform size, or may be polydisperse, that is, composed of droplets of various sizes. If monodisperse, the droplets of the emulsion may, for example, vary in volume by a standard deviation that is less than about plus or minus 100%, 50%, 20%, 10%, 5%, 2%, or 1% of the average droplet volume. Droplets generated from an orifice may be monodisperse or polydisperse.

An emulsion may have any suitable composition. The emulsion may be characterized by the predominant liquid compound or type of liquid compound in each phase. The predominant liquid compounds in the emulsion may be water and oil. "Oil" is any liquid compound or mixture of liquid compounds that is immiscible with water and that has a high content of carbon. In some examples, oil also may have a high content of hydrogen, fluorine, silicon, oxygen, or any combination thereof, among others. For example, any of the emulsions disclosed herein may be a water-in-oil (W/O) emulsion (i.e., aqueous droplets in a continuous oil phase). The oil may, for example, be or include at least one silicone oil, mineral oil, fluorocarbon oil, vegetable oil, or a combination thereof, among others. Any other suitable components may be present in any of the emulsion phases, such as at least one surfactant, reagent, sample (i.e., partitions thereof), other additive, label, particles, or any combination thereof.

Standard emulsions become unstable when heated (e.g., to temperatures above 60° C.) when they are in a packed state (e.g., each droplet is near a neighboring droplet), because heat generally lowers interfacial tensions, which can lead to droplet coalescence. Thus, standard packed emulsions do not maintain their integrity during high-temperature reactions, such as PCR, unless emulsion droplets are kept out of contact with one another or additives (e.g., other oil bases, surfactants, etc.) are used to modify the stability conditions (e.g., interfacial tension, viscosity, steric hindrance, etc.). For example, the droplets may be arranged in single file and spaced from one another along a channel to permit thermal cycling in order to perform PCR. However, following this approach using a standard emulsion does not permit a high density of droplets, thereby substantially limiting throughput in droplet-based assays.

Any emulsion disclosed herein may be a heat-stable emulsion. A heat-stable emulsion is any emulsion that resists coalescence when heated to at least 50° C. A heat-stable emulsion may be a PCR-stable emulsion, which is an emulsion that resists coalescence throughout the thermal cycling of PCR (e.g., to permit performance of digital PCR). Accordingly, a PCR-stable emulsion may be resistant to coalescence when heated to at least 80° C. or 90° C., among others. Due to heat stability, a PCR-stable emulsion, in contrast to a standard emulsion, enables PCR assays to be performed in droplets that remain substantially monodisperse throughout thermal cycling. Accordingly, digital PCR assays with PCR-stable emulsions may be substantially more quantitative than with standard emulsions. An emulsion may be formulated as PCR stable by, for example, proper selection of carrier fluid and surfactants, among others. An exemplary oil formulation to generate PCR-stable emulsions for flow-through assays is as follows: (1) Dow Corning 5225C Formulation Aid (10% active ingredient in decamethylcyclopentasiloxane)—20% w/w, 2% w/w final concentration active ingredient, (2) Dow Corning 749 Fluid (50% active ingredient in decamethylcyclopentasiloxane)—5% w/w, 2.5% w/w active ingredient, and (3) Poly(dimethylsiloxane) Dow Corning 200® fluid, viscosity 5.0 cSt (25° C.)—75% w/w. An exemplary oil formulation to generate PCR-stable emulsions for batch assays is as follows: (1) Dow Corning 5225C Formulation Aid (10% active ingredient in decamethylcyclopentasiloxane)—20% w/w, 2% w/w final concentration active ingredient, (2) Dow Corning 749 Fluid (50% active ingredient in decamethylcyclopentasiloxane)—60% w/w, 30% w/w active ingredient, and (3) Poly(dimethylsiloxane) Dow Corning 200® fluid, viscosity 5.0 cSt (25° C.)—20% w/w.

Partition—a separated portion of a bulk volume. The partition may be a sample partition generated from a sample, such as a prepared sample, that forms the bulk volume. Partitions generated from a bulk volume may be substantially uniform in size or may have distinct sizes (e.g., sets of partitions of two or more discrete, uniform sizes). Exemplary partitions are droplets. Partitions may also vary continuously in size with a predetermined size distribution or with a random size distribution.

Droplet—a small volume of liquid, typically with a spherical shape, encapsulated by an immiscible fluid, such as a continuous phase of an emulsion. The volume of a droplet, and/or the average volume of droplets in an emulsion, may, for example, be less than about one microliter (i.e., a "microdroplet") (or between about one microliter and one nanoliter or between about one microliter and one picoliter), less than about one nanoliter (or between about one nanoliter and one picoliter), or less than about one picoliter (or between about one picoliter and one femtoliter), among others. A droplet (or droplets of an emulsion) may have a diameter (or an average diameter) of less than about 1000, 100, or 10 micrometers, or of about 1000 to 10 micrometers, among others. A droplet may be spherical or nonspherical. A droplet may be a simple droplet or a compound droplet, that is, a droplet in which at least one droplet encapsulates at least one other droplet.

Surfactant—a surface-active agent capable of reducing the surface tension of a liquid in which it is dissolved, and/or the interfacial tension with another phase. A surfactant, which also or alternatively may be described as a detergent and/or a wetting agent, incorporates both a hydrophilic portion and a hydrophobic portion, which collectively confer a dual hydrophilic-lipophilic character on the surfactant. A surfactant may be characterized according to a Hydrophile-Lipophile Balance (HLB) value, which is a measure of the surfactant's hydrophilicity compared to its lipophilicity. HLB values range from 0-60 and define the relative affinity of a surfactant for water and oil. Nonionic surfactants generally have HLB values ranging from 0-20 and ionic surfactants may have HLB values of up to 60. Hydrophilic surfactants have HLB values greater than about 10 and a greater affinity for water than oil. Lipophilic surfactants have HLB values less than about 10 and a greater affinity for oil than water. The emulsions disclosed herein and/or any phase thereof, may include at least one hydrophilic surfactant, at least one lipophilic surfactant, or a combination thereof. Alternatively, or in addition, the emulsions disclosed herein and/or any phase thereof, may include at least one nonionic (and/or ionic) detergent. Furthermore, an emulsion disclosed herein and/or any phase thereof may include a surfactant comprising polyethyleneglycol, polypropyleneglycol, or Tween 20, among others.

Packet—a set of droplets or other isolated partitions disposed in the same continuous volume or volume region of a continuous phase. A packet thus may, for example, constitute all of the droplets of an emulsion or may constitute a segregated fraction of such droplets at a position along a channel. Typically, a packet refers to a collection of droplets that when analyzed in partial or total give a statistically relevant sampling to quantitatively make a prediction regarding a property of the entire starting sample from which the initial packet of droplets was made. The packet of droplets also indicates a spatial proximity between the first and the last droplets of the packet in a channel.

As an analogy with information technology, each droplet serves as a "bit" of information that may contain sequence specific information from a target analyte within a starting sample. A packet of droplets is then the sum of all these "bits" of information that together provide statistically relevant information on the analyte of interest from the starting sample. As with a binary computer, a packet of droplets is analogous to the contiguous sequence of bits that comprises the smallest unit of binary data on which meaningful computations can be applied. A packet of droplets can be encoded temporally and/or spatially relative to other packets that are also disposed in a continuous phase (such as in a flow stream), and/or with the addition of other encoded information (optical, magnetic, etc.) that uniquely identifies the packet relative to other packets.

Test—a procedure(s) and/or reaction(s) used to characterize a sample, and any signal(s), value(s), data, and/or result(s) obtained from the procedure(s) and/or reaction(s). A test also may be described as an assay. Exemplary droplet-based assays are biochemical assays using aqueous assay mixtures. More particularly, the droplet-based assays may be enzyme assays and/or binding assays, among others. The enzyme assays may, for example, determine whether individual droplets contain a copy of a substrate molecule (e.g., a nucleic acid target) for an enzyme and/or a copy of an enzyme molecule. Based on these assay results, a concentration and/or copy number of the substrate and/or the enzyme in a sample may be estimated.

Reaction—a chemical reaction, a binding interaction, a phenotypic change, or a combination thereof, which generally provides a detectable signal (e.g., a fluorescence signal) indicating occurrence and/or an extent of occurrence of the reaction. An exemplary reaction is an enzyme reaction that involves an enzyme-catalyzed conversion of a substrate to a product.

Any suitable enzyme reactions may be performed in the droplet-based assays disclosed herein. For example, the reactions may be catalyzed by a kinase, nuclease, nucleotide cyclase, nucleotide ligase, nucleotide phosphodiesterase, polymerase (DNA or RNA), prenyl transferase, pyrophosphatase, reporter enzyme (e.g., alkaline phosphatase, beta-galactosidase, chloramphenicol acetyl transferse, glucuronidase, horse radish peroxidase, luciferase, etc.), reverse transcriptase, topoisomerase, etc.

Sample—a compound, composition, and/or mixture of interest, from any suitable source(s). A sample is the general subject of interest for a test that analyzes an aspect of the sample, such as an aspect related to at least one analyte that may be present in the sample. Samples may be analyzed in their natural state, as collected, and/or in an altered state, for example, following storage, preservation, extraction, lysis, dilution, concentration, purification, filtration, mixing with one or more reagents, pre-amplification (e.g., to achieve target enrichment by performing limited cycles (e.g., <15) of PCR on sample prior to PCR), removal of amplicon (e.g., treatment with uracil-d-glycosylase (UDG) prior to PCR to eliminate any carry-over contamination by a previously generated amplicon (i.e., the amplicon is digestable with UDG because it is generated with dUTP instead of dTTP)), partitioning, or any combination thereof, among others. Clinical samples may include nasopharyngeal wash, blood, plasma, cell-free plasma, buffy coat, saliva, urine, stool, sputum, mucous, wound swab, tissue biopsy, milk, a fluid aspirate, a swab (e.g., a nasopharyngeal swab), and/or tissue, among others. Environmental samples may include water, soil, aerosol, and/or air, among others. Research samples may include cultured cells, primary cells, bacteria, spores, viruses, small organisms, any of the clinical samples listed above, or the like. Additional samples may include foodstuffs, weapons components, biodefense samples to be tested for bio-threat agents, suspected contaminants, and so on.

Samples may be collected for diagnostic purposes (e.g., the quantitative measurement of a clinical analyte such as an infectious agent) or for monitoring purposes (e.g., to determine that an environmental analyte of interest such as a bio-threat agent has exceeded a predetermined threshold).

Analyte—a component(s) or potential component(s) of a sample that is analyzed in a test. An analyte is a specific subject of interest in a test where the sample is the general subject of interest. An analyte may, for example, be a nucleic acid, protein, peptide, enzyme, cell, bacteria, spore, virus, organelle, macromolecular assembly, drug candidate, lipid, carbohydrate, metabolite, or any combination thereof, among others. An analyte may be tested for its presence, activity, and/or other characteristic in a sample and/or in partitions thereof. The presence of an analyte may relate to an absolute or relative number, concentration, binary assessment (e.g., present or absent), or the like, of the analyte in a sample or in one or more partitions thereof. In some examples, a sample may be partitioned such that a copy of the analyte is not present in all of the partitions, such as being present in the partitions at an average concentration of about 0.0001 to 10,000, 0.001 to 1000, 0.01 to 100, 0.1 to 10, or one copy per partition.

Reagent—a compound, set of compounds, and/or composition that is combined with a sample in order to perform a particular test(s) on the sample. A reagent may be a target-specific reagent, which is any reagent composition that confers specificity for detection of a particular target(s) or analyte(s) in a test. A reagent optionally may include a chemical reactant and/or a binding partner for the test. A reagent may, for example, include at least one nucleic acid, protein (e.g., an enzyme), cell, virus, organelle, macromolecular assembly, potential drug, lipid, carbohydrate, inorganic substance, or any combination thereof, and may be an aqueous composition, among others. In exemplary embodiments, the reagent may be an amplification reagent, which may include at least one primer or at least one pair of primers for amplification of a nucleic acid target, at least one probe and/or dye to enable detection of amplification, a polymerase, nucleotides (dNTPs and/or NTPs), divalent magnesium ions, potassium chloride, buffer, or any combination thereof, among others.

Nucleic acid—a compound comprising a chain of nucleotide monomers. A nucleic acid may be single-stranded or double-stranded (i.e., base-paired with another nucleic acid), among others. The chain of a nucleic acid may be composed of any suitable number of monomers, such as at least about ten or one-hundred, among others. Generally, the length of a nucleic acid chain corresponds to its source, with synthetic nucleic acids (e.g., primers and probes) typically being shorter, and biologically/enzymatically generated nucleic acids (e.g., nucleic acid analytes) typically being longer.

A nucleic acid may have a natural or artificial structure, or a combination thereof. Nucleic acids with a natural structure, namely, deoxyribonucleic acid (DNA) and ribonucleic acid (RNA), generally have a backbone of alternating pentose sugar groups and phosphate groups. Each pentose group is linked to a nucleobase (e.g., a purine (such as adenine (A) or guanine (T)) or a pyrimidine (such as cytosine (C), thymine (T), or uracil (U))). Nucleic acids with an artificial structure are analogs of natural nucleic acids and may, for example, be created by changes to the pentose and/or phosphate groups of the natural backbone. Exemplary artificial nucleic acids include glycol nucleic acids (GNA), peptide nucleic acids (PNA), locked nucleic acid (LNA), threose nucleic acids (TNA), and the like.

The sequence of a nucleic acid is defined by the order in which nucleobases are arranged along the backbone. This sequence generally determines the ability of the nucleic acid to bind specifically to a partner chain (or to form an intramolecular duplex) by hydrogen bonding. In particular, adenine pairs with thymine (or uracil) and guanine pairs with cytosine. A nucleic acid that can bind to another nucleic acid in an antiparallel fashion by forming a consecutive string of such base pairs with the other nucleic acid is termed "complementary."

Replication—a process forming a copy (i.e., a direct copy and/or a complementary copy) of a nucleic acid or a segment thereof. Replication generally involves an enzyme, such as a polymerase and/or a ligase, among others. The nucleic acid and/or segment replicated is a template (and/or a target) for replication.

Amplification—a reaction in which replication occurs repeatedly over time to form multiple copies of at least one segment of a template molecule. Amplification may generate an exponential or linear increase in the number of copies as amplification proceeds. Typical amplifications produce a greater than 1,000-fold increase in copy number and/or signal. Exemplary amplification reactions for the droplet-based assays disclosed herein may include the polymerase chain reaction (PCR) or ligase chain reaction, each of which is driven by thermal cycling. The droplet-based assays also or alternatively may use other amplification reactions, which may be performed isothermally, such as branched-probe DNA assays, cascade-RCA, helicase-dependent amplification, loop-mediated isothermal amplification (LAMP), nucleic acid based amplification (NASBA), nicking enzyme amplification reaction (NEAR), PAN-AC, Q-beta replicase amplification, rolling circle replication (RCA), self-sustaining sequence replication, strand-displacement amplification, and the like. Amplification may utilize a linear or circular template.

Amplification may be performed with any suitable reagents. Amplification may be performed, or tested for its occurrence, in an amplification mixture, which is any composition capable of generating multiple copies of a nucleic acid target molecule, if present, in the composition. An amplification mixture may include any combination of at least one primer or primer pair, at least one probe, at least one replication enzyme (e.g., at least one polymerase, such as at least one DNA and/or RNA polymerase), and deoxynucleotide (and/or nucleotide) triphosphates (dNTPs and/or NTPs), among others. Further aspects of assay mixtures and detection strategies that enable multiplexed amplification and detection of two or more target species in the same droplet are described elsewhere herein, such as in Section X, among others.

PCR—nucleic acid amplification that relies on alternating cycles of heating and cooling (i.e., thermal cycling) to achieve successive rounds of replication. PCR may be performed by thermal cycling between two or more temperature set points, such as a higher melting (denaturation) temperature and a lower annealing/extension temperature, or among three or more temperature set points, such as a higher melting temperature, a lower annealing temperature, and an intermediate extension temperature, among others. PCR may be performed with a thermostable polymerase, such as Taq DNA polymerase (e.g., wild-type enzyme, a Stoffel fragment, FastStart polymerase, etc.), Pfu DNA polymerase, S-Tbr polymerase, Tth polymerase, Vent polymerase, or a combination thereof, among others. PCR generally produces an exponential increase in the amount of a product amplicon over successive cycles.

Any suitable PCR methodology or combination of methodologies may be utilized in the droplet-based assays disclosed herein, such as allele-specific PCR, assembly PCR, asymmetric PCR, digital PCR, endpoint PCR, hot-start PCR, in situ PCR, intersequence-specific PCR, inverse PCR, linear after exponential PCR, ligation-mediated PCR, methylation-specific PCR, miniprimer PCR, multiplex ligation-dependent probe amplification, multiplex PCR, nested PCR, overlap-extension PCR, polymerase cycling assembly, qualitative PCR, quantitative PCR, real-time PCR, RT-PCR, single-cell PCR, solid-phase PCR, thermal asymmetric interlaced PCR, touchdown PCR, or universal fast walking PCR, among others.

Digital PCR—PCR performed on portions of a sample to determine the presence/absence, concentration, and/or copy number of a nucleic acid target in the sample, based on how many of the sample portions support amplification of the target. Digital PCR may (or may not) be performed as endpoint PCR. Digital PCR may (or may not) be performed as real-time PCR for each of the partitions.

PCR theoretically results in an exponential amplification of a nucleic acid sequence (analyte) from a sample. By measuring the number of amplification cycles required to achieve a threshold level of amplification (as in real-time PCR), one can theoretically calculate the starting concentration of nucleic acid. In practice, however, there are many factors that make the PCR process non-exponential, such as varying amplification efficiencies, low copy numbers of starting nucleic acid, and competition with background contaminant nucleic acid. Digital PCR is generally insensitive to these factors, since it does not rely on the assumption that the PCR process is exponential. In digital PCR, individual nucleic acid molecules are separated from the initial sample into partitions, then amplified to detectable levels. Each partition then provides digital information on the presence or absence of each individual nucleic acid molecule within each partition. When enough partitions are measured using this technique, the digital information can be consolidated to make a statistically relevant measure of starting concentration for the nucleic acid target (analyte) in the sample.

The concept of digital PCR may be extended to other types of analytes, besides nucleic acids. In particular, a signal amplification reaction may be utilized to permit detection of a single copy of a molecule of the analyte in individual droplets, to permit data analysis of droplet signals for other analytes in the manner described in Section VII (e.g., using an algorithm based on Poisson statistics). Exemplary signal amplification reactions that permit detection of single copies of other types of analytes in droplets include enzyme reactions.

Qualitative PCR—a PCR-based analysis that determines whether or not a target is present in a sample, generally without any substantial quantification of target presence. In exemplary embodiments, digital PCR that is qualitative may be performed by determining whether a packet of droplets contains at least a predefined percentage of positive droplets (a positive sample) or not (a negative sample).

Quantitative PCR—a PCR-based analysis that determines a concentration and/or copy number of a target in a sample.

RT-PCR (reverse transcription-PCR)—PCR utilizing a complementary DNA template produced by reverse transcription of RNA. RT-PCR permits analysis of an RNA sample by (1) forming complementary DNA copies of RNA, such as with a reverse transcriptase enzyme, and (2) PCR amplification using the complementary DNA as a template. In some embodiments, the same enzyme, such as Tth polymerase, may be used for reverse transcription and PCR.

Real-time PCR—a PCR-based analysis in which amplicon formation is measured during the reaction, such as after completion of one or more thermal cycles prior to the final thermal cycle of the reaction. Real-time PCR generally provides quantification of a target based on the kinetics of target amplification.

Endpoint PCR—a PCR-based analysis in which amplicon formation is measured after the completion of thermal cycling.

Amplicon—a product of an amplification reaction. An amplicon may be single-stranded or double-stranded, or a combination thereof. An amplicon corresponds to any suitable segment or the entire length of a nucleic acid target.

Primer—a nucleic acid capable of, and/or used for, priming replication of a nucleic acid template. Thus, a primer is a shorter nucleic acid that is complementary to a longer template. During replication, the primer is extended, based on the template sequence, to produce a longer nucleic acid that is a complementary copy of the template. A primer may be DNA, RNA, an analog thereof (i.e., an artificial nucleic acid), or any combination thereof. A primer may have any suitable length, such as at least about 10, 15, 20, or 30 nucleotides. Exemplary primers are synthesized chemically. Primers may be supplied as at least one pair of primers for amplification of at least one nucleic acid target. A pair of primers may be a sense primer and an antisense primer that collectively define the opposing ends (and thus the length) of a resulting amplicon.

Probe—a nucleic acid connected to at least one label, such as at least one dye. A probe may be a sequence-specific binding partner for a nucleic acid target and/or amplicon. The probe may be designed to enable detection of target amplification based on fluorescence resonance energy transfer (FRET). An exemplary probe for the nucleic acid assays disclosed herein includes one or more nucleic acids connected to a pair of dyes that collectively exhibit fluorescence resonance energy transfer (FRET) when proximate one another. The pair of dyes may provide first and second emitters, or an emitter and a quencher, among others. Fluorescence emission from the pair of dyes changes when the dyes are separated from one another, such as by cleavage of the probe during primer extension (e.g., a 5' nuclease assay, such as with a TAQMAN probe), or when the probe hybridizes to an amplicon (e.g., a molecular beacon probe).

The nucleic acid portion of the probe may have any suitable structure or origin, for example, the portion may be a locked nucleic acid, a member of a universal probe library, or the like. In other cases, a probe and one of the primers of a primer pair may be combined in the same molecule (e.g., AMPLIFLUOR primers or SCORPION primers). As an example, the primer-probe molecule may include a primer sequence at its 3' end and a molecular beacon-style probe at its 5' end. With this arrangement, related primer-probe molecules labeled with different dyes can be used in a multiplexed assay with the same reverse primer to quantify target sequences differing by a single nucleotide (single nucleotide polymorphisms (SNPs)). Another exemplary probe for droplet-based nucleic acid assays is a Plexor primer.

Label—an identifying and/or distinguishing marker or identifier connected to or incorporated into any entity, such as a compound, biological particle (e.g., a cell, bacteria, spore, virus, or organelle), or droplet. A label may, for example, be a dye that renders an entity optically detectable and/or optically distinguishable. Exemplary dyes used for labeling are fluorescent dyes (fluorophores) and fluorescence quenchers.

Reporter—a compound or set of compounds that reports a condition, such as the extent of a reaction. Exemplary reporters comprise at least one dye, such as a fluorescent dye or an energy transfer pair, and/or at least one oligonucleotide. Exemplary reporters for nucleic acid amplification assays may include a probe and/or an intercalating dye (e.g., SYBR Green, ethidium bromide, etc.).

Code—a mechanism for differentiating distinct members of a set. Exemplary codes to differentiate different types of droplets may include different droplet sizes, dyes, combinations of dyes, amounts of one or more dyes, enclosed code particles, or any combination thereof, among others. A code may, for example, be used to distinguish different packets of droplets, or different types of droplets within a packet, among others.

Binding partner—a member of a pair of members that bind to one another. Each member may be a compound or biological particle (e.g., a cell, bacteria, spore, virus, organelle, or the like), among others. Binding partners may bind specifically to one another. Specific binding may be characterized by a dissociation constant of less than about $10^{-4}$, $10^{-6}$, $10^{-8}$, or $10^{-16}$ M. Exemplary specific binding partners include biotin and avidin/streptavidin, a sense nucleic acid and a complementary antisense nucleic acid (e.g., a probe and an amplicon), a primer and its target, an antibody and a corresponding antigen, a receptor and its ligand, and the like.

Channel—a passage for fluid travel. A channel generally includes at least one inlet, where fluid enters the channel, and at least one outlet, where fluid exits the channel. The functions of the inlet and the outlet may be interchangeable, that is, fluid may flow through a channel in only one direction or in opposing directions, generally at different times. A channel may include walls that define and enclose the passage between the inlet and the outlet. A channel may, for example, be formed by a tube (e.g., a capillary tube), in or on a planar structure (e.g., a chip), or a combination thereof, among others. A channel may or may not branch. A channel may be linear or nonlinear. Exemplary nonlinear channels include a channel extending along a planar flow path (e.g., a serpentine channel) a nonplanar flow path (e.g., a helical channel to provide a helical flow path). Any of the channels disclosed herein may be a microfluidic channel, which is a channel having a characteristic transverse dimension (e.g., the channel's average diameter) of less than about one millimeter. Channels also may include one or more venting mechanisms to allow fluid to enter/exit without the need for an open outlet. Examples of venting mechanisms include but are not limited to hydrophobic vent openings or the use of porous materials to either make up a portion of the channel or to block an outlet if present. A channel may or may not be elongate. For example, an elongate channel may take the form of a four-walled conduit, and a non-elongate channel may take the form of radial flow between two parallel disks. For example, the oil flow in a butted tube droplet generator may flow radially inward in a channel defined by the disk-shaped faces of the butted tubes.

Fluidics Network—an assembly for manipulating fluid, generally by transferring fluid between compartments of the assembly and/or by driving flow of fluid along and/or through one or more flow paths defined by the assembly. A fluidics network may include any suitable structure, such as one or more channels, chambers, reservoirs, valves, pumps, thermal control devices (e.g., heaters/coolers), sensors (e.g., for measuring temperature, pressure, flow, etc.), or any combination thereof, among others.

II. General Principles of Droplet Generation

It may be desirable, in systems such as DNA amplification systems, among others, to generate sample-containing droplets using a partially or completely disposable apparatus. This may be accomplished by a disposable cartridge configured to generate droplets as part of a series of sample preparation steps that also may include lysing, purification, and concentration, among others. However, in other cases, it may be desirable to provide a partially or completely disposable apparatus configured to perform droplet generation without performing substantial additional sample preparation steps. This may be desirable, for example, when the DNA amplification system is configured to analyze samples that are typically prepared at another location or by a practitioner. Under these circumstances, a dedicated droplet generation system may be the simplest and most economical solution.

The components of droplet generation systems described herein may include, for example, substrates, wells (i.e. reservoirs), channels, tubes, and the like. These components may be manufactured by any suitable method(s) known in the art, for example by injection molding, machining, and/or the like. In some cases, all of the components of a droplet generation system disclosed according to the present teachings may be proprietary. In other cases, one or more components of a disclosed system may be available as an off-the-shelf component, which may be integrated with other components either with or without modification.

Many configurations of droplet generators may be suitable as components of a droplet generation system according to the present teachings. For example, suitable droplet generators include butted tubes, tubes drilled with intersecting channels, tubes partially or completely inserted inside other tubes, and tubes having multiple apertures, among others, where "tubes" means elongate hollow structures of any cross-sectional shape. Suitable fluid reservoirs include pipette tips, spin columns, wells (either individual or in a plate array), tubes, and syringes, among others. This section describes some general principles of droplet generation that apply to the present teachings, and provides a few specific examples of droplet generators embodying those principles; see FIGS. 1-7.

In general, droplets generated according to the present teachings will be sample-containing droplets suspended in a background fluid such as oil. Droplets of this type may be referred to as "water-in-oil" droplets. "Sample-containing" means that the aqueous fluid from which the droplets are formed contains sample material to be analyzed for the presence of one or more target molecules. The droplets may contain additional components other than sample material. For example, droplet generation may be performed after the sample has been modified by mixing it with one or more reagents to form a bulk assay mixture.

Droplet generation may divide the sample fluid or the bulk assay mixture into a plurality of partitioned mixtures (and thus sample partitions) that are isolated from one another in respective droplets by an intervening, immiscible carrier fluid. The droplets may be generated from a sample serially, such as from one orifice and/or one droplet generator (which may be termed an emulsion generator). Alternatively, the droplets may be generated in parallel from a sample, such as from two or more orifices and/or two or more droplet generators in fluid communication with (and/or supplied by) the same sample. As another example, droplets may be generated in parallel from a perforated plate defining an array of orifices. In some examples, the droplets may be generated in bulk, such as by agitation or sonication, among others. In some examples, a plurality of emulsions may be generated, either serially or in parallel, from a plurality of samples.

Various exemplary droplet generation configurations may be suitable for generating water-in-oil droplets containing a mixture of sample and reagent. The generated droplets then may be transported to a thermocycling instrument for PCR amplification. Each depicted configuration is compatible with continuous production of emulsions and with any suitable method of pumping, including at least pressure-controlled pumping, vacuum-controlled pumping, centrifugation, gravity-driven flow, and positive displacement pumping. A droplet generator or droplet generation configuration according to the present disclosure may be connected to a pressure/pump source located on a complementary PCR instrument, or may include any pumps and/or pressure sources needed to facilitate droplet generation.

Each depicted droplet configuration in FIGS. 1-6 may be capable of high-throughput droplet generation (1,000 droplets per second) in a disposable device, such as a cartridge. Each configuration may be constructed in a number of different ways. For example, fluid channels may be formed in a single injection molded piece of material, which is then sealed with a sealing member such as a featureless film or other material layer. Alternatively, fluid channels may be formed by injection molding two layers of material that fit together to form the channels, such as cylindrical channels formed by complementary hemispherical grooves. The fluid channels of the droplet generation configurations depicted in FIGS. 1-6 may have varying channel depths, such as 50, 100, 150, 200, or 250 µm, among others. Furthermore, the principles of droplet generation that apply to the exemplary droplet generators of FIGS. 1-6 apply to many droplet generation configurations other than cartridge-based configurations. Several of these alternate configurations are described in this disclosure.

FIG. 1 depicts a 3-port cross droplet generation configuration 100 wherein oil from a first fluid well (or chamber) 102 is transferred through two similar branches of a fluid channel section 104. The oil from well 102 intersects with aqueous fluid from a second fluid chamber 106, which is transferred along a fluid channel section 108 to an intersection area generally indicated at 110. The oil from well 102 arrives at intersection 110 from two different and substantially opposite directions, whereas the aqueous solution arrives at the intersection along only a single path that is substantially perpendicular to both directions of travel of the arriving oil. The result is that at intersection 110, aqueous droplets in an oil background (i.e., a water-in-oil emulsion) are produced and transferred along a fluid channel section 112 to a third chamber 114, where the emulsion can be temporarily stored and/or transferred to a thermocycling instrument.

FIG. 2 depicts a configuration 115 that is similar in most respects to droplet generation configuration 100 depicted in FIG. 1. Specifically, in droplet generation configuration 115, oil from a first fluid chamber 116 is transferred through two similar branches of a fluid channel section 118. Fluid channel sections 118 intersect with a fluid channel section 122 that transfers aqueous fluid from a second fluid chamber 120, at an intersection area generally indicated at 124. As in configuration 100, the oil from chamber 116 arrives at intersection 110 from two different directions, but unlike in configuration 100, the oil does not arrive from substantially opposite (antiparallel) directions. Rather, channel sections 118 each intersect channel section 122 at a non-perpendicular angle, which is depicted as approximately 60 degrees in FIG. 48B. In general, configuration 115 may include oil fluid channels that intersect an aqueous fluid channel at any desired angle or angles. Oil flowing through channel sections 118 and aqueous solution flowing through channel section 122 combine to form a water-in-oil emulsion of aqueous droplets suspended in an oil background. As in the case of configuration 100, the droplets then may be transferred along a fluid channel section 126 to a third fluid chamber 128, for storage and/or transfer to a thermocycling instrument.

FIG. 3 depicts a four-port droplet generation configuration 129 that includes two separate oil wells or chambers. A first oil chamber 130 is configured to store oil and transfer the oil through a fluid channel section 132 toward a channel intersection point generally indicated at 142. A second oil chamber 134 is similarly configured to store and transfer oil toward the intersection point through a fluid channel section 136. An aqueous fluid chamber 138 is configured to store aqueous fluid, such as a sample/reagent mixture, and to transfer the aqueous fluid through fluid channel section 140 toward intersection point 142. When the oil traveling through fluid channel sections 132 and 136 intersects with the aqueous fluid traveling through fluid channel section 140, a water-in-oil emulsion of aqueous droplets suspended in oil is generated. Although fluid channel 140 is depicted as intersecting with each of fluid channels 132 and 136 at a perpendicular angle, in general the channels may intersect at any desired angle, as described previously with respect to droplet generation configuration 115 of FIG. 2. The emulsion generated at intersection 142 travels through outgoing fluid channel section 144 toward an emulsion chamber 146, where the emulsion may be temporarily held for transfer to an instrument, such as a thermocycling instrument.

FIGS. 4-6 schematically depict fluid channel intersection regions of several other possible droplet generation configurations, in which the arrows within the depicted fluid channels indicate the direction of fluid flow within each channel. Although fluid chambers for receiving and/or storing oil, water, and any generated emulsion are not depicted in FIGS. 4-6, these chambers or at least some source of oil and aqueous fluid would be present in a cartridge containing any of the depicted configurations. The fluid channels and any associated chambers may be formed by any suitable method, such as injection molding complementary sections of thermoplastic as described previously.

FIG. 4 depicts a "single T" configuration 150 in which oil traveling in an oil channel 152 intersects with aqueous fluid traveling in an aqueous channel 154 at fluid channel intersection 156, to produce a water-in-oil emulsion that travels through outgoing fluid channel 158. This configuration differs from those of FIGS. 1-3 in that oil arrives at the oil/water intersection from only a single direction. Accordingly, droplets may be formed by a slightly different physical mechanism than in configurations where oil arrives from two directions. For example, droplets formed in the single T configuration of FIG. 4 may be formed primarily by a shear mechanism rather than primarily by a compression mechanism. However, the physics of droplet formation is not completely understood and likely depends on many factors, including the channel diameters, fluid velocities, and fluid viscosities.

FIG. 5 depicts a "double T" configuration 160 in which oil traveling in an oil channel 162 intersects with aqueous fluid traveling in a first aqueous channel 164 at a first intersection 166, to produce a water-in-oil emulsion that travels through intermediate fluid channel 168. Channel 168 intersects with a second aqueous channel 170 at a second intersection 172, to generate additional water-in-oil droplets within the emulsion. This geometry also may be used to generate double emulsions of water-in-oil-in-water droplets, and/or to generate two populations of droplets with different compositions. In any case, all of the generated droplets then travel through outgoing fluid channel 174. This configuration again differs from those of FIGS. 1-3 in that oil arrives at the oil/water intersections from only a single direction. In addition, configuration 160 differs from single T configuration 150 depicted in FIG. 4 due to the presence of two oil/water intersections. This may result in a greater density of droplets in the water-in-oil emulsion generated by configuration 160 than in the emulsion generation by configuration 150, which includes only one oil/water intersection.

FIG. 6 depicts a droplet generation configuration 180 in which oil traveling in an oil channel 182 intersects with aqueous fluid traveling in first and second aqueous channels 184 and 186 at an intersection 188. In this configuration, the aqueous fluid arrives at the intersection from two opposite directions, both of which are substantially perpendicular to the direction of travel of the oil in channel 182. More generally, the aqueous fluid can intersect with the oil at any desired angles. Depending on at least the sizes of the various channels, the flow rates of the oil and the aqueous fluid, and the angle of intersection of the aqueous fluid channels with the oil channel, a configuration of this type may be suitable for producing either an oil-in-water emulsion or a water-in-oil emulsion. In either case, the emulsion will travel away from intersection 188 through outgoing fluid channel 190.

FIG. 7 illustrates various continuous droplet generators, which are characterized by being formed from a single piece of material, and the relationships between them. More specifically, FIG. 7 shows a first continuous droplet generator 200 including a single transverse channel intersecting an inner axial channel, a second continuous droplet generator 240 including two transverse channels intersecting an inner axial channel, a third continuous droplet generator 260 including three transverse channels intersecting an inner axial channel, and a butted tube droplet generator 280, which as described below would not typically be characterized as a continuous droplet generator. Other continuous droplet generators similar to these examples are possible, such as generators with more than three transverse channels intersecting an inner axial channel, or partially butted type generators in which the tubes remain connected to each other along a portion of their cross-sections.

Droplet generator 200 includes hollow channels 202, 204 that intersect at an intersection region 206. To generate droplets, one of these channels will generally carry a foreground fluid toward intersection region 206 from one direction, while the other channel carries a background fluid toward intersection region 206 from both directions. Typically, channel 202 will carry a foreground fluid such as a sample-containing solution, and channel 204 will carry a background fluid such as oil, but the opposite is also possible. In any case, an emulsion will be created at intersection region 206 and will continue moving through channel 202 in the direction of travel of the foreground fluid, as described in detail above.

Droplet generator 240 includes three hollow channels 242, 244, and 246 that intersect at an intersection region 248. To generate droplets, channel 242 will typically carry a foreground fluid such as a sample-containing solution toward intersection region 248 from a single direction, and each of channels 244, 246 will typically carry a background fluid such as oil toward intersection region 248 from two opposite directions. In that case, an emulsion will be created at intersection region 248 and will continue moving through channel 242 in the direction of travel of the foreground fluid. It is also possible that each of channels 244, 246 would carry a foreground fluid toward intersection region 248 from a single direction, and channel 242 would carry a background fluid toward intersection region 248 from two opposite directions. In that case, the emulsion created at intersection region 248 would travel through both channels 244 and 246, in the original directions of travel of the foreground fluid in each of those channels. Droplet generator 240 thus may function to produce droplets that emerge from two separate channels.

Similarly, droplet generator 260 includes four channels 262, 264, 266, 268 that intersect to generate an emulsion of foreground fluid droplets in background fluid at an intersection region 250. By analogy to the three-channel configuration of droplet generator 240, the four-channel configuration of droplet generator 260 may be used either to generate a single emulsion that travels through channel 262, or to generate different emulsions that travel through channels 264, 266, and 268.

Droplet generator 280 is a butted tube generator that includes a first section of hollow tube 282 and a second section of hollow tube 284. Tube section 282 includes a fluid channel 286, and tube section 284 includes a fluid channel 288. The tube sections are separated by a small distance, forming an intersection region 290 between the tubes. Accordingly, if a foreground fluid flows toward intersection region 290 through channel 286, and a background fluid flows radially inward toward intersection region 290 from the region outside the tubes, an emulsion can be created and flow into channel 288.

The progression from droplet generator 200 through droplet generator 280 illustrates the relationship between these various droplet generators. Specifically, if the variable n is chosen to represent the number of radial fluid channels that intersect a longitudinal fluid channel at an intersection region within a tube, then droplet generator 200 may be characterized as an "n=1" cross-type droplet generator, droplet generator 240 may be characterized as an "n=2" cross-type droplet generator, droplet generator 260 may be characterized as an "n=3" cross-type droplet generator, and droplet generator 280 may be characterized as an "n=∞" cross-type droplet generator, because the gap between tubes 282 and 284 may be viewed as formed from an infinite number of radial fluid channels extending continuously around the circumference of a single elongate tube. Because droplet generator 280 is formed from two separate pieces of material, it would not typically be characterized as a continuous or continuous mode droplet generator.

III. Planar Mode Examples

This section describes examples of "planar mode" droplet generators, in which sample-containing droplets suspended in a background fluid are generated and transported substantially within a plane; see FIGS. 8-24. As used herein, "substantially within a plane" or "substantially planar" means that the radius of curvature of the space in which droplets are generated and transported is much greater than the cross-sectional dimensions of the channels through which the droplets are created and transported, and the curvature does not substantially alter the hydraulic function of the channels.

In some cases (see, e.g., FIGS. 8-17), well protrusions for sample-containing fluid, background fluid, and droplets may be integrally formed with a substantially planar substrate of the droplet generator. In other cases (see, e.g., FIGS. 18-24), the wells may be formed as one or more separate components, and configured to form a substantially fluid tight seal or interface with a substantially planar substrate of the droplet generator. In intermediate cases, some wells may be integrally formed with the substrate, and some may be formed as one or more separate components. Although the Figures focus on the cases where the wells are either entirely integrally formed with, or entirely separately formed from, the planar substrate, the intermediate possibilities are also contemplated by the present teachings.

Figure 8:
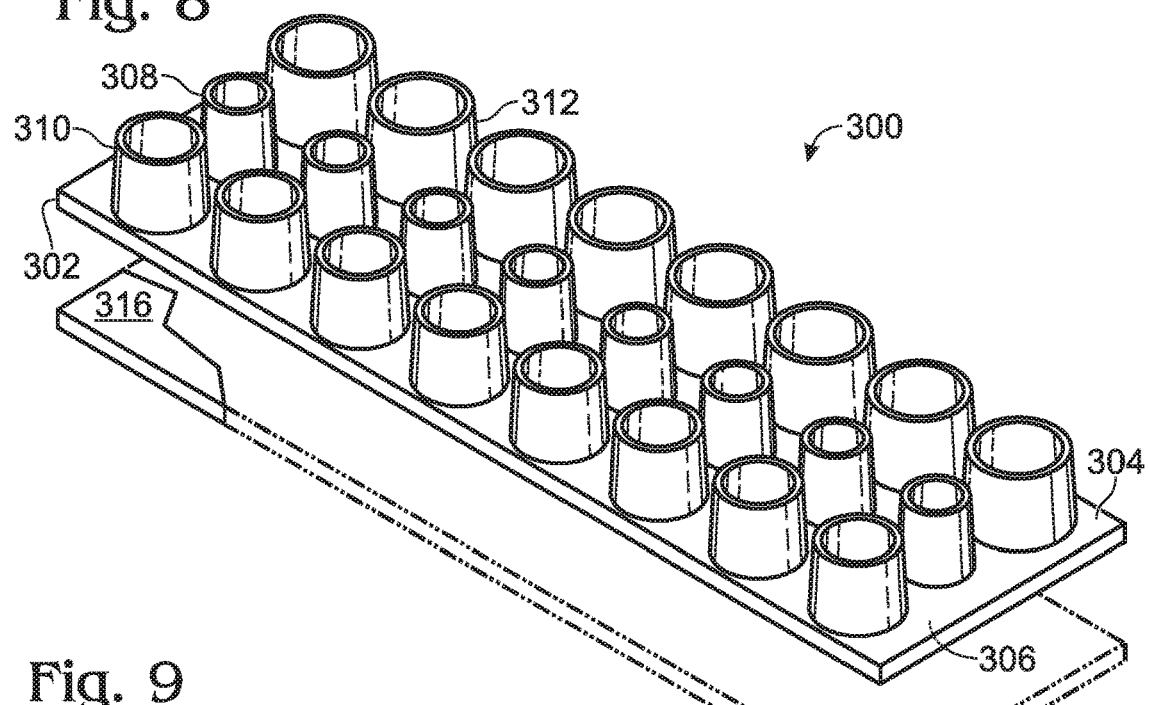
FIG. 8 is an isometric view of a top surface of a planar-mode droplet generation system, in accordance with aspects of the present disclosure.
Figure 9:
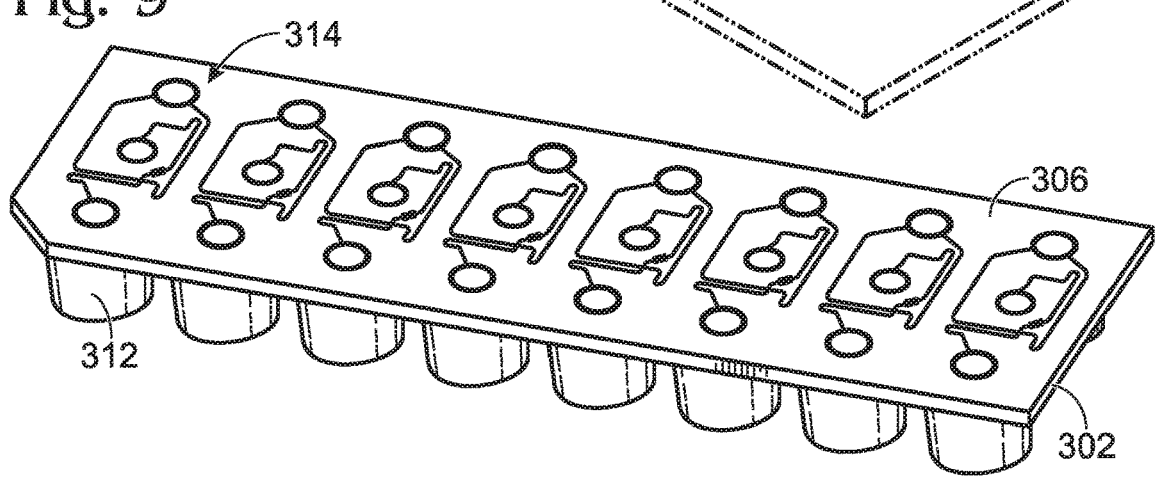
FIG. 9 is an isometric view of a bottom surface of the droplet generation system of FIG. 8.

FIG. 8 is a perspective view of a top surface of a planar-mode droplet generator, generally indicated at 300, in accordance with aspects of the present disclosure. FIG. 9 is a perspective view of a bottom surface of droplet generator 300 of FIG. 8. Droplet generator 300 includes a substantially planar substrate 302 having a top surface 304 and a bottom surface 306. In the embodiment of FIG. 8, a sample well 308, a background fluid well 310, and a droplet outlet region (which in this example takes the form of a droplet well 312) are integrally formed with substrate 302. A network of channels, generally indicated at 314, is formed in the bottom surface 306 of substrate 302 and fluidically interconnects the sample well, the background fluid well, and the droplet outlet region. In droplet generator 300, eight identical sets of wells and channels are shown. More generally, any desired number of wells and channels may be formed with substrate 302. The same principle holds true for all of the planar mode droplet generators described in Section III.

A sealing member 316 (shown in FIG. 8) is configured to be disposed adjacent to the bottom surface of substrate 302, to form a substantially fluid tight seal with the bottom surface of the substrate and thus with channel network 314. Although sealing member 316 is shown in FIG. 8 as a featureless, substantially planar member, in some cases the network of channels may be partially or entirely formed in the sealing member rather than exclusively in substrate 302. Regardless of whether the channel network is formed exclusively in the substrate, exclusively in the sealing member, or partially in each of those components, a fluid tight network of channels will be formed when the substrate and the sealing member are brought together. Furthermore, the sealing member can be a deformable film that can take on non-planar configurations when it is not bonded to the substrate.

As described in more detail below, a source of pressure will generally be applied at least to sample well 308 and background fluid well 310, and possibly also to droplet well 312, in order to generate droplets with droplet generator 300. Accordingly, wells 308, 310, and 312 should be configured to withstand the side forces expected when pressure is applied, as well as other expected forces such as the forces of integration with a pumping unit and the forces expected during shipping and handling. Wells 308, 310, and 312 therefore may have walls that are approximately 0.20 inches thick. More generally the well walls may have thicknesses in the approximate range from 0.04 to 0.40 inches thick, depending on the expected forces and the material from which droplet generator 300 is constructed.

Figure 10:
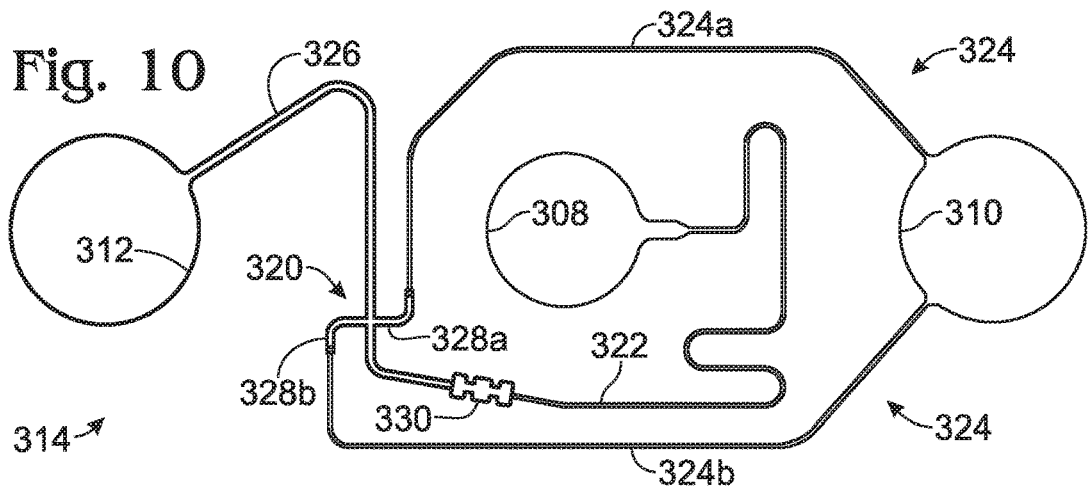
FIG. 10 is a magnified view of a portion of the bottom surface of the droplet generation system shown in FIG. 9.

FIG. 10 is a magnified view of a portion of bottom surface 306 of substrate 302, showing further details of channel network 314. Channel network 314 defines a droplet generation region indicated at 320, which is configured to generate sample-containing droplets suspended in the background fluid. More specifically, droplet generation region 320 is defined by the intersection of a first channel 322, a second channel 324, and a third channel 326. First channel 322 is configured to transport sample-containing fluid from sample well 308 to droplet generation region 320, second channel 324 is configured to transport background fluid from background fluid well 310 to droplet generation region 320, and third channel 326 is configured to transport sample-containing droplets from droplet generation region 320 to droplet well 312. Droplets are formed at droplet generation region 320 according to principles that have already been described; see, e.g., FIG. 1 and accompanying discussion above.

Channel network 314 includes various features that can be selected or changed to affect the droplet generation accomplished by droplet generator 300. For example, second channel 324, which transports background fluid from background fluid well 310 to droplet generation region 320, may (as depicted in FIGS. 9-10) include two background fluid sub-channels 324*a*, 324*b*, which intersect first channel 322 from two different directions. As a result of the intersection of sub-channels 324*a*, 324*b* with first channel 322 and third channel 326, droplet generation region 320 is formed as a cross-shaped intersection region.

When two background fluid sub-channels are used, the two sub-channels may be configured to have substantially equal hydraulic resistances, so that the rate of background fluid flow through each sub-channel is substantially the same. This may be accomplished, for example, by giving the sub-channels approximately equal lengths, or by adjusting other parameters of the sub-channels such as their diameters and/or inner surface characteristics. Furthermore, the two sub-channels may include enlarged portions 328*a*, 328*b* in a portion of each sub-channel adjacent to the droplet generation region. These enlarged channel portions may, for example, affect the size of droplets that are generated. More generally, the sizes of the channels remote from the cross can be made bigger or smaller to control the resistance to flow in each channel, and thus the flow rate. The two oil channels are sized (width, depth, length) to give the same resistance so that their flow rates are substantially equal. The relative sizes of the oil and sample channels are selected to give a desired sample to oil flow rate.

As FIG. 10 depicts, channel network 314 also includes an air trap 330 disposed along first channel 322, between sample well 308 and droplet generation region 320. Air trap 330, which can take various forms, is generally configured to prevent sample-containing fluid from being inadvertently drawn through first channel 322 by capillary action or other forces. Essentially, air trap 330 functions as a simple valve, to stop the flow of sample-containing fluid through first channel 322 until a desired time. This feature may be desirable to avoid uncontrolled emulsion formation.

More generally, air traps according to the present teachings function by pinning a liquid/air interface at a location where the channel cross-section abruptly increases in one or more dimensions. This has the effect of locally increasing the effective contact angle of the liquid/channel wall interface to a value greater than 90 degrees, which results in a local force that stops further liquid movement. The operation of the device therefore consists of loading sample into a dry device before the oil is loaded. The sample flows through its channel (by gravity plus capillarity) to the air trap, where the flow stops due to the channel expansion at that point. Oil is then loaded and flows through its channels (by gravity plus capillarity) to the cross. Once oil reaches the cross, any air remaining in the air trap (and the channel between the air trap and cross) is trapped between the sample and oil and prevents the two fluids from prematurely coming into contact. Some oil can flow toward the air trap, being drawn along the corners of the channel by capillary forces; it bypasses the trapped air. The contraction/expansion features in the air trap slow the advance of this oil because capillary forces are reduced when the channel dimensions are expanding. The final result is that the air trap keeps the sample and oil substantially separated until a fluidic driving force is applied. This feature is desirable to avoid the uncontrolled emulsion formation that would occur if the oil and sample were allowed to mix prematurely.

Figure 11:
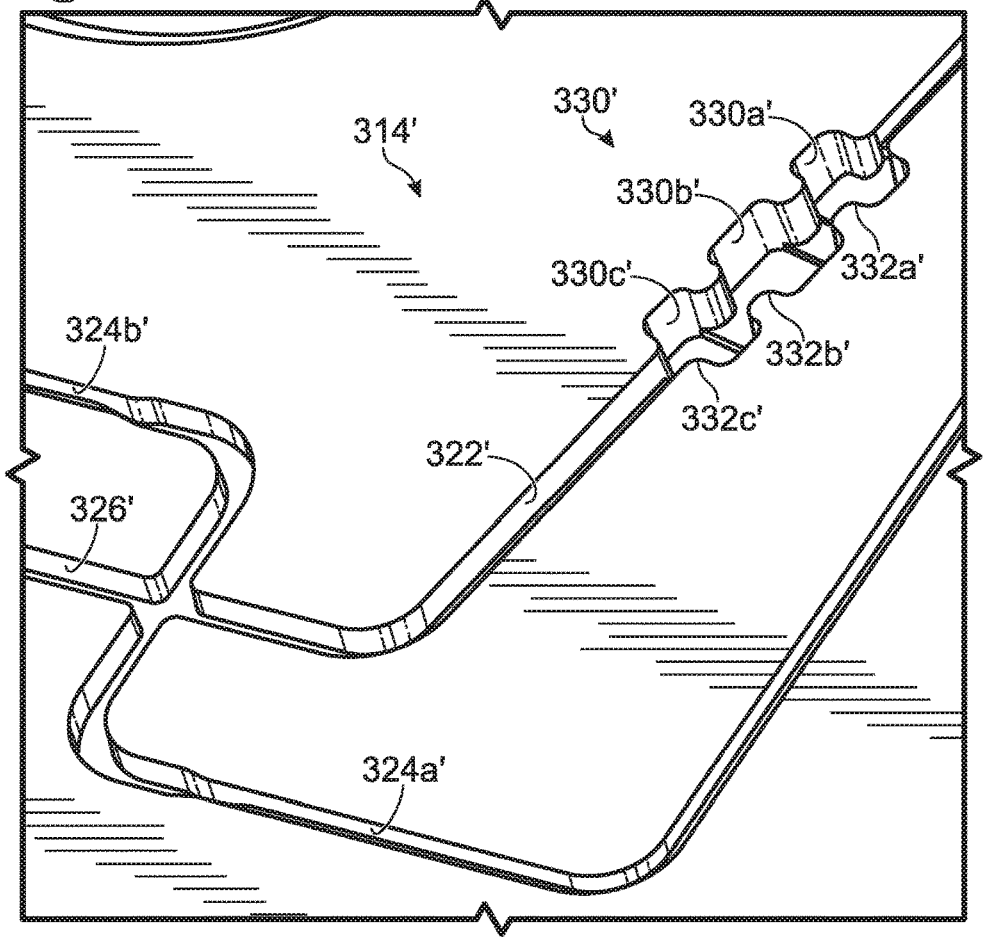
FIG. 11 is a magnified view of an air trap region suitable for use with a planar-mode droplet generation system, in accordance with aspects of the present disclosure.
Figure 12:
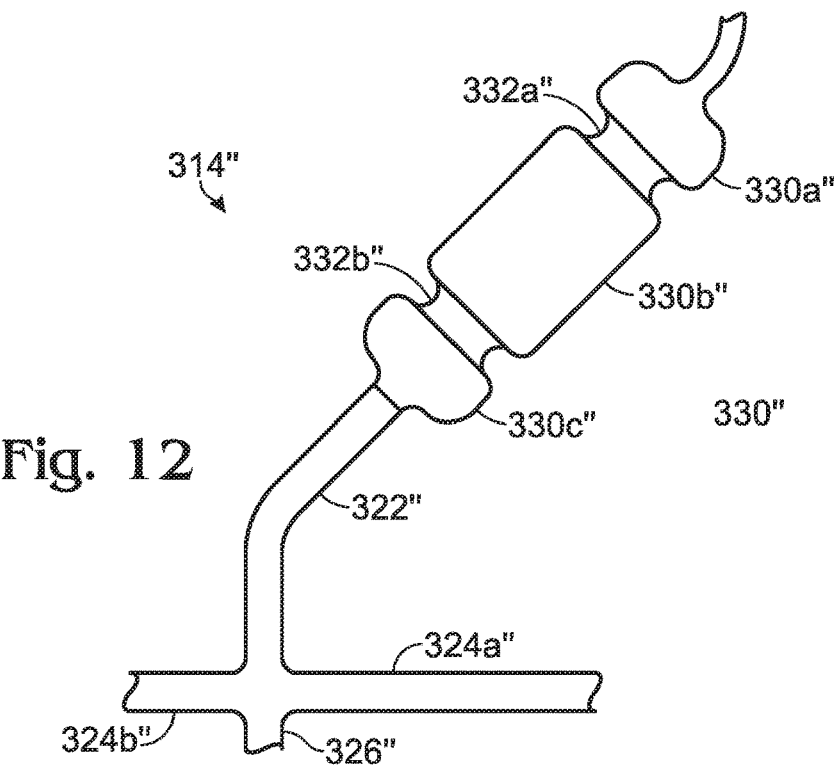
FIG. 12 is a magnified view of another air trap region suitable for use with a planar-mode droplet generation system, in accordance with aspects of the present disclosure.

FIGS. 11-12 depict exemplary air trap embodiments that may be suitable for use with a droplet generation system such as droplet generator 300, in accordance with aspects of the present teachings. More specifically, FIG. 11 shows portions of a channel network 314', including a first channel 322', sub-channels 324a', 324b' of a second channel 324', a third channel 326', and an exemplary air trap 330' disposed along channel 322'. In the example depicted in FIG. 11, components represented by primed reference numbers are configured to perform functions similar to the objects represented by corresponding unprimed reference numbers in FIG. 10. Air trap 330' includes three sections 330a', 330b', 330c', each of which includes at least one bent angle 332a', 332b', 332c' around which sample-containing fluid must pass in order to pass entirely through air trap 330'. These locations where the channel changes in width and in depth create additional sites for stopping fluid flow by the capillary pinning mechanism described above.

FIG. 12 shows portions of a channel network 314", including a first channel 322", sub-channels 324a", 324b" of a second channel 324", a third channel 326", and an exemplary air trap 330" disposed along channel 322". In the example depicted in FIG. 12, components represented by double primed reference numbers are configured to perform functions similar to the objects represented by corresponding unprimed reference numbers in FIG. 10. Like air trap 330', air trap 330" includes three sections 330a", 330b", 330c". However, rather than including bent angles, the three sections of air trap 330" are separated from each other by a pair of narrowed neck regions 332a", 332b". Like the bent angles of air trap 330', these neck regions serve to create additional sites for stopping fluid flow by capillary pinning, to better prevent inadvertent flow of sample-containing fluid. Many configurations of air traps are possible, and the exact configuration may be chosen to result in a desired amount of resistance to capillary flow. Furthermore, although the term "air trap" has been used, this does not imply that air must actually be trapped under all circumstances. In some cases, the shape of the air trap may serve to prevent undesirable fluid flow, even if there is no air trapped in the "air trap."

Figure 13:
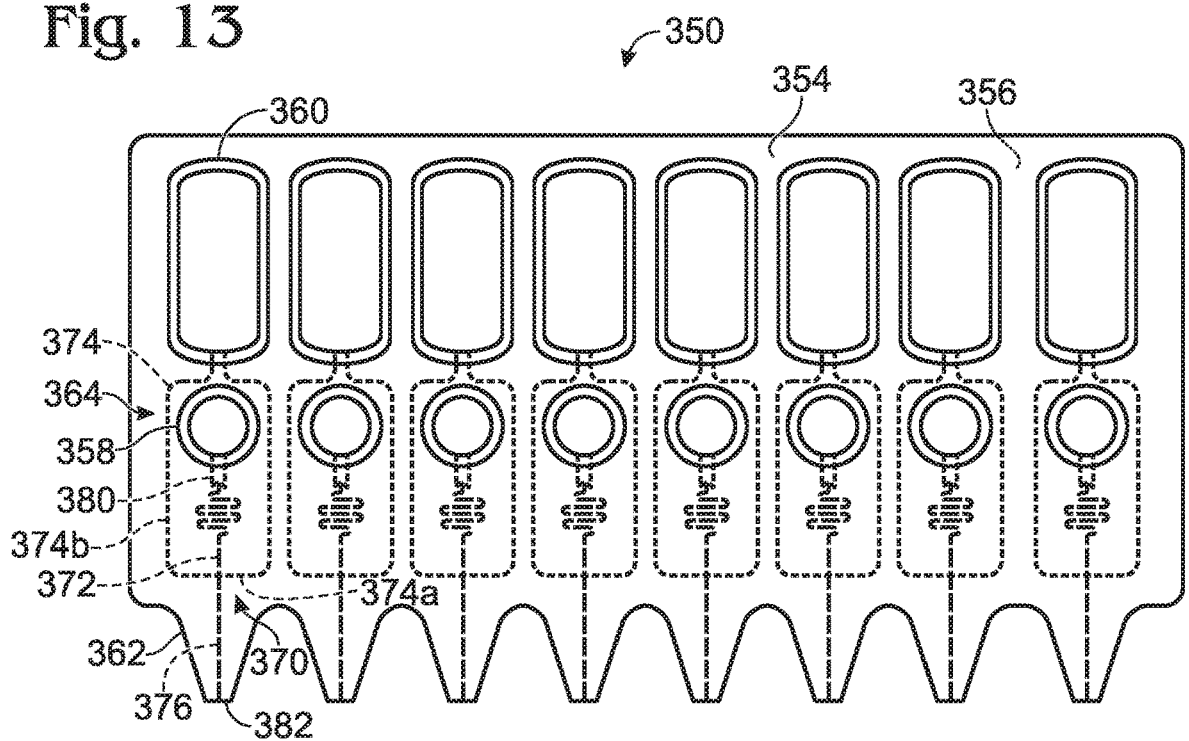
FIG. 13 is a semi-transparent top view of another exemplary droplet generation system, in accordance with aspects of the present disclosure.

FIG. 13 is a semi-transparent top view of another exemplary droplet generator, generally indicated at 350, in accordance with aspects of the present disclosure. Droplet generator 350 includes a substantially planar substrate 352 having a top surface 354 and a bottom surface 356. A sample well 358 and a background fluid well 360 are integrally formed with substrate 352. A droplet outlet region, which in this example takes the form of a pipette tip 362, may be integrally formed with substrate 352, or in some cases may be formed separately and integrated with the substrate, as described in more detail below. A network of channels, generally indicated at 364, is formed in the bottom surface 356 of substrate 352 and fluidically interconnects the sample well, the background fluid well, and the pipette tip.

As used herein, the terms "pipette" and "pipette tip" are not intended to be limited to the structure shown in FIG. 13 or any of the other drawings. More generally, these terms are intended to mean a droplet outlet region that is capable of conveying droplets from a droplet generator to an accumulation vessel, or in some cases a sample inlet region that is capable of conveying sample-containing fluid to a sample well or a sample inlet channel. A pipette tip can be in the form of a channel. It can be formed separately from a droplet generator housing such as a substrate, in which case the pipette tip can mate with the substrate to convey droplets from the droplet generator to another vessel, or to convey sample fluid to the droplet generator. It can also be integrally formed with the droplet generator, as in FIG. 13. An accumulation vessel suitable for use in conjunction with a pipette can be any container suitable for accumulating droplets. In particular, the accumulation vessel can be the well of a microtiter plate or a PCR plate. Pipette tip, as used in this disclosure, can also be a tip that is used with, e.g., a handheld or automated pipettor.

As in the case of droplet generator 300 described previously, a substantially planar sealing member (not shown) may be configured to be disposed adjacent to the bottom surface of substrate 352, to form a substantially fluid tight seal with the bottom surface of the substrate and thus with channel network 364. The sealing member may be a featureless planar member, or the network of channels may be partially or entirely formed in the sealing member rather than exclusively in substrate 352. In any case, a fluid tight network of channels will be formed when the substrate and the sealing member are brought together. Furthermore, in some cases, channel network 354 may be integrally formed and/or sealed within substrate 352 in a fluid tight manner, in which case there may be no sealing member provided.

Wells 358 and 360 configured to withstand the forces expected when pressure is applied, when the droplet generator integrated with a pumping unit, and when the droplet generator is handled and shipped to a customer or other destination. Accordingly, wells 358 and 360 may be similar in their characteristics to previously described wells 308, 310, and 312, i.e., wells 358 and 360 may have thicknesses in the approximate range from 0.04 to 0.40 inches thick, depending on the expected forces and the material from which droplet generator 350 is constructed. Similarly, pipette tips 362 will generally be constructed to withstand these same forces. As mentioned previously, in some cases, pipette tips 362 may be integrally formed with substrate 352, for example in an injection molding process. In other cases, the substrate may be formed with suitable apertures or other connection structures (not shown in FIG. 13) configured to receive suitably modified, standard pipette tips in a fluid tight manner.

Channel network 364 defines a droplet generation region indicated at 370, which is configured to generate sample-containing droplets suspended in the background fluid. As in the case of previously described droplet generation regions 320, each droplet generation region 370 is defined by the intersection of a first channel 372 configured to transport sample-containing fluid from sample well 358 to droplet generation region 370, a second channel 374 configured to transport background fluid from background fluid well 360 to droplet generation region 370, and a third channel 376 configured to transport sample-containing droplets from droplet generation region 370 to pipette tip 362. Droplets are formed in region 370 according to principles that have been described in detail above.

Also as described previously, second channel 374 includes two background fluid sub-channels 374a, 374b, which intersect first channel 372 from two different directions to form a cross-shaped droplet generation region. Sub-channels 374a, 374b have approximately equal lengths, so that they have substantially equal hydraulic resistances and the rate of background fluid flow through each sub-channel is substantially the same. In addition, an air trap 380 is disposed along first channel 372, between sample well 358 and droplet generation region 370, and is configured to prevent sample-containing fluid from being inadvertently drawn through first channel 372 by capillary action or other forces. Accordingly, droplets will be formed only when suitable pressures are applied to the sample wells, the background fluid wells, and/or the pipette tips, in which case the formed droplets will be transported through channels 376 to pipette tips 362, and emitted from apertures 382 formed in the pipette tips. The emitted sample-containing droplets then may be collected and/or further transported for additional processing steps such as thermocycling.

Figure 14:
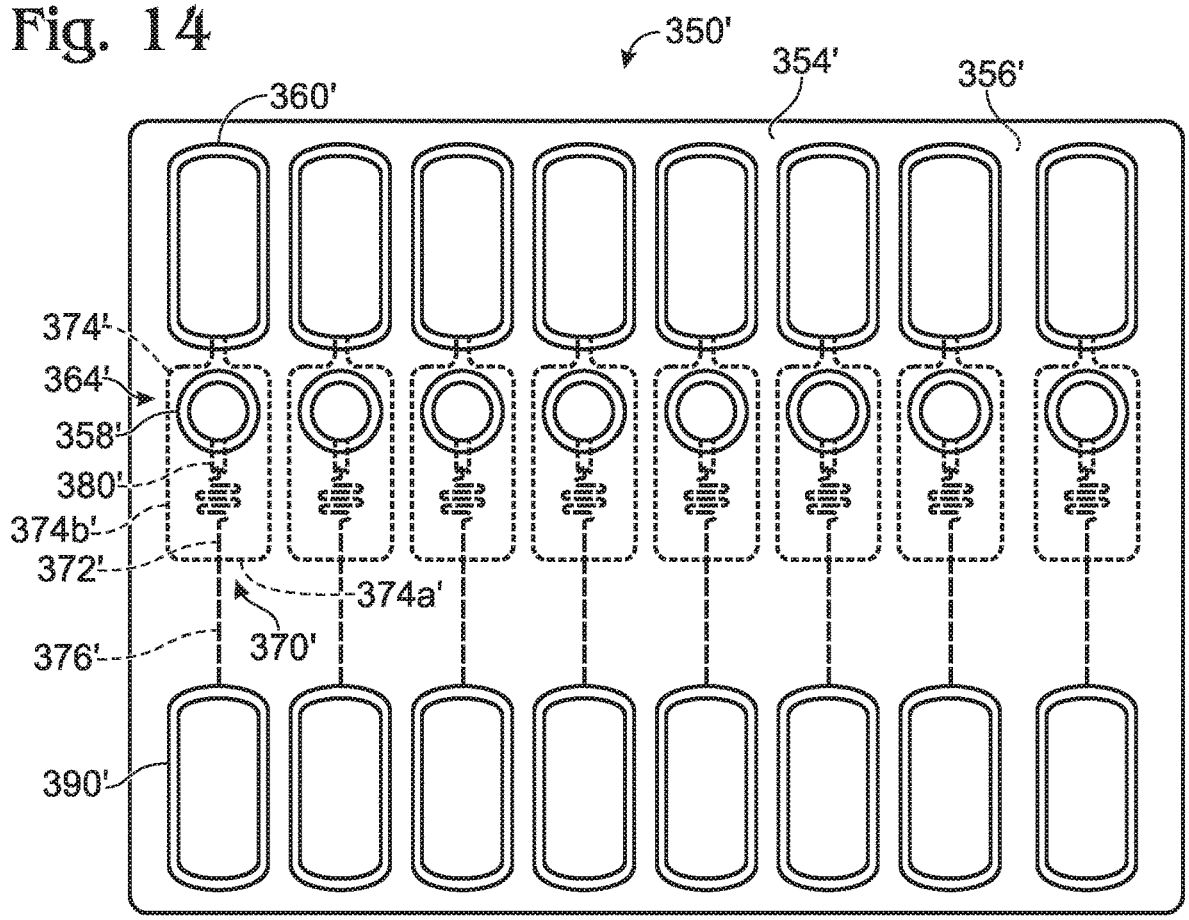
FIG. 14 is a semi-transparent top view of yet another exemplary droplet generation system, in accordance with aspects of the present disclosure.

FIG. 14 is a semi-transparent top view of yet another exemplary droplet generator, generally indicated at 350', in accordance with aspects of the present disclosure. Droplet generator 350' is substantially similar to droplet generator 350 in most respects. Accordingly, primed reference numbers in FIG. 14 represent substantially the same components as their unprimed counterparts in FIG. 13, and those components will not be described again here. However, droplet generator 350' of FIG. 14 differs from droplet generator 350 of FIG. 13 in the following respect.

Rather than pipette tips 362 and corresponding apertures 382, third channels 376' of droplet generator 350' transport sample-containing droplets to droplet wells 390', which collect the droplets in a manner similar to droplet wells 312 of droplet generator 300. Thus, droplet generators 350 and 350' may be viewed as slight variations of each other, with each best suited for a particular application or class of applications. Furthermore, these examples show that the droplet wells of any of the other planar mode droplet generator embodiments described herein may be replaced with pipette tips under appropriate circumstances.

Figure 15:
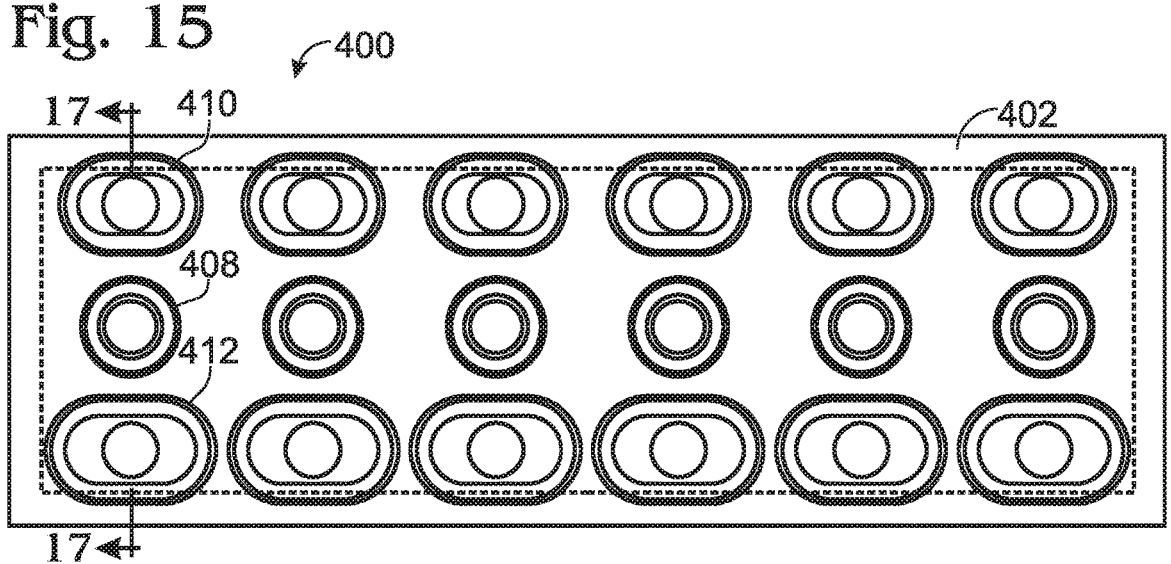
FIG. 15 is a top view of still another exemplary droplet generation system, in accordance with aspects of the present disclosure.
Figure 16:
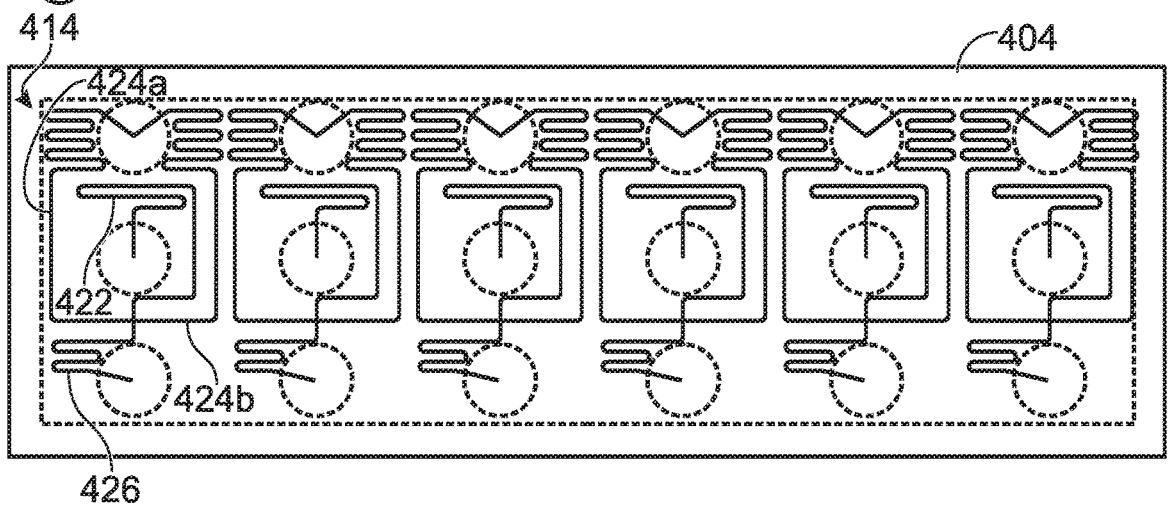
FIG. 16 is a bottom view of the droplet generation system of FIG. 15.
Figure 17:
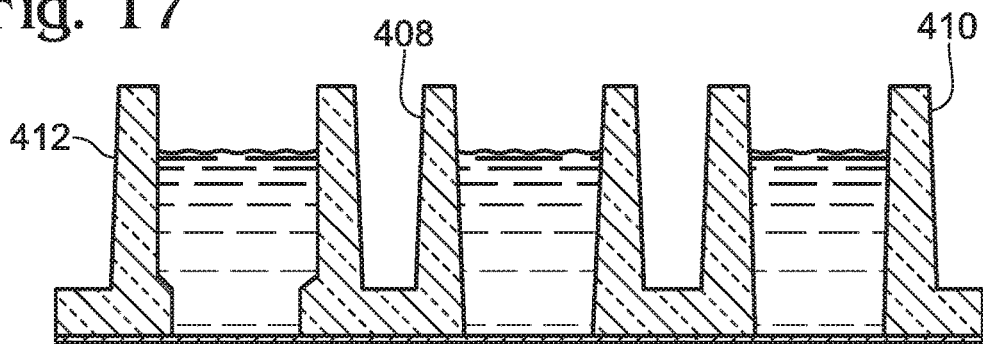
FIG. 17 is a sectional view taken along the line 17-17 in FIG. 16.

FIG. 15 is a top view of still another exemplary planar mode droplet generator, generally indicated at 400, in accordance with aspects of the present disclosure, and FIG. 16 is a bottom view of droplet generator 400. FIG. 17 is a sectional view of droplet generator 400 taken along the line 17-17 in FIG. 15. Droplet generator 400 includes the same general components as droplet generator 300, and reference numbers starting with 400 in FIGS. 15-16 represent substantially the same components as their counterparts starting with 300 in FIGS. 8-10. Aside from the features of droplet generator 400 either not included in droplet generator 300 or not discussed in the description of droplet generator 300, those components will not be described again here.

Several features of droplet generator 400 exemplify features that may be adopted in any of the planar mode droplet generators described herein. Specifically, FIG. 15 depicts background fluid wells 410 and droplet wells 412 as having an oval cross section near the top of each well, whereas sample wells 408 have a circular cross section. An oval shape, as opposed to a circular upper cross section, may facilitate fluid tight connections between the wells and other components of an overall assay system, such as pump interfaces. The use of an oval shape is merely exemplary. In general, the upper portion of each well may be given any desired shape in a particular droplet generator, to best facilitate the integration of the droplet generator with the other portions of the assay system.

In addition, as can be best seen in FIG. 17, one or more of the wells of a droplet generator according to the present teachings, in this case droplet wells 412, may have a stepped vertical cross section in which the well becomes narrower toward the bottom in a stepped fashion. On the other hand, also as depicted in FIG. 17, other wells, such as sample wells 408 and background fluid wells 410, may have smoothly tapered vertical cross sections, which also become narrow toward the bottom of the wells. The use of stepped and/or smoothly tapered vertical well cross sections may facilitate the manufacture of injection molded planar mode droplet generators.

The depicted cross sections also may have other advantages, such as the following. The steps or other features in the well bottoms can guide a fluid dispenser, such as a pipette tip, to a position in the well that is optimal for liquid transfer in and out of the device. Without such features, a pipette tip could, for instance, be inserted such that, during liquid addition, the liquid is injected directly into the channels. Likewise, features in a droplet well can allow a pipette tip to be conveniently positioned a fixed distance from the well bottom, allowing droplet to be aspirated without being damaged while flowing through a "pinch" between the pipette tip and well bottom.

Smoothly tapered well walls may help to facilitate drainage of the sample toward the well bottoms, which leaves less residual sample in the well, and increases the efficiency of sample conversion to droplets. Samples are often precious, and high sample conversion efficiency is a valuable feature. The use of smoothly tapered walls may result in a sample loss of less than 0.5 uL, or even less than 0.3 nL. For a 20 uL sample, the conversion efficiency is then over 95%.

FIG. 16 illustrates a network of fluid channels 414 that differs slightly from its counterpart network 314 of droplet generator 300. Specifically, first channel 422, which is configured to transport sample-containing fluid from sample well 408 to droplet generation region 420, does not include an air trap. As described previously, an air trap may be used in some cases to help prevent unwanted fluid transport from the sample well to the droplet generation region. However, as depicted in FIG. 16, an air trap may not always be necessary. This may be the case, for example, if the channel between the sample well and the droplet generation region is given a hydraulic resistance sufficient to prevent unwanted fluid flow. As depicted for channel 422 of droplet generator 400, this may be accomplished if the channel has sufficient length, a great enough number of bends, a small enough diameter, and/or is given other characteristics (such as an appropriately coated inner surface) to raise its hydraulic resistance to a desired level.

Aside from giving channel 422 hydraulic resistance sufficient to avoid unwanted transport of sample-containing fluid, FIG. 16 also shows how the various channels of network 414 may be given hydraulic resistances resulting in a desired rate of droplet production. More specifically, each of channels 422, 424 (including sub-channels 424a, 424b), and 426 may be configured to have any desired hydraulic resistance, by giving those channels desired lengths and/or other suitably chosen characteristics. In this manner, the overall hydraulic resistance of channel network 414 may be tuned to any desired level, to result in a predetermined flow rate of sample-containing droplets into droplet wells 412 for a given set of applied pressures. These same principles may be applied to any droplet generation system according to the present teachings.

Figure 18:
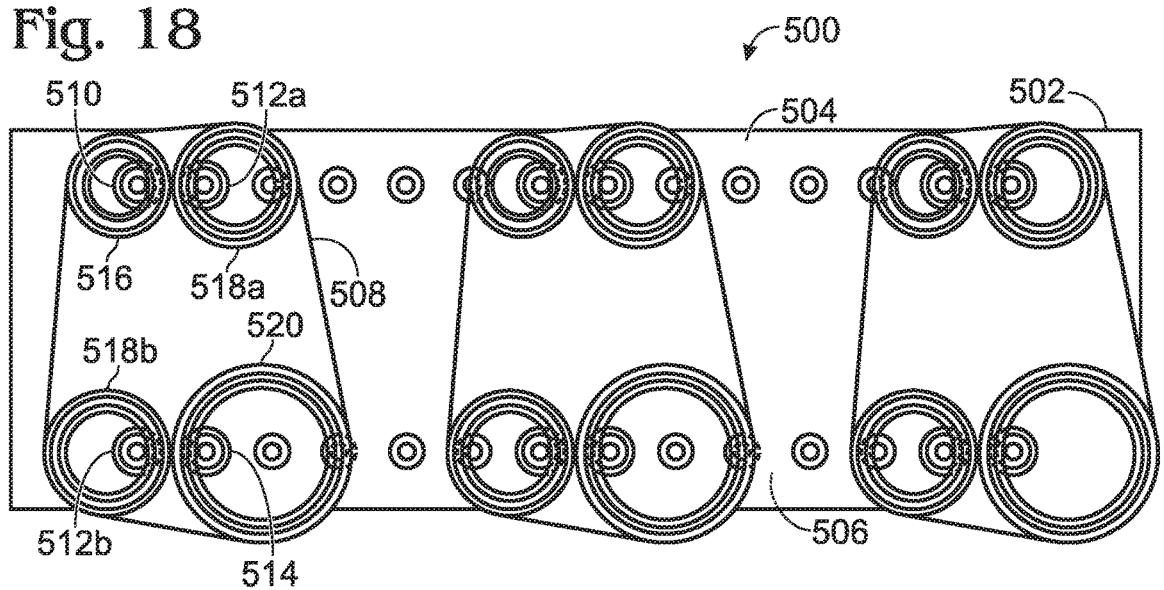
FIG. 18 is a top view of yet another exemplary droplet generation system, in accordance with aspects of the present disclosure.
Figure 19:
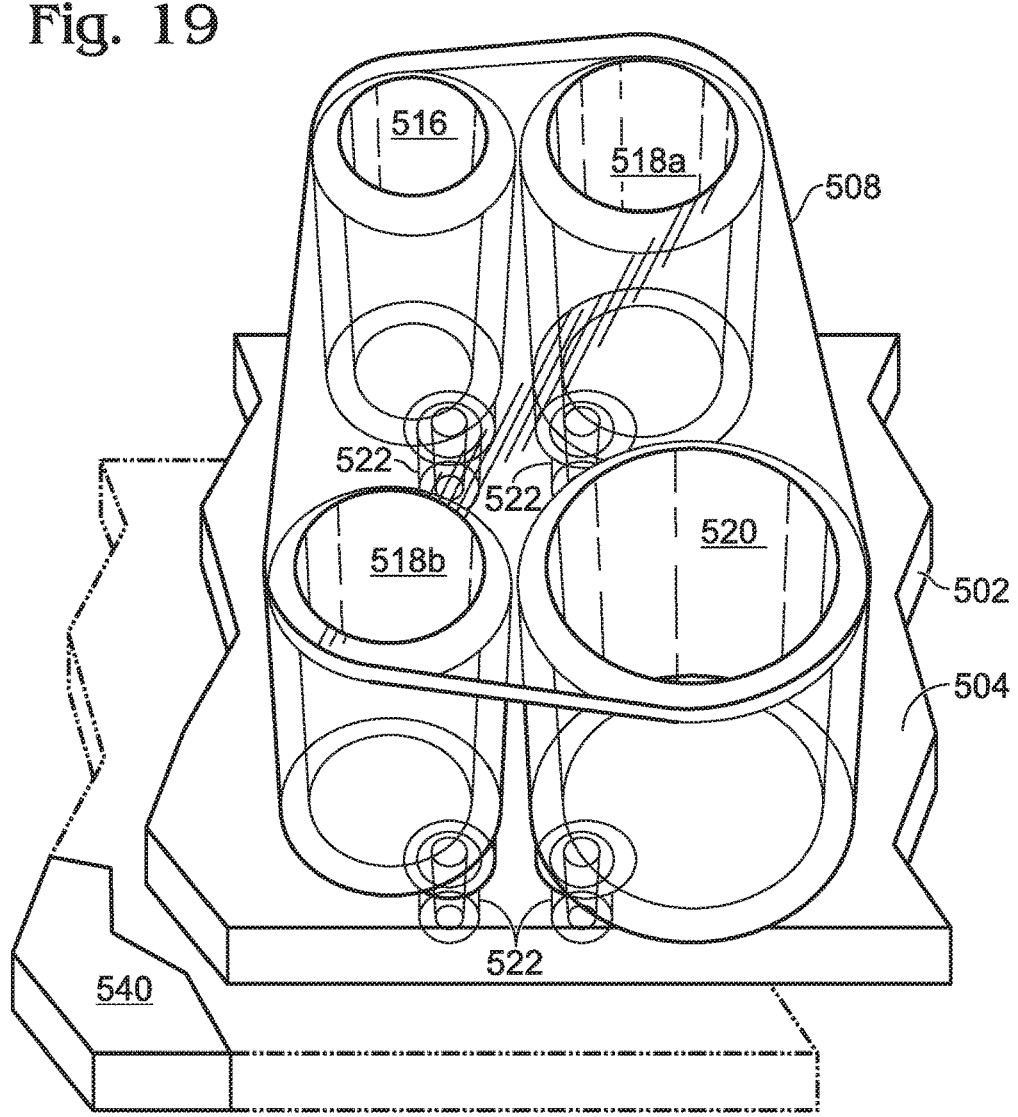
FIG. 19 is an isometric view of a magnified portion of the droplet generation system of FIG. 18.
Figure 24:
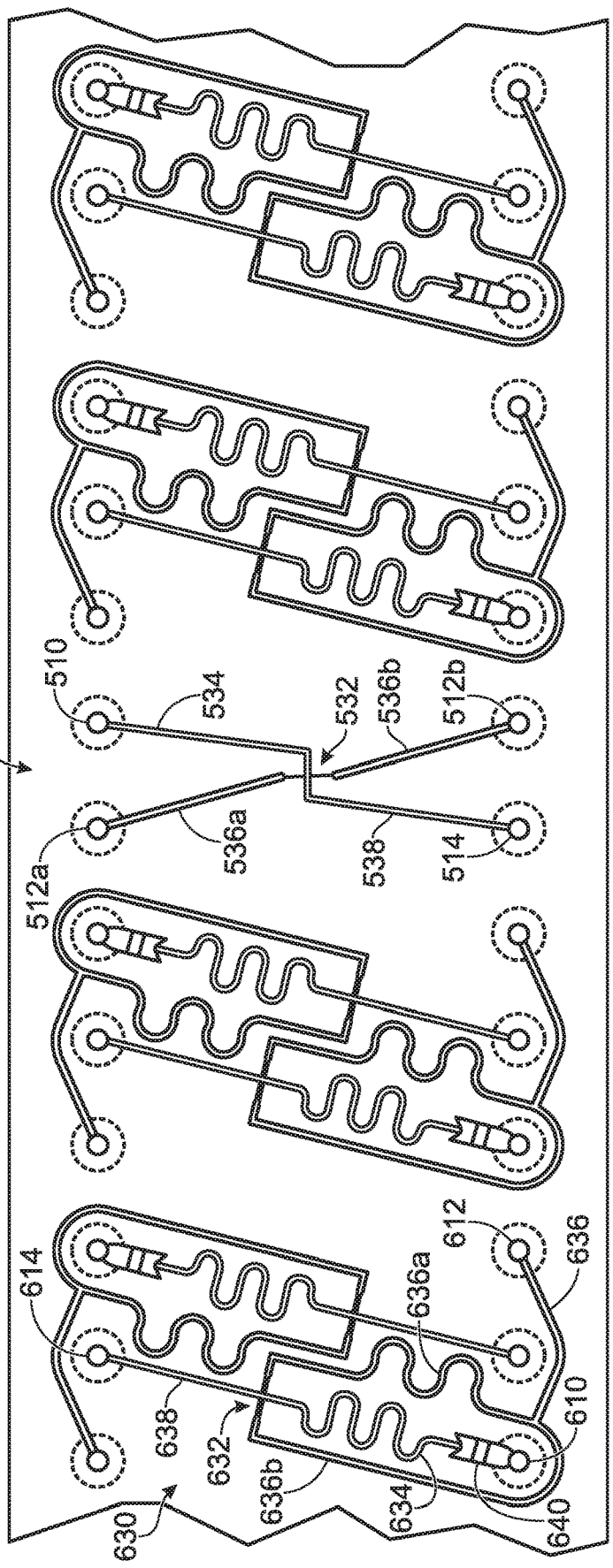
FIG. 24 is a bottom view of a portion of a droplet generation system according to the present teachings, showing channel networks suitable for use in conjunction with some of the other systems described herein.

FIGS. 18, 19, and 24 depict a first example of a planar mode droplet generator, generally indicated at 500, in which a planar substrate and a well vessel are formed as separate components. A benefit of this design is that a variety of well sizes can be used with a single droplet generator base. It also permits replacement of, e.g., the sample and oil wells with syringe pumps containing those liquids. This enables, for instance, "bulk" droplet generation on the mL scale versus the typical uL scale.

FIG. 18 is a top view of droplet generator 500, and FIG. 19 is a magnified perspective view of a portion of the droplet generator. Droplet generator 500 includes a substantially planar substrate 502 having a top surface 504 and a bottom surface 506, and a separate well vessel 508 configured to be connected to substrate 502 to form a functional droplet generator. Although in the depicted examples, all of the fluid wells associated with the droplet generator are formed in a well vessel, in alternative configurations contemplated by the present teachings, one or more of the sample well, background fluid well(s), and droplet well may be integrally formed with the substrate (as in previously described embodiments), while the remainder of the wells are included in the well vessel.

To accommodate a connection with well vessel 508, top surface 504 of substrate 502 includes various ports configured to receive complementary portions of the well vessel. Specifically, a sample port 510, a pair of background fluid ports 512a, 512b, and a droplet outlet port 514 are all formed in top surface 504 of substrate 502. In droplet generator 500, each of these ports takes the form of a substantially cylindrical aperture, but any desired shape may be used for the ports. Well vessel 508 includes a sample well 516 configured to make a substantially fluid tight connection with sample port 510, a pair of background fluid wells 518a, 518b configured to make a substantially fluid tight connection with background fluid ports 512a, 512b, and a droplet outlet well 520 configured to make a substantially fluid tight connection with droplet outlet port 514.

To accomplish a fluid tight connection between each well and its associated port, each well includes a cylindrical attachment protrusion 522 configured to fit securely and in a fluid tight manner within the corresponding port. When the ports are given shapes other than cylindrical, the attachment protrusions of the well vessel will be given appropriate complementary shapes. Furthermore, according to the present teachings, the attachment between the ports and the wells may be made in many different ways. For example, in contrast to the depiction of FIGS. 18-19, the "male" portions of the attachment mechanisms (i.e., the protrusions) may be associated with the ports, and the "female" portions of the attachment mechanisms (i.e., the complementary apertures) may be associated with the wells, for some or all of the wells. In any case, the ports and/or the wells may be provided with various elements such as o-rings, compression plates, or elastic apertures, to facilitate a fluid tight connection between the substrate and the well vessel. For instance, a short length of Tygon elastic tubing, sold by the Saint-Gobain Corporation of France, may fit snugly on the outsides of the "male" portions of any attachment mechanisms.

FIG. 24 depicts the bottom surface of the droplet generator, with a possible sealing member (described below) removed for clarity. As depicted in the central portion of FIG. 24, a network of channels, generally indicated at 530, is formed in the bottom surface 506 of substrate 502. Network 530 is configured to fluidically interconnect sample port 510, background fluid ports 512a, 512b, and droplet outlet port 514. A droplet generation region 532 is defined by network of channels 530 and configured to generate sample-containing droplets suspended in the background fluid. More specifically, droplet generation region 532 is defined by the intersection of a sample channel 534, a pair of background fluid channels 536a, 536b, and droplet channel 538. Sample channel 534 is configured to transport sample-containing fluid from sample port 510 to droplet generation region 532, background fluid channels 536a, 536b are respectively configured to transport background fluid from background fluid ports 512a, 512b to droplet generation region 532, and droplet channel 538 is configured to transport sample-containing droplets from droplet generation region 532 to droplet outlet port 514.

As depicted in FIG. 19, a substantially planar sealing member 540 may be provided with droplet generator 500. As in the case of the other planar mode embodiments, sealing member 540 may be attached to substrate 502 by compression, adhesion, heat sealing, or any other suitable attachment mechanism, to make channel network 530 fluid tight. Also as described previously, in some cases the channel network may be formed partially or entirely in the sealing member rather than in the bottom surface of the substrate. Furthermore, any other desired features may be introduced into channel network 530, such as increased channel lengths, changes in channel diameter and/or cross section, or an air trap disposed between the sample port and the droplet generation region, to control the timing and rate of droplet generation as described above.

Figure 20:
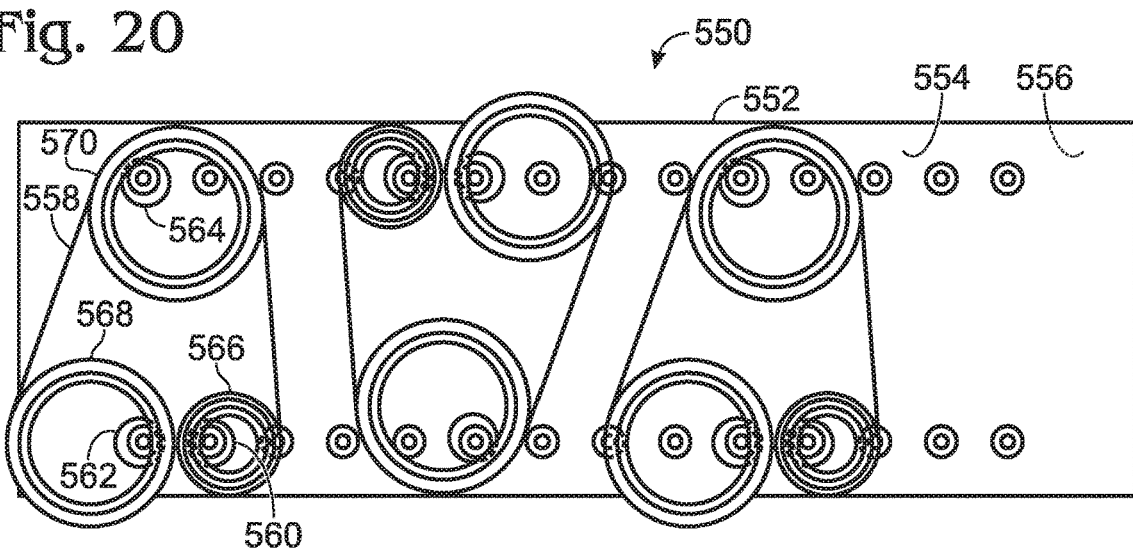
FIG. 20 is a top view of still another exemplary droplet generation system, in accordance with aspects of the present disclosure.
Figure 21:
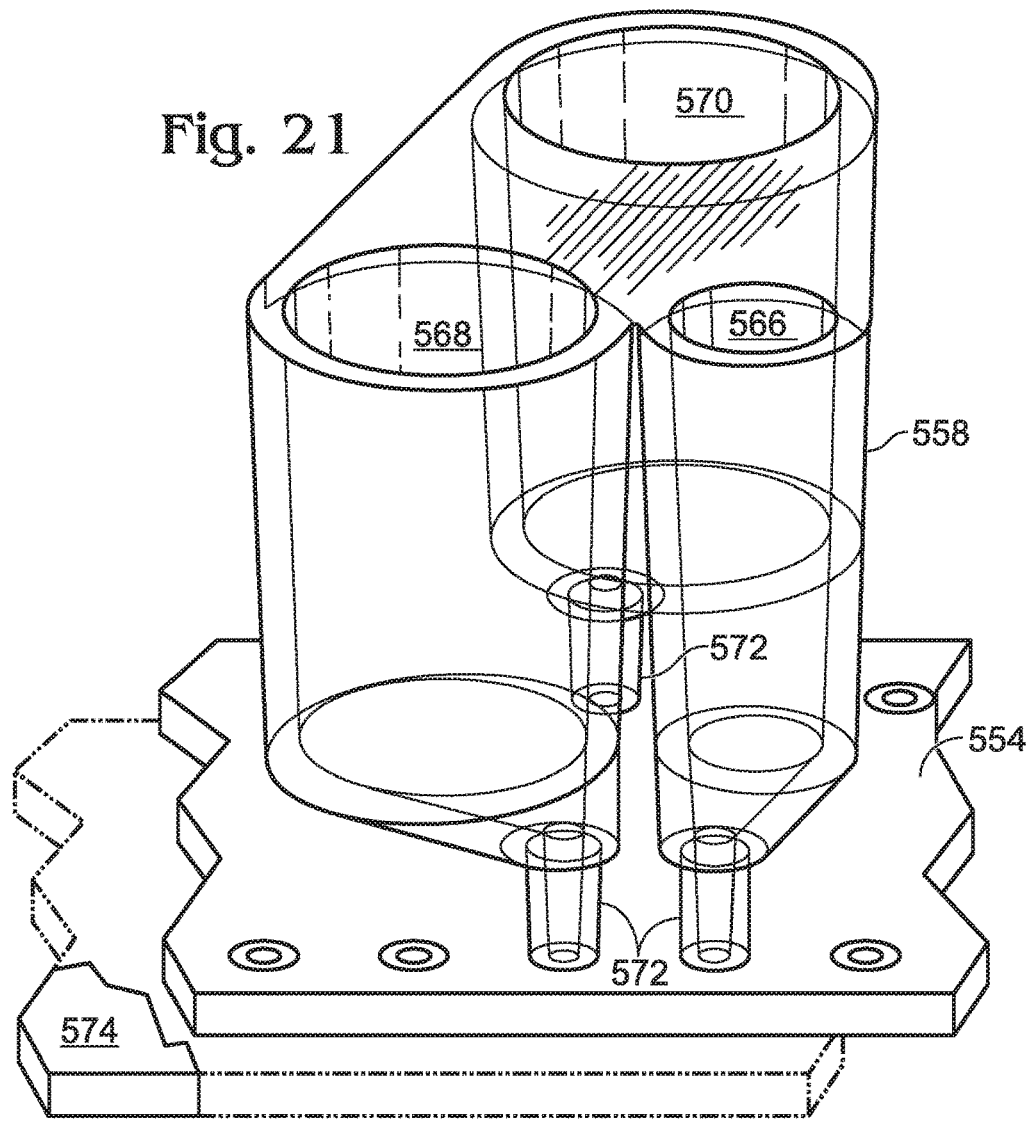
FIG. 21 is an isometric view of a magnified portion of the droplet generation system of FIG. 20.

FIGS. 20-21 depict another example of a planar mode droplet generator, generally indicated at 550, in which a planar substrate and a well vessel are formed as separate components. FIG. 20 is a top view of droplet generator 550, and FIG. 21 is a magnified perspective view of a portion of the droplet generator. Droplet generator 550 is similar in many respects to droplet generator 500 depicted in FIGS. 18-19, and accordingly some of the common features of droplet generator 550 and droplet generator 500 will not be described again in detail.

Droplet generator 550 includes a substantially planar substrate 552 having a top surface 554 and a bottom surface 556, and a separate well vessel 558 configured to be connected to substrate 552 to form a functional droplet generator. In this example, however, well vessel 558 has only three wells, rather than four as in the case of droplet generator 500. To accommodate a connection with well vessel 558, top surface 554 of substrate 552 includes ports configured to receive complementary portions of the well vessel. Specifically, a sample port 560, a background fluid port 562, and a droplet outlet port 564 are all formed in top surface 554 of substrate 552. Each of these ports takes the form of a substantially cylindrical aperture, but any desired shape may be used.

Well vessel 558 includes a sample well 566 configured to make a substantially fluid tight connection with sample port 560, a background fluid well 568 configured to make a substantially fluid tight connection with background fluid port 562, and a droplet outlet well 570 configured to make a substantially fluid tight connection with droplet outlet port 564. As in the case of droplet generator 500, regardless of the shapes of the ports, each well includes a complementary protrusion 572 configured to fit securely and in a fluid tight manner within the corresponding port. Furthermore, the connection between the ports and the wells may be made in many different ways, and may include various components configured to facilitate a fluid tight connection, as described previously with respect to droplet generator 500.

As depicted in FIG. 21, a substantially planar sealing member 574 may be provided with droplet generator 550. As in the case of the other planar mode embodiments, sealing member 574 may be attached to substrate 552 by any suitable attachment mechanism. Also as described previously, a network of channels (not shown) may be formed in the substrate, or may be formed partially or entirely in the sealing member, to fluidically interconnect the sample port, the background fluid port, and the droplet outlet port. This network of channels will generally provide a droplet generation region configured to generate sample-containing droplets in the background fluid, and may include any suitable characteristics of the other channel networks described herein.

Figure 22:
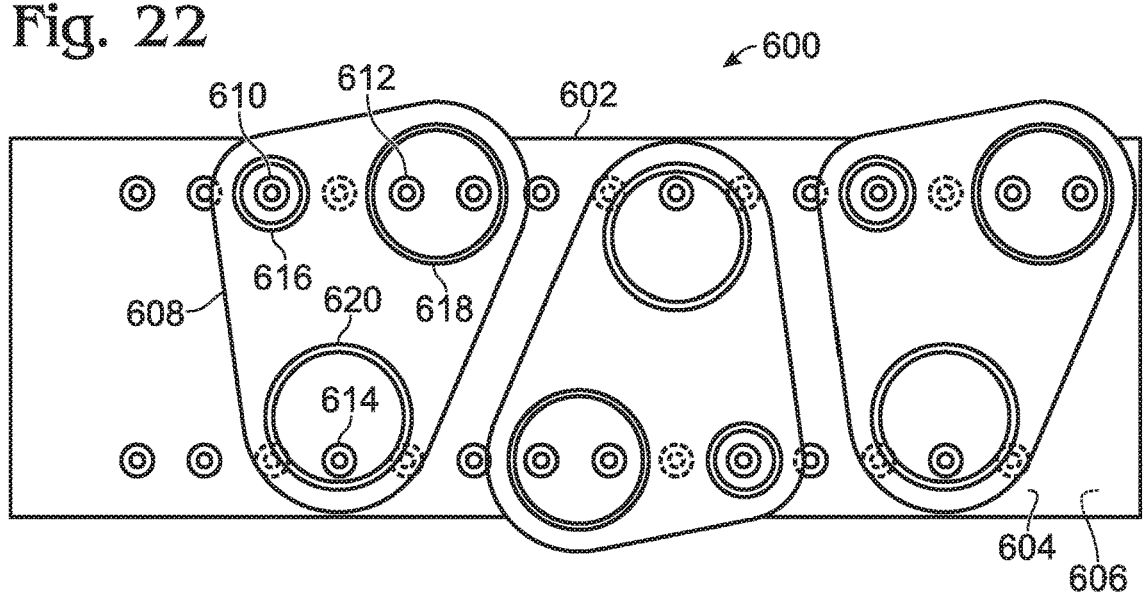
FIG. 22 is a top view of still another exemplary droplet generation system, in accordance with aspects of the present disclosure.
Figure 23:
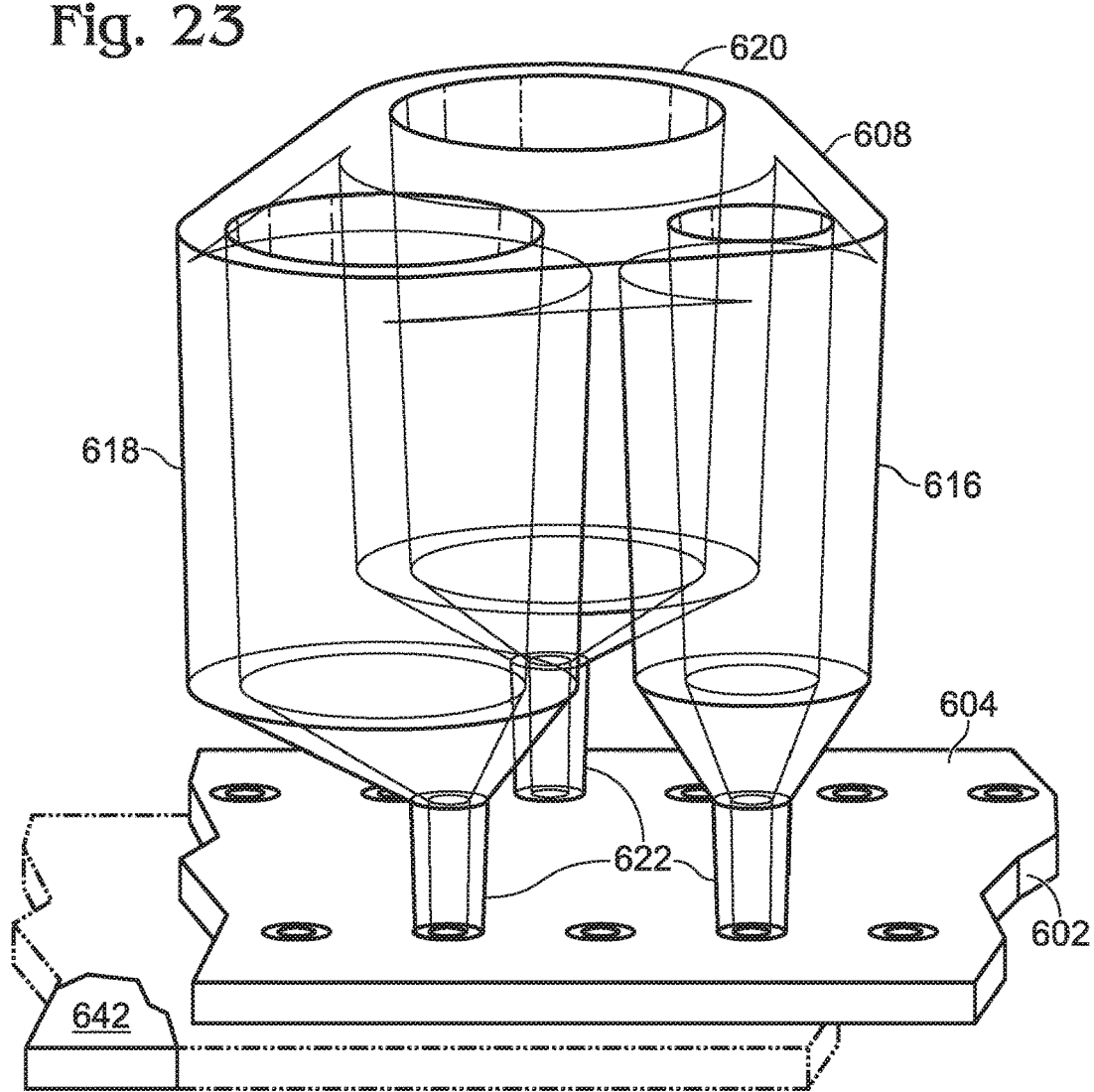
FIG. 23 is an isometric view of a magnified portion of the droplet generation system of FIG. 22.

FIGS. 22-24 depict yet another example of a planar mode droplet generator, generally indicated at 600, in which a planar substrate and a well vessel are formed as separate components. FIG. 22 is a top view of droplet generator 600, and FIG. 23 is a magnified perspective view of a portion of the droplet generator. FIG. 24 depicts the bottom surface of the droplet generator, with a planar sealing member removed for clarity. Droplet generator 600 is substantially similar to droplet generator 550 depicted in FIGS. 20-21 in some respects, and accordingly some of the similarities between droplet generator 600 and droplet generator 550 will not be described in detail below.

Droplet generator 600 includes a substantially planar substrate 602 having a top surface 604 and a bottom surface 606, and a separate well vessel 608 configured to connect to substrate 602. As in the case of droplet generator 550, well vessel 608 has only three wells, rather than four as in the case of droplet generator 500. Top surface 604 of substrate 602 includes a sample port 610, a background fluid port 612, and a droplet outlet port 614, all formed in top surface 604 of substrate 602. Each of these ports takes the form of a substantially cylindrical aperture, but as described previously, any desired shape may be used.

Well vessel 608 includes a sample well 616, a background fluid well 618, and a droplet outlet well 620, each configured to make a substantially fluid tight connection with the associated ports of the substrate. As in the case of droplet generators 500 and 550, regardless of the shapes of the ports, each well includes a complementary protrusion 622 configured to fit securely and in a fluid tight manner within the corresponding port. In addition, the connection between the ports and the wells may be made in many different ways, and may include various components configured to facilitate a fluid tight connection, as described previously with respect to droplet generators 500 and 550.

The primary difference between droplet generator 600 and droplet generator 550 is the spacing between sample well 616 and background fluid well 618. As depicted in FIGS. 22-23, in the case of droplet generator 600, these wells are not configured to fit into adjacent ports of the substrate as in the case of droplet generator 550, but rather are configured to fit into ports that are separated from each other by another, unused port. This spacing provides certain possible advantages to the droplet generator, as described below.

As depicted in the non-central portions of FIG. 24, a network of channels, generally indicated at 630, is formed in the bottom surface 606 of substrate 602. Network 630 is configured to fluidically interconnect sample port 610, background fluid port 612, and droplet outlet port 614. A droplet generation region 632 is defined by network of channels 630 and configured to generate sample-containing droplets suspended in the background fluid. More specifically, droplet generation region 632 is defined by the intersection of a sample channel 634, a pair of background fluid sub-channels 636*a*, 636*b*, and droplet channel 638. Sample channel 634 is configured to transport sample-containing fluid from sample port 610 to droplet generation region 632, background fluid sub-channels 636*a*, 636*b* are configured to transport background fluid from background fluid port 612 to droplet generation region 632, and droplet channel 638 is configured to transport sample-containing droplets from droplet generation region 632 to droplet outlet port 614.

As FIG. 24 indicates, background fluid sub-channels 636*a*, 636*b* are each fed by a background fluid channel 636 that transports background fluid from background fluid well 618. Sub-channels 636*a*, 636*b* then transport background fluid to droplet generation region 632 so that the background fluid arrives at the droplet generation region from two different directions, forming a cross-shaped (or topologically equivalent) droplet generation region. As has been described with respect to previous planar droplet generator embodiments, sub-channels 636*a*, 636*b* may be configured to have substantially the same hydraulic resistance, for example by providing the sub-channels with substantially the same lengths, so that background fluid reaches droplet generation region 632 with substantially the same flow rate in each sub-channel.

In addition, other features may be provided to channel network 630, including an air trap 640 disposed along the path of the sample-containing fluid, and regions of varying channel diameter, as indicated by the diameter of sub-channels 636*a*, 636*b* in the vicinity of droplet generation region 632. Furthermore, a planar sealing member 642 may be provided, which in some cases may include all or a portion of the channel network. These features serve purposes that have been described previously.

IV. Continuous Mode Examples

This section describes examples of "continuous mode" droplet generators, in which the droplet generator is manufactured from a single piece of material; see FIGS. 7 and 25-33. As described in more detail below with respect to several specific examples, an advantage of this single piece design is that there is no need to precisely align multiple parts to form the droplet generator geometry.

One type of continuous mode droplet generator is based on a hollow tube with one or more holes drilled through the tube walls to intersect the hollow channel. For example, FIG. 7, which has been described previously, depicts several different droplet generator geometries of this type. Specifically, droplet generators 200, 220, and 240 all may be characterized as continuous mode droplet generator tubes, because they are formed from a single piece of material. In contrast, droplet generator 260 of FIG. 7 is formed of two separate butted tubes requiring careful alignment, and thus would not be characterized as a continuous mode droplet generator.

Figure 25:
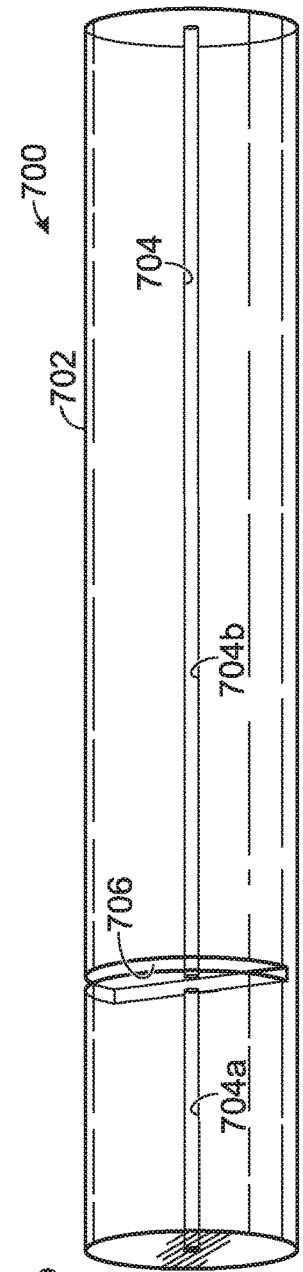
FIG. 25 is an isometric view of a droplet generator tube, in accordance with aspects of the present teachings.

FIG. 25 depicts yet another type of continuous mode droplet generator, generally indicated at 700, which is similar in some respects to droplet generators 200, 220, and 240 of FIG. 7. Droplet generator 700 includes a hollow droplet generator tube 702 having a channel 704 running along its length. A slit 706 is partially cut into the side of the tube, to intersect channel 704 and divide the channel into two aligned sections 704*a* and 704*b*. Slit 706 also forms a radial flow channel for the flow of background fluid. Accordingly, if sample-containing fluid is transported through channel section 704*a* and background fluid is transported into slit 706, sample-containing droplets may be created and suspended in the background fluid, and the resulting emulsion may be transported through channel section 704*b*.

Figure 27:
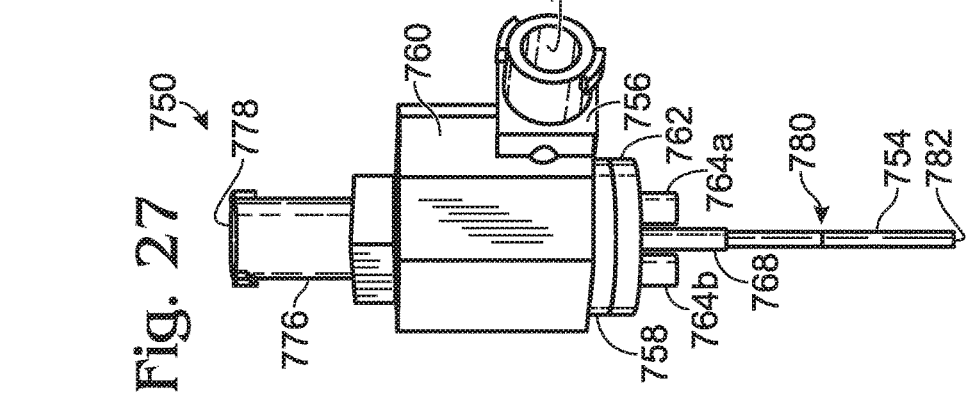
FIG. 27 is an assembled view of the droplet generation system of FIG. 26.
Figure 26:
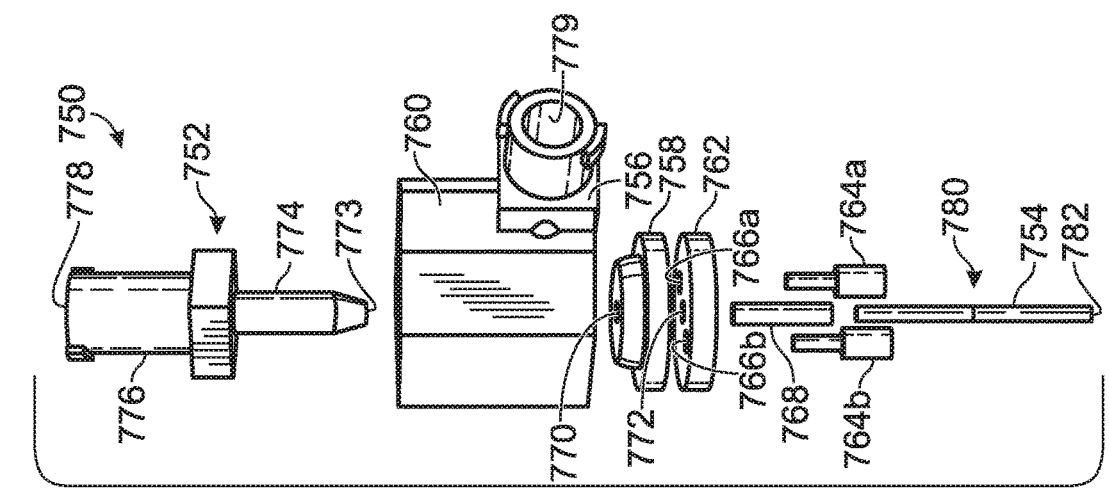
FIG. 26 is an exploded isometric view of another droplet generation system, in accordance with aspects of the present teachings.

FIGS. 26-27 depict an example of a more complete continuous mode droplet generator system, generally indicated at 750. FIG. 26 is an exploded elevational view of droplet generator system 750, and FIG. 27 is an assembled elevational view of the droplet generator system. Droplet generator system 750 includes a sample well 752, a tubular droplet generator 754, an oil feed connector 756, and a housing base 758, all configured to fit securely into a droplet generation housing 760. A compression plate 762 is used to compress housing base 758 against housing 760, to form a fluid tight surface at the bottom of the housing. Compression is caused by a pair of compression screws 764*a*, 764*b*, which fit into corresponding apertures 766*a*, 766*b* in the compression plate. Aligned apertures (not shown) in the housing base and the housing receive the compression screws and allow them to compress the housing base into the housing.

A segment of hollow, stainless steel tubing 768 fits within aligned central apertures 770, 772 of the housing base and compression plate, respectively, and extends into housing 760. Droplet generator 754 may be inserted through tubing 768, into the interior of housing 760, and into a distal aperture 773 of sample well 752. More specifically, the droplet generator is inserted into the distal aperture of sample well 752 to form a (disposable) sample handling assembly. The sample handling assembly is inserted into the (non-disposable) housing assembly. After use, the sample handling assembly may be contaminated with sample and can be discarded. A sample handling assembly may be used with each sample to reduce cross-contamination.

In this example, sample well 752 includes a Luer taper 774 configured to fit into a corresponding "female" Luer mating portion of housing 760, to form a substantially leak-free connection between the sample well and the housing. Aperture 773 is disposed at the distal end of taper 774, and is configured to securely receive droplet generator 754. Similarly, oil feed connector 756 also may include a Luer taper (not shown), configured to fit into a corresponding aperture of housing 760, which thus provides a background fluid input channel for oil or some other background fluid to enter the housing.

Sample well 752 also includes a reservoir portion 776 configured to receive sample-containing fluid to be used in forming sample-containing droplets. A proximal aperture 778 of the reservoir portion may be configured to receive standardized or proprietary fluid fittings and/or pressure fittings. This may facilitate the transfer of sample-containing fluid to the sample well, and/or the application of pressure to the sample-containing fluid to cause the formation of sample-containing droplets. Similarly, a proximal aperture 779 of the oil feed connector may be configured to accept standard or proprietary fluid fittings and/or pressure fittings, to facilitate the transfer of pressurized oil or some other background fluid into housing 760.

Droplet generator 754 may be similar to any of the previously described droplet generator tubes, such as tubes 200, 220, 240, or 700. More specifically, in this example droplet generator 754 is a continuous hollow tube having a slit 780 formed at an intermediate location along the length of the tube. Slit 780 is oriented substantially normally relative to the length of the droplet generator tube, and extends far enough into the droplet generator tube to intersect the central channel of the tube. More generally, slits and/or channels that penetrate from the outer periphery of the droplet generator to intersect its central channel may be oriented at any desired angle(s). Furthermore, these slits and/or channels need not pass linearly from the periphery of the droplet generator tube toward its central channel, but may be configured to have any desired trajectories. This may, for example, allow the hydraulic resistance of the background fluid channel to be tuned to a desired value, as a manner of controlling the rate of production of sample-containing droplets.

When droplet generator 754 is inserted into tubing 768 and passes through the interior of housing 760 and into distal aperture 773 of sample well 752, slit 780 will be exposed to any fluid present in the interior portion of housing 760. When sample-containing fluid is transported from sample well 752 into droplet generator tube 754, the sample-containing fluid eventually reaches slit 780, where it encounters pressurized background fluid that has been transported into housing 760 via the background fluid input channel of the housing. Sample-containing droplets suspended in the background fluid are created in the vicinity of the slit, and transported further down the droplet generator, where they eventually reach a droplet outlet region 782 defined by the distal end of the droplet generator tube.

Figure 28:
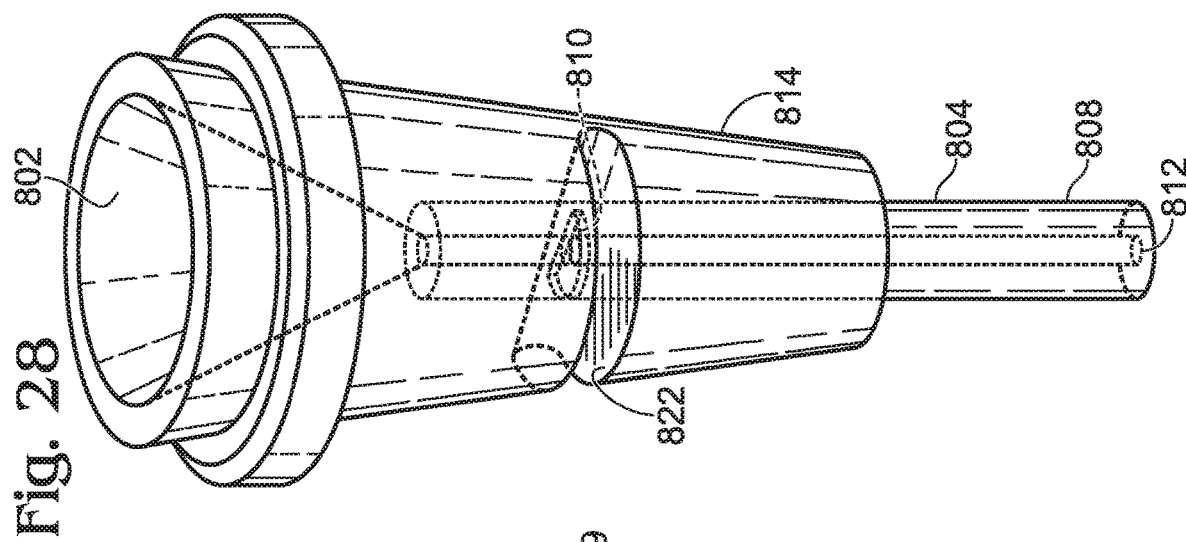
FIG. 28 is a partially transparent isometric view of a portion of still another droplet generation system, in accordance with aspects of the present teachings.

FIGS. 28-29 depict another example of a continuous mode droplet generation system, generally indicated at 800. Droplet generation system 800 includes a sample well 802, a droplet generator 804 configured to receive sample-containing fluid from the sample well, and an outer housing 806 configured to selectively receive the droplet generator. In some cases, the sample well and the droplet generator, which come into direct contact with sample-containing material, may be configured as a disposable component, whereas the housing, which does not come into direct contact with sample-containing material, may be configured as a reusable component. The droplet generator may be integrally formed with the sample well, or it may be formed separately and selectively integrated with the sample well.

In system 800, droplet generator 804 takes the form of a droplet generation tube, of a type described previously. More specifically, droplet generator 804 is a continuous hollow tube 808 having a slit 810 formed at an intermediate location along the length of the tube. One end of the droplet generator is in fluidic communication with sample well 802. This may occur during formation of the sample well and droplet generator, if they are integrally formed, or if the droplet generator and sample well are formed separately, the droplet generator may be selectively placed in fluid communication with the sample well, by positioning it securely against a lower outlet aperture of the well. The other end of the droplet generator defines a droplet outlet region 812 configured to receive sample-containing droplets generated within a droplet generation region of the droplet generator. The droplet generator and the sample well are disposed within a substantially frustoconical inner housing 814, which is configured to fit securely within a corresponding aperture 816 in outer housing 806.

Frustoconical inner housing 814 is sized so that sample well 802 will be disposed at or above the upper surface 818 of housing 806, while droplet outlet region 812 will be disposed at or below the lower surface 820 of housing 806. Inner housing 814 includes a slit 822, which exposes slit 810 of droplet generator tube 808 to any fluid that penetrates slit 822. When inner housing 814 is properly disposed within housing 806, slits 822 and 810 will be aligned with a pair of background fluid input channels 824*a*, 824*b* which are formed within housing 806 and configured to provide background fluid to the droplet generator from a background fluid source. A pair of elastic o-rings 826, or other suitable components, may be used to secure inner housing 814 within outer housing 806 in a leak-proof manner and at the proper location. When sample-containing fluid is transported from sample well 802 into droplet generator 804, it eventually reaches the region of intersection of slit 810 and background fluid input channels 824a, 824b, at which point sample-containing droplets suspended in the background fluid are generated and directed toward droplet outlet region 812, where they may be collected and/or transported for subsequent assay steps.

Figure 31:
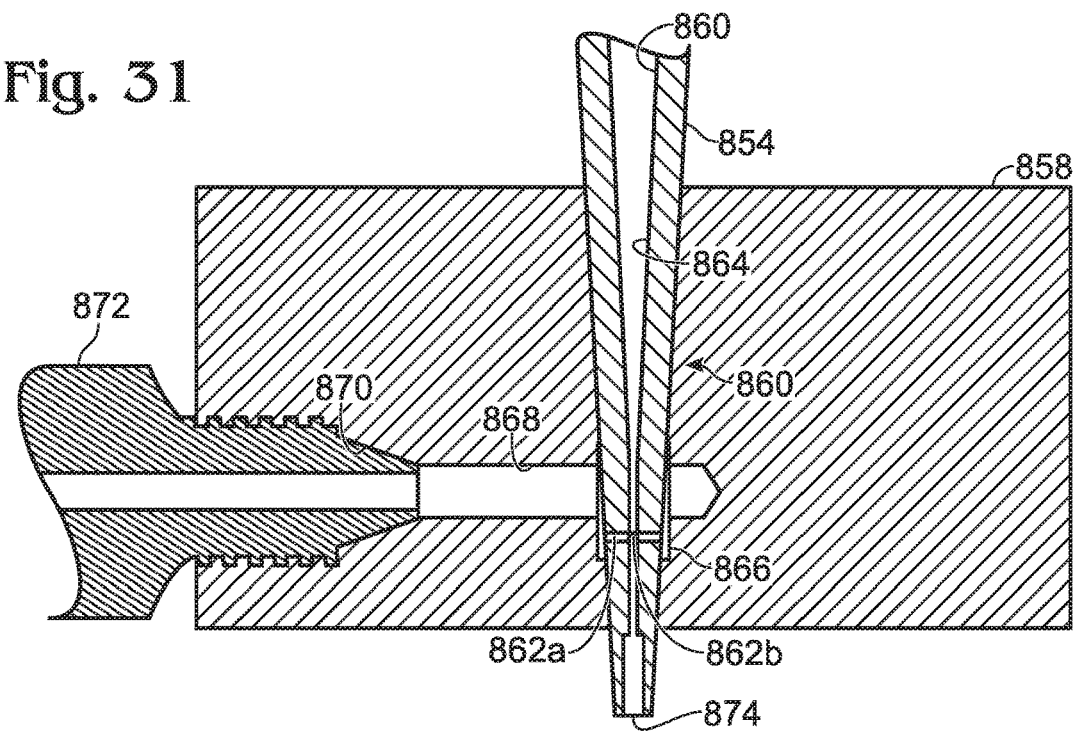
FIG. 31 is a magnified sectional view of a portion of the droplet generation system of FIG. 30.

FIGS. 30-31 depict still another example of a continuous type droplet generation system, generally indicated at 850. FIG. 30 is a schematic elevational view of system 850, and FIG. 31 is a magnified sectional view of a portion of the system. Droplet generation system 850 includes a sample well 852 and an integrated droplet generator 854, which collectively take the form of a modified pipette as generally indicated at 856. Droplet generation system 850 also includes a housing 858 configured to selectively receive pipette 856.

Pipette 856 includes a central channel 860, which transports sample-containing fluid from the sample well portion 852 of the pipette, downward in FIGS. 30-31. Droplet generator 854 is provided in pipette 856 by forming a pair of horizontal channels 862a, 862b in the pipette tip, which intersect central channel 860. Thus, droplet generator 854 is similar to previously described examples in which a droplet generator is formed from a hollow tube that includes channels extending from the periphery of the pipette to its central channel. In other cases, the droplet generator of the current example can be formed using a slit that extends from the periphery of the pipette to its central channel, as has been described previously.

To receive the pipette, housing 858 includes a cavity, generally indicated at 860, which consists of a first, tapered bore section 864 and a second, cylindrical bore section 866. Pipette 856 fits securely within the tapered bore section, leaving a small amount of open space around a portion of the pipette disposed within the cylindrical bore section, in the vicinity of channels 862a, 862b. Housing 858 also includes a horizontal bore 868, which intersects cylindrical bore section 866 and extends beyond it. Adjacent to horizontal bore 868 (on the left-hand side of FIG. 31) is an internally threaded aperture 870, which is configured to receive a background fluid input device 872.

The background fluid input device can be used to provide pressurized background fluid to horizontal bore 868. Background fluid provided by the fluid input device will fill horizontal bore 868 and cylindrical bore section 866, and enter horizontal channels 862a, 862b of the droplet generator, where it will intersect sample-containing fluid passing downward through channel 860. According to previously described principles, an emulsion of sample-containing droplets suspended in the background fluid will therefore be produced, and will travel further down channel 860 until they reach a droplet outlet region 874 defined by a distal aperture of pipette 856.

Figure 32:
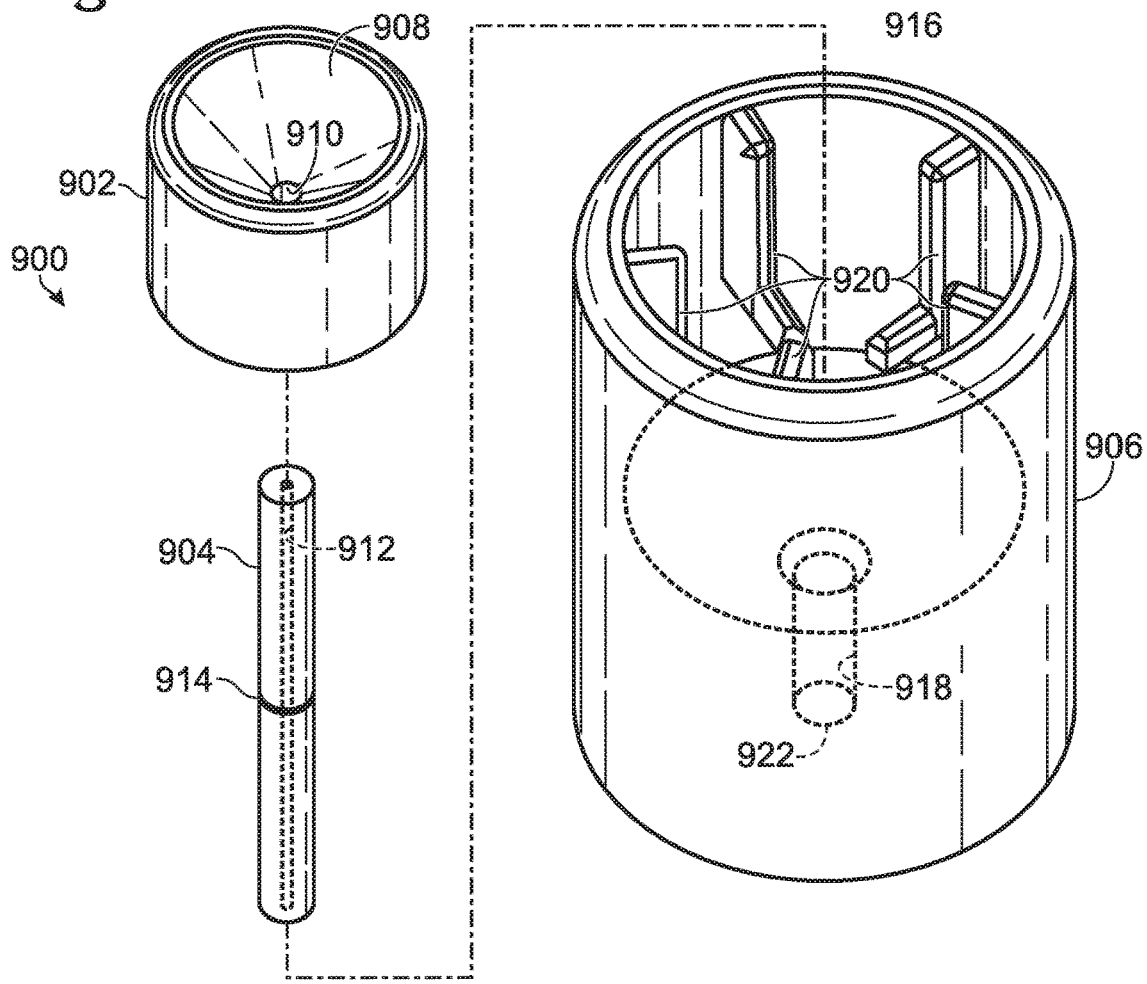
FIG. 32 is an exploded isometric view of another droplet generation system, in accordance with aspects of the present teachings.

FIG. 32 depicts an exploded view of yet another example of a continuous type droplet generation system, generally indicated at 900. Droplet generator 900 includes a sample well 902, a droplet generator 904, and a housing 906. Sample well 902 includes a conical interior portion 908 configured to hold sample-containing fluid. An aperture 910 allows fluid to pass from the sample well into droplet generator 904, as described in more detail below. Droplet generator 904 is a tubular droplet generator of a type described previously, including a central fluid channel 912 and a transverse slit 914 that intersects the central channel. Droplet generator 904 is configured to fit securely within a complementary aperture (not shown) formed in the bottom surface of sample well 902, so that the droplet generator will be fluidically connected with the sample well, with a portion of the droplet generator (including slit 914) extending below the sample well.

Housing 906 includes a central aperture 916 configured to receive sample well 902, and a cylindrical bore 918 extending below the central aperture and configured to receive a lower portion of droplet generator 904. A plurality of alignment features 920 are provided in the interior of central aperture 916 and configured to align sample well 902 and droplet generator 904 in desired positions within housing 906. More specifically, when sample well 902 and droplet generator 904 are aligned correctly within housing 906, slit 914 of the droplet generator will be disposed below alignment features 920 and above cylindrical bore 918. At the same time, the upper portion of sample well 902 will be approximately aligned with the upper portion of housing 906, although in some cases the upper portions of well 902 and housing 906 may be offset by a desired predetermined amount.

Housing 906 is configured to receive a background fluid such as oil, and thus to function as a background fluid well. Specifically, background fluid may be disposed at least in the portion of central aperture 916 below alignment features 920 and above cylindrical bore 918. Accordingly, when system 900 is assembled so that sample well 902 and droplet generator 904 are aligned correctly within housing 906, slit 914 of droplet generator 904 will be submerged in background fluid. A pressure source (not shown) then may be connected to the upper surface of housing 906, and in some cases also to the upper surface of sample well 904, to apply pressure to both the sample-containing fluid in the sample well and the background fluid in the housing.

Upon application of pressure from a pressure source, the sample-containing fluid and the background fluid will intersect at a droplet generation region defined by the intersection of central channel 912 and slit 914, and sample-containing droplets suspended in the background fluid will be generated. This emulsion of droplets will then be transported through the lower portion of droplet generator 904, toward a droplet outlet region 922 defined by the distal outlet of the droplet generator. From there, the sample-containing droplets may be collected and/or transported for a subsequent assay step such as thermocycling.

Figure 33:
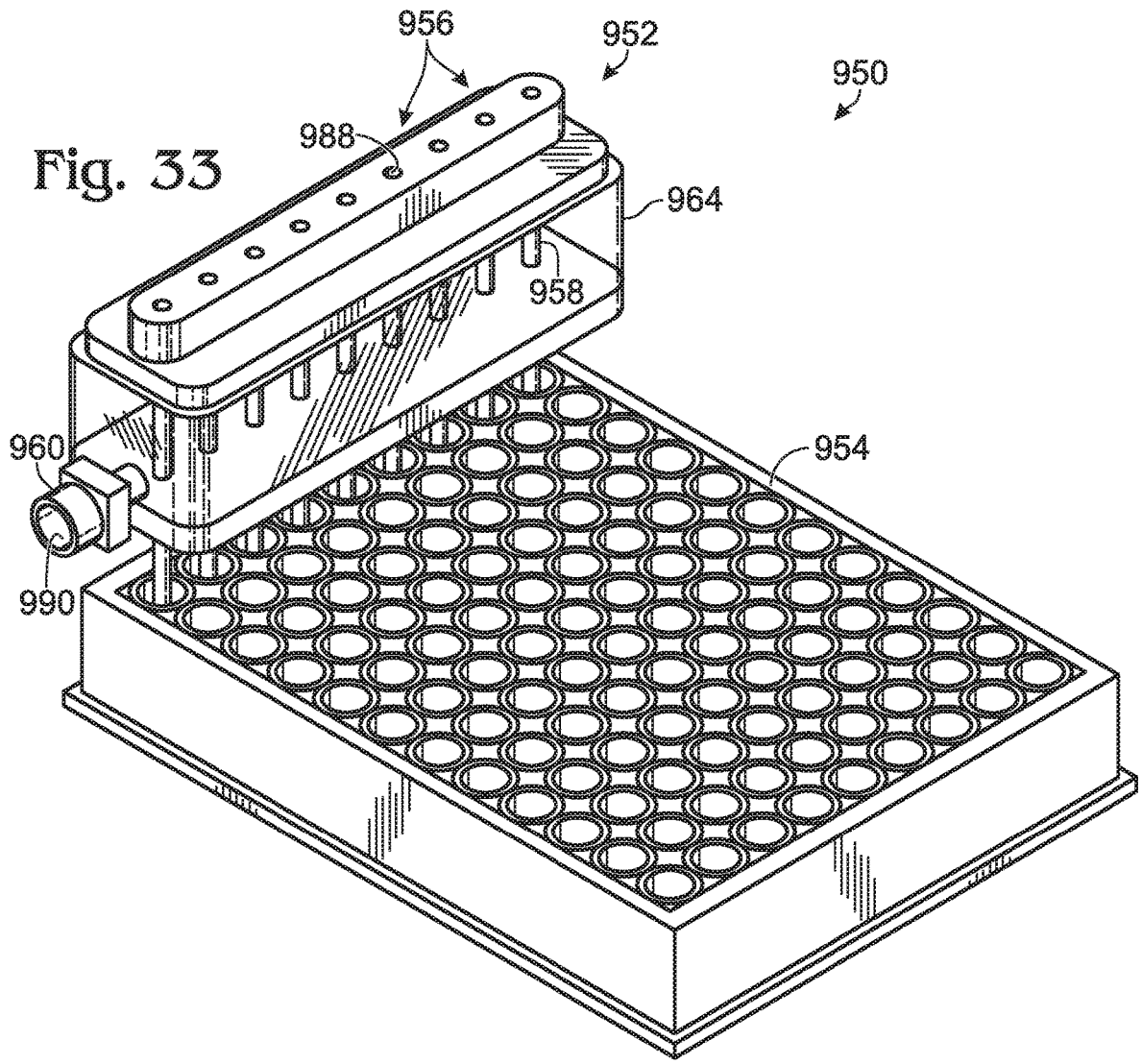
FIG. 33 is an exploded isometric view of yet another droplet generation system, in accordance with aspects of the present teachings.
Figure 34:
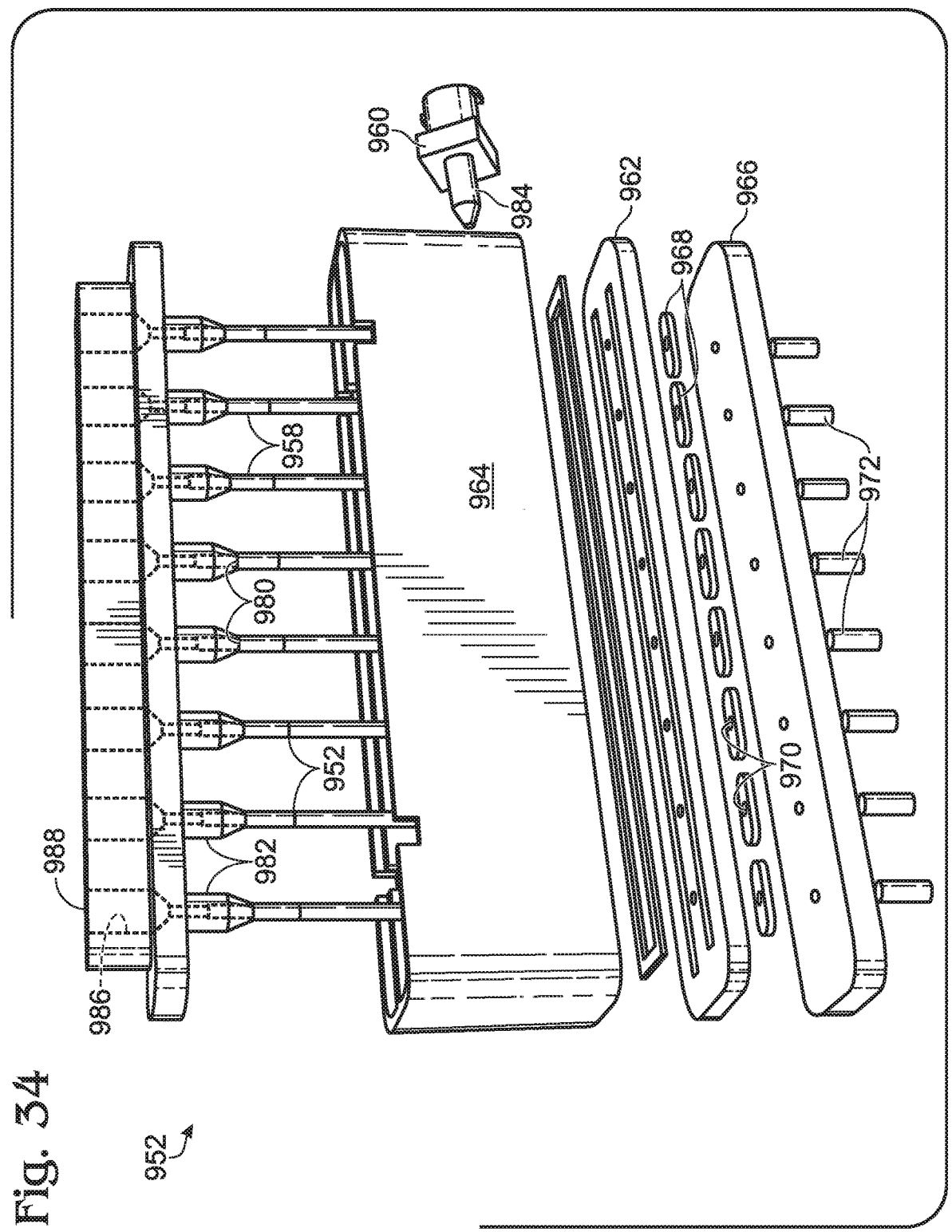
FIG. 34 is an exploded isometric view of a portion of the droplet generation system of FIG. 33.

FIGS. 33-34 depict an exemplary multi-sample continuous mode droplet system, generally indicated at 950. FIG. 33 shows system 950 in an assembled state, and FIG. 34 is an exploded view of a portion of system 950. Droplet generator system 950 includes a droplet generator assembly 952, and a droplet well plate 954 configured to receive sample-containing droplets that have been generated by the droplet generator assembly.

Droplet generator assembly 952 is similar in some respects to droplet generator system 750 depicted in FIGS. 26-27. Specifically, droplet generator assembly 952 includes a plurality of sample wells, generally indicated at 956, each with an associated tubular droplet generator 958, an oil feed connector 960, and a housing base 962, all configured to fit securely within a housing 964. A compression plate 966 is used to compress housing base 962 against housing 964, to form a fluid tight surface at the bottom of the housing. The compression plate may, for example, utilize compression screws (not shown) to compress the housing base against the housing, or it may be preloaded and then adhered to the housing in any suitable manner. Gasket seals 968 having central apertures 970 are disposed between housing base 962 and compression plate 966, to further prevent leakage from the housing.

Segments of hollow, stainless steel tubing 972 fit within aligned central apertures 970, 974, 976 of the gasket seals, the housing base and the compression plate, respectively, and tubing segments 972 extend partially into housing 964. When system 950 is assembled, droplet generators 978 extend through tubing segments 972, into the interior of housing 964, and into distal apertures 980 of sample wells 956. Sample wells 956 may include Luer tapers 982 configured to fit into a corresponding "female" Luer mating portion of housing 964, to form a substantially leak-free connection between the sample well and the housing. Apertures 980 are disposed at the distal ends of tapers 982, and are configured to securely receive droplet generators 978. Similarly, oil feed connector 960 also may include a Luer taper 984, configured to fit into a corresponding aperture of housing 964, and thereby to provide a background fluid input channel for oil or some other background fluid to enter the housing.

Sample wells 956 also include reservoir portions, generally indicated at 986, configured to receive sample-containing fluid to be used in forming sample-containing droplets. A proximal aperture 988 of each reservoir portion may be configured to receive standardized or proprietary fluid fittings and/or pressure fittings. This may facilitate the transfer of sample-containing fluid to the sample well, and/or the application of pressure to the sample-containing fluid to cause the formation of sample-containing droplets. Similarly, a proximal aperture 990 of the oil feed connector may be configured to accept standard or proprietary fluid fittings and/or pressure fittings, to facilitate the transfer of pressurized oil or some other background fluid into housing 964.

Droplet generators 978 may be similar to any of the previously described droplet generator tubes, such as tubes 200, 220, 240, or 700. More specifically, in this example, droplet generators 978 each take the form of a continuous hollow tube having a slit 992 formed at an intermediate location along the length of the tube. Slits 992 extend far enough into the associated droplet generator tube to intersect the central channel of the tube. When droplet generators 978 are inserted into tubing segments 972 and pass through the interior of housing 964 and into distal apertures 980 of sample wells 956, each slit 992 will be exposed to background fluid present in the interior portion of housing 964.

Thus, when sample-containing fluid is transported from each sample well 956 into droplet generator tubes 978, the sample-containing fluid eventually reaches a slit 992, where it encounters pressurized background fluid that has been transported into housing 964 via the background fluid input channel of the housing. Sample-containing droplets suspended in the background fluid are created in the vicinity of the slit, and transported further down the droplet generator, where they eventually reach one of droplet outlet regions defined by the distal end of the associated droplet generator tube.

V. Two-Part Mode Examples

This section provides examples of two-part mode droplet generation systems, in which a first portion of the system contains a sample channel for transporting sample-containing fluid to a droplet generation region, and a second portion of the system contains a droplet channel for transporting sample-containing droplets away from the droplet generation region; see FIGS. 35-42. A background fluid channel for transporting background fluid to the droplet generation region may be included with either the first or second portions of the system, or may be included in a separate portion. In some cases, the first portion of the system, which comes into direct contact with the sample-containing fluid, may be configured as a disposable component, and the second portion of the system, which does not come into direct contact with the sample-containing fluid, may be configured as a reusable component. Furthermore, the term "two-part" is not meant to be limiting; in some cases, systems according to this mode may use three or more separate components.

FIGS. 35-38 depict a first example of a two-part droplet generation system, generally indicated at 1000, in accordance with aspects of the present teachings. As depicted in FIG. 35, system 1000 includes a substantially planar droplet generator substrate 1002, and a sample container, which in this example takes the form of a pipette tip 1004. Substrate 1002 includes a droplet generation well 1006, and an emulsion well 1008. A droplet channel 1010 formed in the substrate fluidically interconnects the droplet generation well and the emulsion well. Further details of substrate 1002 and pipette tip 1004 are shown in FIGS. 36-38.

FIG. 36 is a magnified sectional view of an end portion of pipette tip 1004. As FIG. 36 depicts, pipette tip 1004 includes a sample well portion 1012, and a sample channel 1014 through which sample-containing fluid may be transported from sample well portion 1012 to droplet generation well 1006 of substrate 1002.

FIG. 37 is a magnified sectional view of droplet generation well 1006, and FIG. 38 is a top view of droplet generation well 1006. As shown in FIG. 38, the droplet generation well includes an upper well portion 1016, and a plus-shaped lower well portion 1018. An emulsion outlet channel 1020, formed in substrate 1002, fluidically interconnects lower well portion 1018 with droplet channel 1010. To seal channels 1010 and 1020, and thus to provide a leak-free fluid channel between droplet generation well 1006 and emulsion well 1008, a sealing member 1026 may be disposed along the bottom surface of substrate 1002. Sealing member 1026 may, for example, take the form of a flexible film that may be adhered to the bottom of the substrate, or it may be a relatively inflexible member that is constructed from a material similar to the material of the substrate itself, such as a thermoplastic material. In the latter case, all or a portion of channel 1010 may be formed in sealing member 1026 rather than in substrate 1002.

To generate an emulsion of sample-containing droplets suspended in background fluid such as oil, sample-containing fluid is loaded into sample well portion 1012 of pipette tip 1004, and background fluid is loaded into droplet generation well 1006. A distal end portion 1022 of pipette tip 1004 is then placed into the droplet generation well, partially within plus-shaped lower well portion 1018. The outer diameter of distal end portion 1022 is small enough to fit within the upper opening of plus-shaped lower well portion 1018, but too large to fit within the lower outlet of the plus-shaped well portion, due to the presence of step-like features 1019. Thus, when inserted fully into droplet generation well 1006, the pipette tip rests on top of step-like features 1019, but oil can pass around the outer periphery of end portion 1022 to reach outlet 1024 of sample channel 1014 of the pipette tip. Furthermore, step-like features 1019 can be given any desired thickness, to space distal end portion 1022 of the pipette tip any desired distance from emulsion outlet channel 1020.

Accordingly, pipette tip 1004 and emulsion outlet channel 1020 form a butted tube type droplet generator, with the gap between pipette tip 1004 and channel 1020 set by the depth of plus-shaped lower well portion 1018. See, e.g., droplet generator 280 of FIG. 7 and the accompanying discussion above. To form an emulsion, negative pressure is applied to emulsion well 1008, drawing sample-containing fluid out of pipette tip 1004 and also drawing background fluid out of droplet generation well 1006. Sample-containing droplets are formed as the sample-containing fluid and the background fluid each pass through plus-shaped lower well portion 1018. The resulting emulsion then passes through emulsion outlet channel 1020 and droplet channel 1010, to reach emulsion well 1008.

Figure 40:
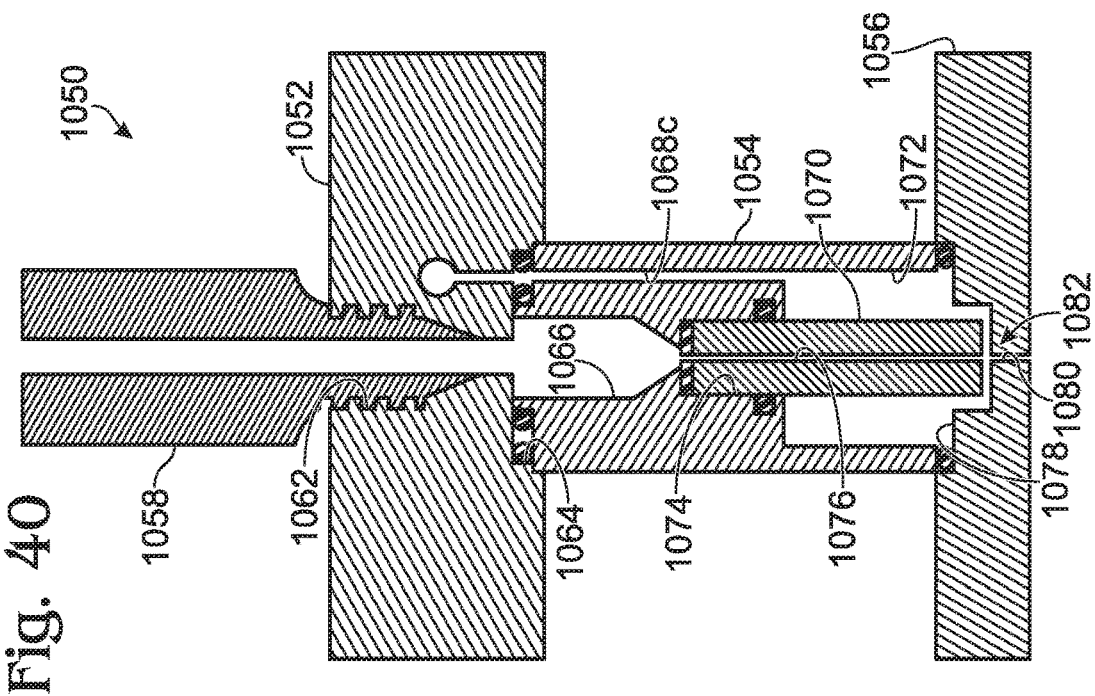
FIG. 40 is a sectional view of the droplet generation system of FIG. 39.
Figure 39:
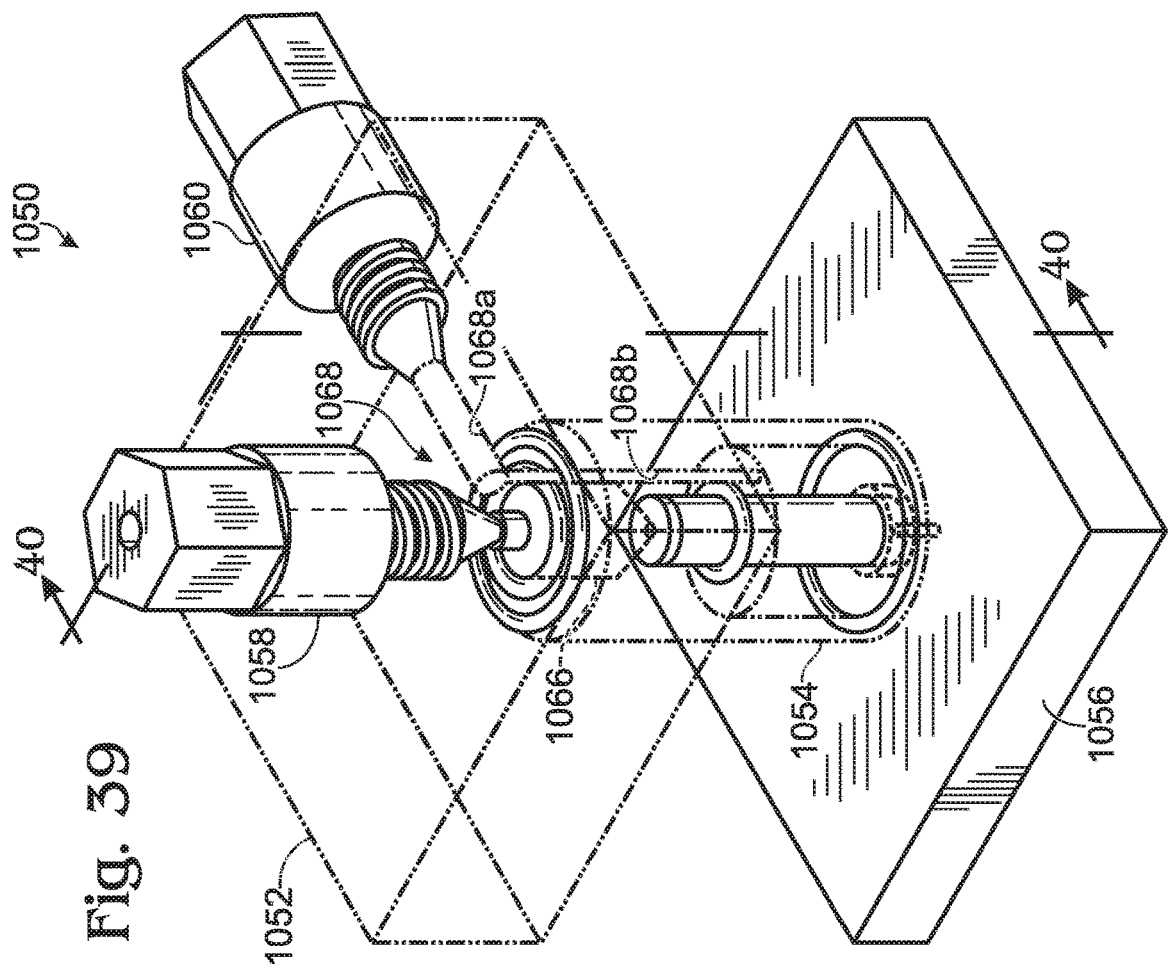
FIG. 39 is a partially transparent isometric view of still another droplet generation system, in accordance with aspects of the present teachings.

FIGS. 39-40 depict another example of a two-part droplet generation system, generally indicated at 1050, in accordance with aspects of the present teachings. FIG. 39 is an isometric view of system 1050, and FIG. 40 is a sectional view taken along the line 40-40 in FIG. 39. System 1050 includes an input housing 1052, a droplet generator housing 1054, which also may be referred to as a sample cartridge, and an output housing 1056. Input housing 1052 includes structures such as threaded apertures for receiving a sample pressure source 1058 and a background fluid source 1060; a threaded aperture 1062 for receiving pressure source 1058 can be seen in FIG. 40. A lower aperture 1064 is formed at the bottom surface of input housing 1052, and configured to receive an upper portion of droplet generator housing 1054. Sample reservoir 1066 is configured to be in fluid communication with the distal end portion of sample pressure source 1058.

Input housing 1052 also includes a background fluid channel, generally indicated at 1068, which is configured to transport background fluid from background fluid source 1060, through the input housing, and into droplet generator housing 1054. Specifically, background fluid channel 1068 includes a first sub-channel 1068a configured to transport background fluid from background fluid source 1060 within input housing 1052, to a second sub-channel 1068b configured to transport background fluid from input housing 1052 into sub-channel 1068c of droplet generator housing 1054.

Droplet generator housing 1054 includes a background fluid channel 1068c that serves as a continuation of channel 1068b when input housing 1052 is aligned correctly with droplet generator housing 1054. Droplet generator housing 1054 also includes a hollow cylinder 1070, and a lower aperture 1072. In some cases, cylinder 1070 may be integrally formed with droplet generator housing 1054. In other cases, as depicted in FIG. 40, the droplet generator may include a cylindrical bore 1074 configured to receive cylinder 1070. In either case, an axial sample-containing fluid channel 1076 of cylinder 1070 will be placed into contact with the distal end portion of sample reservoir 1066 when system 1050 is assembled.

Output housing 1056 includes a stepped cylindrical aperture 1078. Aperture 1078 is configured to receive a lower, outer portion of droplet generator housing 1054, in such a manner that a fluid tight seal is formed between the droplet generator and the output housing. Furthermore, when system 1050 is assembled, sample-containing fluid channel 1076 of cylinder 1070 will be in substantial alignment with a droplet outlet channel 1080 formed in output housing 1056. Accordingly, cylinder 1070 and output housing 1056 form a butted tube style droplet generator, as has been described previously.

An emulsion of sample-containing droplets suspended in a background fluid such as oil is generated with system 1050 as follows. Sample is placed in sample reservoir 1066. The system 1050 is assembled. Oil or some other background fluid is supplied via background fluid source 1060, which partially fills a lumen space between lower aperture 1072 and cylinder 1070. A pressure is supplied via pressure source 1058, causing sample to flow to droplet generation region 1082. Droplets are collected via droplet outlet channel 1080. The sample contacting portions of system 1050, including hollow cylinder 1070 and housing 1054, are configured to be disposable after creating an emulsion.

Figure 41:
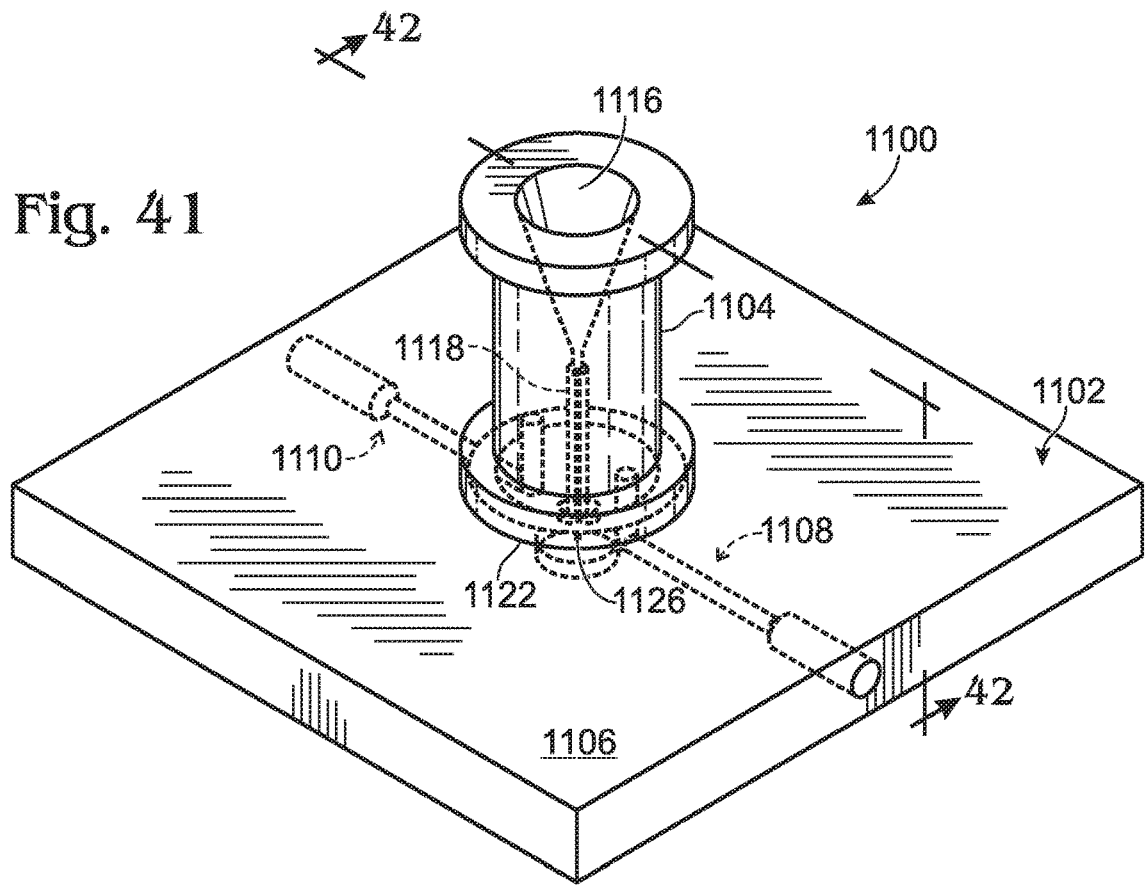
FIG. 41 is a partially transparent isometric view of yet another droplet generation system, in accordance with aspects of the present teachings.
Figure 42:
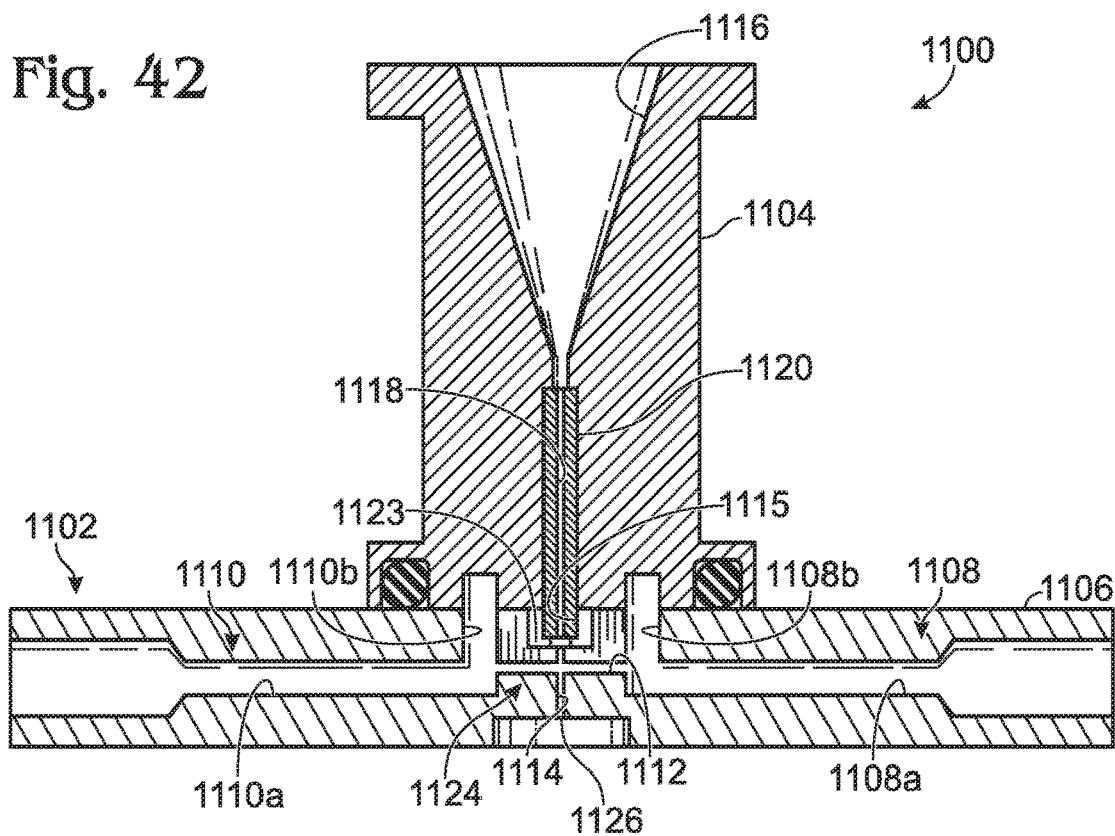
FIG. 42 is a sectional view of the droplet generation system of FIG. 41.

FIGS. 41-42 depict still another example of a two-part mode droplet generation system, generally indicated at 1100. Droplet generation system 1100 includes a droplet generator plate, generally indicated at 1102, and a removable sample module 1104. In some cases, the droplet generator plate will be configured as a reusable component, whereas the sample module will be configured as a disposable component.

Droplet generator plate 1102 includes a substantially planar substrate 1106 having a pair of background fluid channels 1108, 1110 extending from opposite sides of the substrate toward the center of the substrate. More specifically, each background fluid channel includes a respective pair of sub-channels 1108a, 1108b and 1110a, 1110b, where one of the sub-channels on each side is parallel to the planar top and bottom surfaces of substrate 1106, and the other sub-channel on each side is normal to the planar surfaces of the substrate. Each of the vertical sub-channels 1108b, 1110b is in fluid communication with a horizontal background fluid channel 1112 formed in substrate 1106, which spans the geometric center of the substrate and intersects a vertical droplet outlet channel 1114 that is also formed in the substrate. Droplet generator plate 1102 further defines a central cylindrical bore 1115, configured to receive a cylindrical sample tube as described below.

Sample module 1104 includes a sample well portion 1116 formed in an upper portion of the sample module, which provides sample-containing fluid to a vertical sample fluid channel 1118. Sample fluid channel 1118 may be formed in a cylindrical tube 1120 inserted into or integrally formed with the sample module, and which extends a predetermined distance below a bottom surface 1122 of sample module 1104. This distance is determined by the thickness of a plus-shaped spacing feature 1123 of the sample module. Tube 1120 is unable to fit through the aperture defined by plus-shaped feature 1123, and thus stops when it contacts the plus-shaped feature. As a result, sample tube 1120 extends into central cylindrical bore 1115 so that a slight gap is left between the bottom of tube 1120 and the top of droplet outlet channel 1114, to form a butted tube type droplet generator defined by a droplet generation region, generally indicated at 1124, where background fluid transported by channel 1112 intersects with sample fluid transported by channel 1118.

To form an emulsion of sample-containing droplets with system 1100, sample-containing fluid is placed in sample well 1116, and sample module 1104 is assembled with droplet generator plate 1102. Background fluid is transported into droplet generator plate 1102 from each side, and pressure is applied to the system either in the form of positive pressure to the sample well and the background fluid channels, or negative pressure to the droplet outlet channel. In either case, sample-containing fluid is transported to droplet generation region 1124 through sample fluid channel 1118, and background fluid is transported to droplet generation region 1124 through background fluid channel 1112. Sample-containing droplets suspended in the background fluid are then formed in the droplet generation region, from which they are transported through droplet outlet channel 1114 to a droplet outlet 1126.

VI. Single Hole Mode Examples

This section describes examples of single hole mode droplet generation systems, which are characterized by the fact that a sample fluid channel and a droplet outlet channel are formed by creating a single channel aperture through successive layers of material. This automatically results in substantially perfect alignment of the sample fluid channel and the droplet outlet channel.

Figure 43:
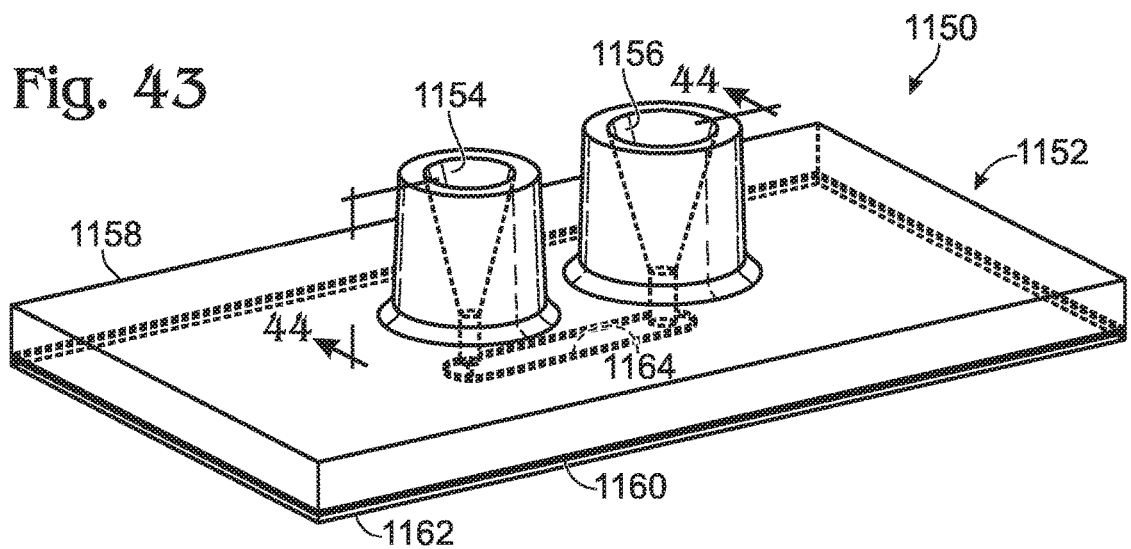
FIG. 43 is a partially transparent isometric view of another droplet generation system, in accordance with aspects of the present teachings.
Figure 44:
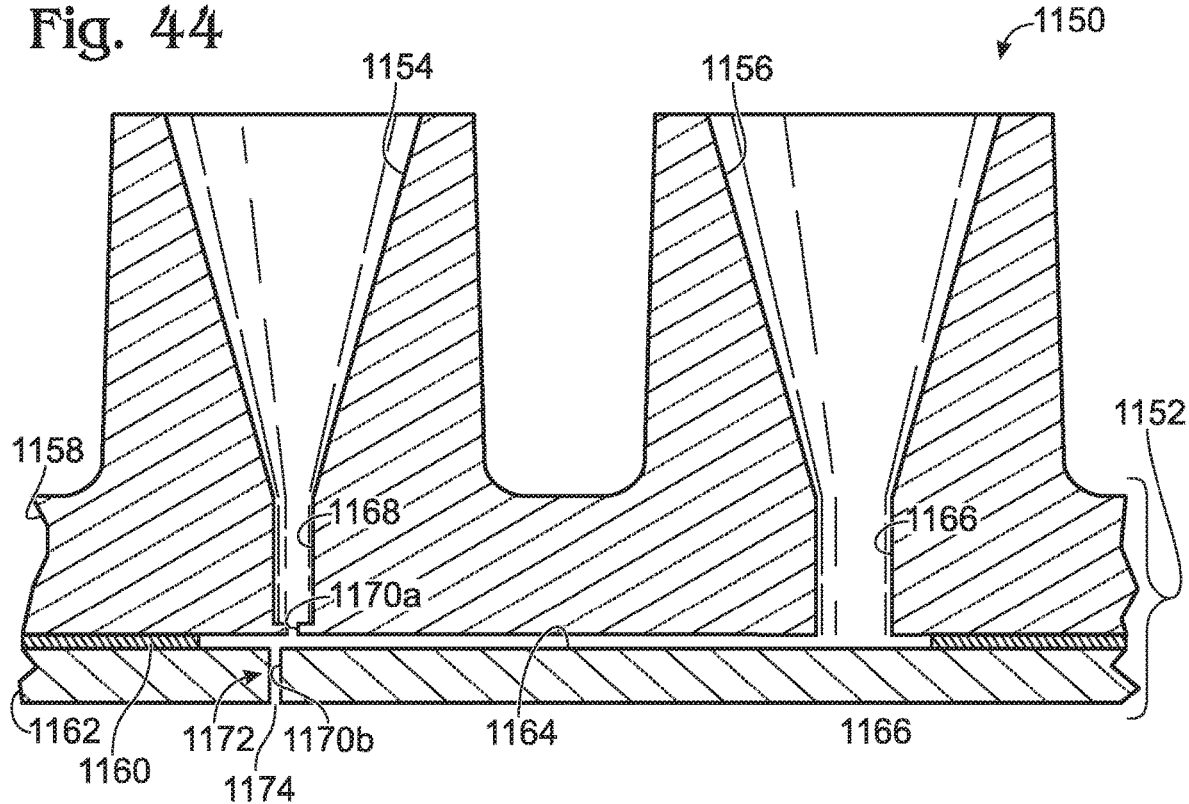
FIG. 44 is a magnified sectional view of a portion of the droplet generation system of FIG. 43.

FIGS. 43-44 depict a first example of a single hole mode droplet generation system, generally indicated at 1150. Droplet generation system 1150 includes a substrate or droplet generator plate 1152, upon which are disposed a sample well 1154 and a background fluid well 1156. The terms "substrate" and "droplet generator plate" may be used interchangeably in the present teachings. The sample well and the background fluid well may be integrally formed with the substrate, for example by injection molding, or in some cases they may be formed separately and then attached to the substrate. Furthermore, substrate 1152 may be substantially planar, as depicted in FIGS. 33-34, or it may have any other desired shape, such as a slightly curved cylindrical or spherical shape. Similarly, all of the other substrates described herein as "substantially planar" may take other alternative forms according to the present teachings.

As best seen in FIG. 44, substrate 1152 includes three layers of stacked material 1158, 1160, 1162. These material layers may be bonded together by any suitable method, such as solvent bonding, gluing, or heat sealing, among others. Middle layer 1160 includes a central aperture 1164, which in this example has an oval shape, but which in general can be given any desired two-dimensional shape, or which may take the form of a substantially linear or non-linear channel. The key feature of central aperture 1164 is that it extends between a region underneath sample well 1154 and a region underneath background fluid well 1156.

Background fluid well 1156 is configured to have an aperture 1166 extending completely through upper material layer 1158, so that background fluid well 1156 will automatically be fluidically connected to central aperture 1164 when material layers 1158, 1160, and 1162 are stacked together. Sample well 1154 is configured to have an aperture 1168 extending partially, but not completely, through upper material layer 1158. A channel 1170 is formed below aperture 1168, to fluidically interconnect sample well 1154 and central aperture 1164. Channel 1170 may be formed in a single operation, such as a drilling operation, after material layers 1158, 1160, and 1162 are assembled together. Thus, channel 1170 defines a sample channel 1170a and a droplet channel 1170b, which will necessarily be in substantially perfect alignment with each other. Alternatively, channel 1170a may be formed in a separate operation and then aligned to droplet channel 1170b during assembly.

Central aperture 1164 defines a background fluid channel that intersects with sample channel 1170a and droplet channel 1170b, to define a droplet generation region generally indicated at 1172. To create an emulsion of sample-containing droplets with system 1150, sample-containing fluid is placed in sample well 1154, and background fluid is placed in background fluid well 1156. Positive pressure is applied to the upper portions of the sample well and the background fluid well, and/or negative pressure is applied to a droplet outlet region 1174 of the system. Background fluid is then transported through the background fluid channel defined by central aperture 1164, and sample-containing fluid is transported through sample channel 1170a. These fluids intersect at droplet generation region 1172, to form sample-containing droplets suspended in the background fluid according to previously described principles. The resulting emulsion is transported through droplet channel 1170b to droplet outlet region 1174, where it may be collected and/or further transported as desired.

Figure 45:
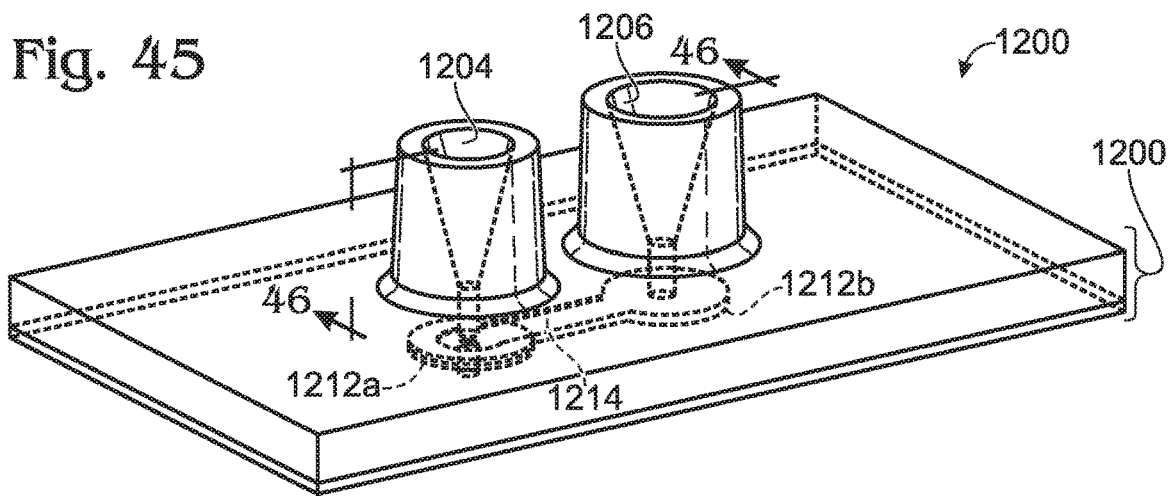
FIG. 45 is a partially transparent isometric view of still another droplet generation system, in accordance with aspects of the present teachings.
Figure 46:
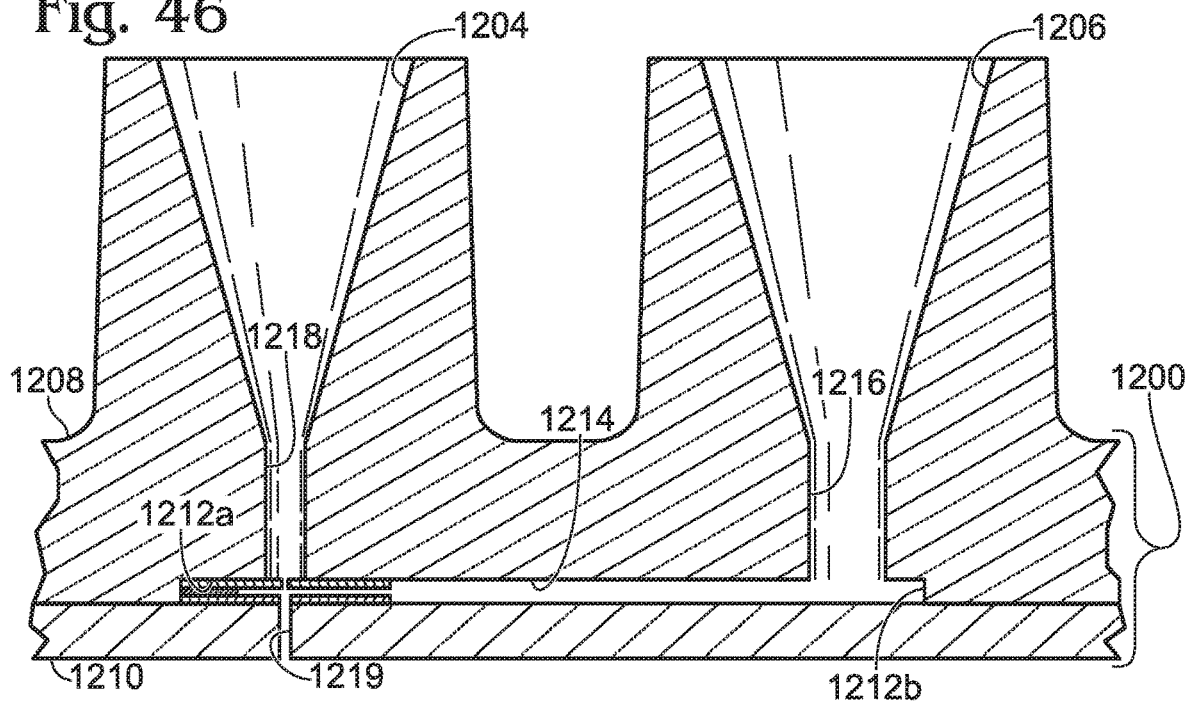
FIG. 46 is a magnified sectional view of a portion of the droplet generation system of FIG. 45.
Figure 47:
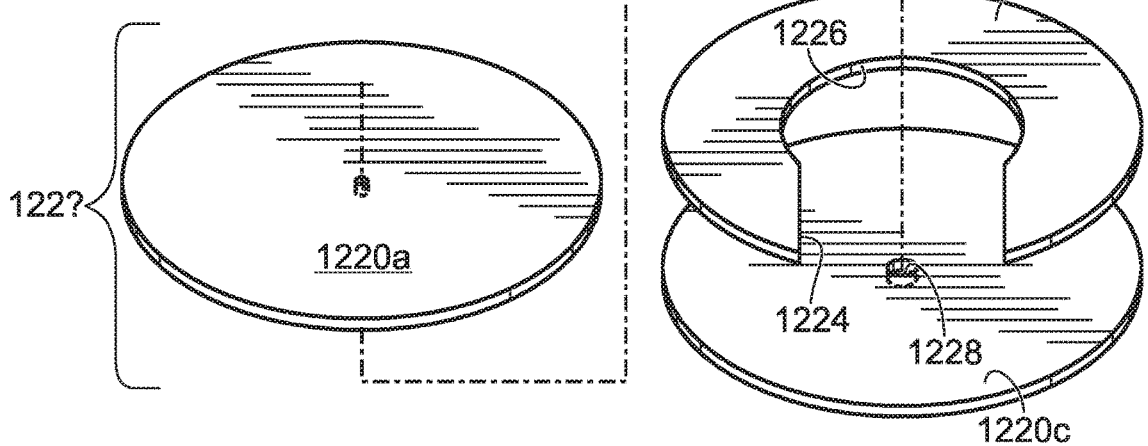
FIG. 47 is an exploded isometric view of a disk stack of the droplet generation system of FIG. 45.

FIGS. 45-47 depict another example of a single hole mode droplet generation system, generally indicated at 1200. System 1200 is similar in some respects to system 1150. Specifically, system 1200 includes a substrate 1202, upon which are disposed a sample well 1204 and a background fluid well 1206. As in the case of system 1150, the sample well and the background fluid well of system 1250 may or may not be integrally formed with the substrate, and the substrate of system 1250 may or may not be substantially planar.

In a slight distinction from system 1150, substrate 1202 of system 1200 includes two primary layers of stacked material 1208, 1210, rather than three layers. These material layers again may be bonded together by any suitable method. One of layers 1208, 1210, which in this example is upper layer 1208, includes a pair of circular depressions, 1212a, 1212b, connected by a background fluid channel 1214. Channel 1214 is shown with a two-dimensional rectangular shape, but can take any desired form, including a linear or non-linear elongate, substantially one-dimensional channel.

Background fluid well 1206 has an aperture 1216 extending through upper material layer 1208, to fluidically connect background fluid well 1206 with circular depression 1212a and thus with background fluid channel 1214. Similarly, sample well 1204 has an aperture 1218 extending through upper material layer 1208. Furthermore, a complementary droplet outlet channel 1219 extends through lower material layer 1210. Sandwiched between material layers 1208 and 1210, and disposed within circular depression 1212a, is a disk stack generally indicated at 1220. Disk stack 1220 includes three disks 1220a, 1220b, 1220c, stacked together and connected by any suitable method such as fusion welding or gluing.

When system 1200 is assembled, disk stack 1220 defines a droplet generation region as follows. Upper disk 1220a includes a sample inlet hole 1222 configured to transport sample-containing fluid from aperture 1218a through disk 1220a. Middle disk 1220b includes a background fluid inlet portion 1224 configured to fluidically interconnect with background fluid channel 1214, and a droplet generation region 1226 where sample-containing fluid emitted by sample inlet hole 1222 intersects with background fluid transported through background fluid inlet 1224, to form sample-containing droplets suspended in background fluid. Lower disk 1220c includes a droplet outlet hole 1228, which is aligned with sample inlet hole 1222.

In some cases, sample inlet hole 1222 and droplet outlet hole 1228 may be formed in a single operation such as by drilling the holes after disk stack 1220 is assembled, in which case the holes will have the same size and will automatically be substantially perfectly aligned. In other cases, however, it may be desirable to give the sample inlet hole and the droplet outlet hole different diameters and/or geometries, for example to control the rate of droplet formation by system 1200. In these cases, sample inlet hole 1222 and droplet outlet hole 1228 may be formed separately, before disk stack 1220 is assembled, and then aligned with each other prior to assembly of the disk stack.

Figure 48:
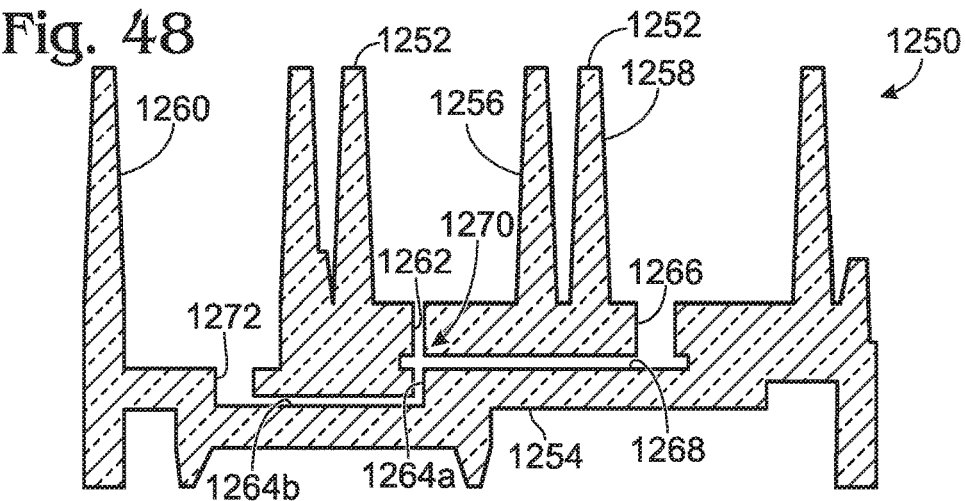
FIG. 48 is a stylized sectional view of another droplet generation system, in accordance with aspects of the present teachings.
Figure 49:
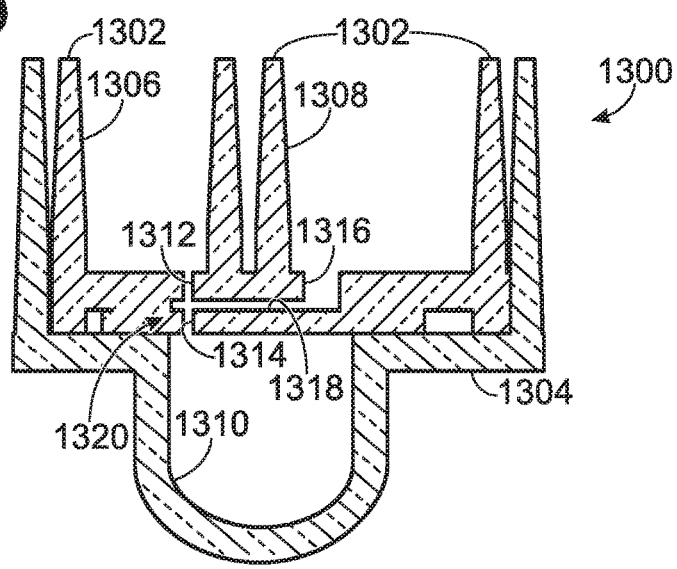
FIG. 49 is a stylized sectional view of still another droplet generation system, in accordance with aspects of the present teachings.
Figure 50:
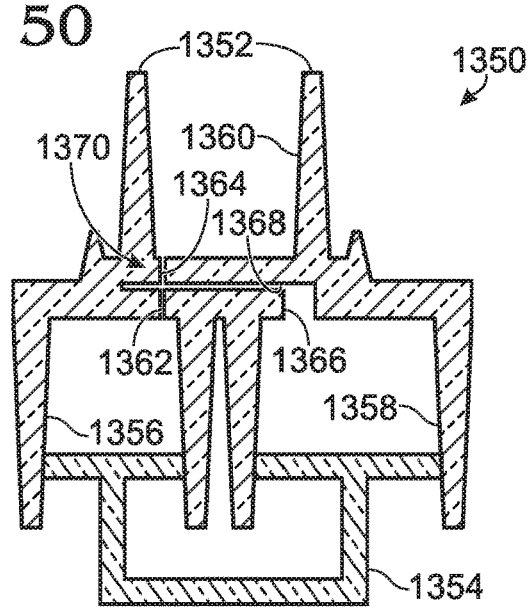
FIG. 50 is a stylized sectional view of yet another droplet generation system, in accordance with aspects of the present teachings.

FIGS. 48-50 depict stylized sectional views of additional examples that may be characterized as single hole mode droplet generations systems. As described in more detail below, each of these systems includes a plurality of wells and channels that may be integrally formed as a single component or as a pair of components that may be quickly and easily joined together, with a sample fluid channel and a droplet outlet channel that may be formed in a single operation.

FIG. 48 is a stylized sectional view of a first example of the type of system described in the previous paragraph. Specifically, FIG. 48 depicts a droplet generation system, generally indicated at 1250, formed from two sections of material 1252 and 1254. Each of sections 1252, 1254 may be injection molded, and configured to snap or otherwise fit together in desired alignment. Alternatively, a similar exemplary system may be formed from a single piece of material, for example by injection molding, and then suitably processed to become a functional droplet generation system.

In any case, assembled system 1250 includes a sample well 1256, a background fluid well 1258, and a droplet well 1260. As FIG. 48 shows, sample well 1256 is formed in material section 1252, whereas background fluid well 1258 and droplet well 1260 are partially formed by each of sections 1252 and 1254. Material section 1252 also defines a sample-containing fluid channel 1262, which may be formed in section 1252, for example, by drilling or laser scribing. If materials sections 1252 and 1254 are joined together before fluid channel 1262 is formed, the same formation operation also may be used to form a first droplet channel segment 1264a, if that channel is not formed by the natural interface of sections 1252 and 1254.

Integration of sections 1252 and 1254 also results in the formation of a background fluid outlet aperture 1266, a background fluid channel 1268, a droplet generation region generally indicated at 1270, a second droplet channel segment 1264b, and a droplet outlet aperture 1272. All of the described channels collectively form an integrated network of channels configured to fluidically interconnect the sample well, the background fluid well, and the droplet well, and to define droplet generation region 1270. Accordingly, when positive pressure is applied to sample well 1256 and background fluid well 1258, and/or negative pressure is applied to droplet well 1260, sample-containing fluid and background fluid will each travel to droplet generation region 1270, where sample-containing droplets suspended in background fluid will be generated. The resulting emulsion will then travel to, and be collected in, droplet well 1260.

FIG. 49 shows a stylized sectional view of another example that can be characterized as a single hole droplet generation system, generally indicated at 1300. System 1300 is similar in many respects to system 1250. As in the previous example, system 1300 includes two material sections 1302 and 1304, which collectively define a sample well 1306, a background fluid well 1308, a droplet well 1310, a sample-containing fluid channel 1312, a droplet channel 1314, a background fluid outlet aperture 1316, a background fluid channel 1318, and a droplet generation region generally indicated at 1320. In system 1300, however, droplet well 1310 is disposed under the sample well and the background fluid well (in the orientation of FIG. 49), and therefore may be characterized as a catch well. Accordingly, system 1300 may be operated in conjunction with a centrifuge, to cause fluid transfer and droplet generation by the inertial forces associated with spinning the system.

FIG. 50 shows a stylized sectional view of still another example that can be characterized as a single hole droplet generation system, generally indicated at 1350. System 1350 is similar in many respects to systems 1250 and 1300. As in the previous examples, system 1350 includes two material sections 1352 and 1354, which collectively define a sample well 1356, a background fluid well 1358, a droplet well 1360, a sample-containing fluid channel 1362, a droplet channel 1364, a background fluid outlet aperture 1366, a background fluid channel 1368, and a droplet generation region generally indicated at 1370.

System 1350, however, is configured so that sample-containing fluid and background fluid are respectively placed in sample well 1356 and background fluid well 1358 while the system is inverted relative to the orientation depicted in FIG. 50, and before material section 1354 is integrated with section 1352. After material section 1354 is positioned to cover the sample well and the background fluid well, system 1350 then may be inverted to the orientation of FIG. 50, at which point compressing material sections 1352 and 1354 together will cause pressure within sample well 1356 and background fluid well 1358, and thus cause droplets to be generated and transported into droplet well 1360.

VII. Exemplary Methods of Operation

This section describes exemplary methods of operating droplet generation systems, including at least some of the systems described above, according to aspects of the present teachings; see FIGS. 51-52.

FIG. 51 is a flowchart depicting an exemplary method, generally indicated at 1400, of generating sample-containing droplets suspended in a background fluid according to aspects of the present teachings. Method 1400 may be generally suitable for use with various droplet generation systems described according to the present teachings, at least including any of the systems shown in FIGS. 8-24 and described in the accompanying text above.

At step 1402, sample-containing fluid is transported into a sample well attached to a substrate. At step 1404, background fluid is transported into a background fluid well attached to the substrate. At step 1406, sample-containing fluid is transported through a first channel formed in the substrate, from the sample well to a droplet generation region. At step 1408, background fluid is transported through a second channel formed in the substrate, from the background fluid well to the droplet generation region. At step 1410, sample-containing droplets suspended in the background fluid are generated at the droplet generation region. At step 1412, the sample-containing droplets are transported through a third channel formed in the substrate, from the droplet generation region to a droplet outlet region attached to the substrate.

Method 1400 may include more detailed steps than the basic steps described so far. For example, transporting the sample-containing fluid through the first channel may include transporting the sample-containing fluid through an air trap region configured to prevent inadvertent transport of the sample-containing fluid to the droplet generation region. In addition, transporting background fluid through the second channel may include transporting the background fluid through two background fluid sub-channels that intersect the first channel from two different directions to form a cross-shaped intersection region with the first channel and the third channel. Furthermore, generating sample-containing droplets may include generating droplets having volumes in the range of 0.1 nanoliters to 10 nanoliters. Any other details consistent with the disclosed droplet generation systems may be used in the steps of method 1400.

Aside from more details in the steps of method 1400, various additional steps may be performed. For example, method 1400 may include, as generally indicated at step 1409, applying negative pressure to the droplet well and/or applying positive pressure to one or more of the sample well and the background fluid well, to cause transport of the fluids through the various channels and thus to cause droplet generation. As has been previously described, pressure may be applied by any suitable means, including at least pressure-controlled pumping, vacuum-controlled pumping, centrifugation, gravity-driven flow, and positive displacement pumping.

FIG. 52 is a flow chart depicting another method, generally indicated at 1450, for generating sample-containing droplets suspended in a background fluid according to aspects of the present teachings. As described below, method 1450 includes the step of integrating at least two components of a droplet generation system with each other, and thus may be suitable for use with any of the systems described previously that include two or more separate components. At step 1452, sample-containing fluid is transported into a sample well. At step 1454, background fluid is transported into a background fluid well.

At step 1456, at least one of the sample well or the background fluid well is integrated with a droplet generator housing, which may in some cases take the form of a substrate. At step 1458, sample-containing fluid is transported through a first channel formed in the housing, from the sample well to a droplet generation region. At step 1460, background fluid is transported through a second channel formed in the housing, from the background fluid well to the droplet generation region. At step 1462, sample-containing droplets suspended in the background fluid are generated at the droplet generation region. At step 1464, the sample-containing droplets are transported through a third channel formed in the substrate, from the droplet generation region to a droplet outlet region attached to the substrate.

As in the case of method 1400, method 1450 may include more detailed steps than the basic steps described above. For example, transporting the sample-containing fluid through the first channel may include transporting the sample-containing fluid through an air trap region configured to prevent inadvertent transport of the sample-containing fluid to the droplet generation region, transporting background fluid through the second channel may include transporting the background fluid through two background fluid sub-channels that intersect the first channel from two different directions to form a cross-shaped intersection region with the first channel and the third channel, and generating sample-containing droplets may include generating droplets having volumes in the range of 0.1 nanoliters to 10 nanoliters. Any other details consistent with the disclosed droplet generation systems may be used in the steps of method 1450.

Also as in the case of method 1400, various additional steps of method 1450 may be performed. For example, as generally indicated at step 1461, method 1450 may include applying negative pressure to the droplet well and/or applying positive pressure to one or more of the sample well and the background fluid well, to cause transport of the fluids through the various channels and thus to cause droplet generation. As has been previously described, pressure may be applied by any suitable means, including at least pressure-controlled pumping, vacuum-controlled pumping, centrifugation, gravity-driven flow, and positive displacement pumping.

VIII. Exemplary Numbered Paragraphs

This section describes additional aspects and features of droplet generation for droplet-based assays, presented without limitation as a series of numbered paragraphs.

Prototype (Two-Piece) Planar Mode

1. A system for forming a plurality of sample-containing droplets suspended in a background fluid, comprising (A) a substrate having a top surface and a bottom surface; (B) a sample port formed in the top surface of the substrate; (C) a background fluid port formed in the top surface of the substrate; (D) a droplet outlet port formed in the top surface of the substrate; (E) a network of channels formed in the bottom surface of the substrate and configured to fluidically interconnect the sample port, the background fluid port, and the droplet outlet port; (F) a droplet generation region defined by the network of channels and configured to generate sample-containing droplets suspended in the background fluid; and (G) a well vessel including a sample well configured to make a substantially fluid tight connection with the sample port, a background fluid well configured to make a substantially fluid tight connection with the background fluid port, and a droplet outlet well configured to make a substantially fluid tight connection with the droplet outlet port; wherein the droplet generation region is defined by the intersection of at least a first channel, a second channel, and a third channel, and wherein the first channel is configured to transport sample-containing fluid from the sample port to the droplet generation region, the second channel is configured to transport background fluid from the background fluid port to the droplet generation region, and the third channel is configured to transport sample-containing droplets from the droplet generation region to the droplet outlet port.

Continuous Mode

2. A system for forming a plurality of sample-containing droplets suspended in a background fluid, comprising (A) a sample well; (B) a droplet generator configured to receive sample-containing fluid from the sample well; (C) a droplet outlet region configured to receive sample-containing droplets from the droplet generator; and (D) a housing configured to selectively receive the droplet generator, the housing including a background fluid input channel configured to provide background fluid to the droplet generator from a background fluid source; wherein the droplet generator is configured to generate sample-containing droplets suspended in the background fluid, and to direct the droplets toward the droplet outlet region.

3. The system of paragraph 2, wherein at least one of the droplet generator and the droplet outlet region are integrally formed with the sample well.

Two-Part Mode

4. A system for forming a plurality of sample-containing droplets suspended in a background fluid, comprising (A) a sample well; (B) a sample channel configured to transport sample-containing fluid from the sample well to a droplet generation region; (C) a housing configured to selectively receive the sample channel; (D) a background fluid channel integrally formed with the housing and configured to transport background fluid from a background fluid source to the droplet generation region; and (E) a droplet channel integrally formed with the housing and configured to transport sample-containing droplets from the droplet generation region to a droplet outlet; wherein the droplet generation region is disposed within the housing and is defined by a region of intersection of the sample channel, the background fluid channel, and the droplet channel.

5. The system of paragraph 4, wherein the sample channel is integrally formed with the sample well.

Single-Hole Mode

6. A system for forming a plurality of sample-containing droplets suspended in a background fluid, comprising (A) a droplet generator plate; (B) a sample well attached to the droplet generator plate; (C) a background fluid well attached to the droplet generator plate; (D) a droplet generation region formed within the droplet generator plate; (E) a background fluid channel formed within the droplet generator plate and configured to transport background fluid from the background fluid well to the droplet generation region; (F) a sample channel configured to transport sample-containing fluid from the sample well to the droplet generation region; and (G) a droplet outlet channel configured to transport sample-containing droplets from the droplet generation region to a droplet outlet formed in the droplet generator plate; wherein the sample inlet channel and the droplet outlet channel are integrally formed from a pair of aligned apertures which are separated by the background fluid channel.

7. The system of paragraph 6, wherein the sample inlet channel and the droplet outlet channel are each formed in the droplet generator plate.

8. The system of paragraph 7, wherein the sample inlet channel and the droplet outlet channel are integrally formed by a single drilling operation that passes through two rigidly attached planar surfaces of the droplet generator plate.

9. The system of paragraph 6, wherein the sample inlet channel and the droplet outlet channel are each formed in an insertable droplet generator member configured to be disposed within the droplet generator plate.

10. The system of paragraph 9, wherein the sample inlet channel and the droplet outlet channel are integrally formed by a single drilling operation that passes through two rigidly attached planar surfaces of the droplet generator member.

11. The system of paragraph 6, wherein at least one of the sample well and the background fluid well are integrally formed with the droplet generator plate.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

We claim:

1. A method of emulsion formation and modification, the method comprising:
    flowing an oil in an oil channel and a first aqueous fluid in an aqueous channel, wherein the oil channel, the aqueous channel, and an emulsion channel intersect at a first intersection;
    forming an emulsion including the first aqueous fluid at the first intersection;
    flowing the emulsion in the emulsion channel to a second intersection; and
    modifying the emulsion at the second intersection, wherein modifying comprises generating droplets including a second aqueous fluid, wherein the modified emulsion comprises a first population of droplets including the first aqueous fluid and a second population of droplets including the second aqueous fluid, and wherein the first population and the second population have different compositions;
    wherein the aqueous channel in which the first aqueous fluid flows has a cross-section and includes an air trap configured to prevent the first aqueous fluid from being inadvertently drawn through the aqueous channel by capillary action;
    wherein the air trap includes three sections, each of which is formed with at least one angled channel through which sample-containing fluid passes to flow through the air trap; and
    wherein the cross-section of the aqueous channel abruptly increases in one or more dimensions to increase the contact angle of the first aqueous fluid and the aqueous channel wall interface to a value greater than 90 degrees to generate a force that stops an undesired movement of the first aqueous fluid in the aqueous channel.

2. The method of claim 1, further comprising thermally cycling the first and second populations of droplets.

3. The method of claim 1, further comprising amplifying a nucleic acid target in each population of droplets.

4. The method of claim 1, further comprising detecting fluorescence from the first and second populations of droplets.

5. The method of claim 1, further comprising placing the first aqueous fluid into a vessel; and removably connecting the vessel to the first intersection.

6. The method of claim 5, further comprising driving the first aqueous fluid from the vessel to the first intersection.

7. The method of claim 1, wherein each of the first and second aqueous fluids includes a surfactant.

8. The method of claim 1, wherein the oil includes a fluorocarbon oil.

* * * * *